(12) United States Patent
Dimitrov et al.

(10) Patent No.: US 9,127,056 B2
(45) Date of Patent: Sep. 8, 2015

(54) MONOSPECIFIC AND BISPECIFIC HUMAN MONOCLONAL ANTIBODIES TARGETING INSULIN-LIKE GROWTH FACTOR II (IGF-II)

(71) Applicant: The United States of America, as represented by the Secretary, Department of Health and Human, Washington, DC (US)

(72) Inventors: Dimiter S. Dimitrov, Frederick, MD (US); Weizao Chen, Frederick, MD (US); Yang Feng, Frederick, MD (US)

(73) Assignee: The United States of America, as Represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 14/352,312

(22) PCT Filed: Oct. 16, 2012

(86) PCT No.: PCT/US2012/060443
§ 371 (c)(1),
(2) Date: Apr. 16, 2014

(87) PCT Pub. No.: WO2013/059206
PCT Pub. Date: Apr. 25, 2013

(65) Prior Publication Data
US 2014/0271646 A1 Sep. 18, 2014

Related U.S. Application Data

(60) Provisional application No. 61/548,164, filed on Oct. 17, 2011.

(51) Int. Cl.
| | | |
|---|---|---|
| A61K 39/395 | (2006.01) | |
| G01N 33/53 | (2006.01) | |
| C07K 16/22 | (2006.01) | |
| C12N 15/13 | (2006.01) | |
| C12N 5/10 | (2006.01) | |
| G01N 33/574 | (2006.01) | |
| G01N 33/74 | (2006.01) | |
| A61K 39/00 | (2006.01) | |

(52) U.S. Cl.
CPC .......... *C07K 16/22* (2013.01); *G01N 33/57488* (2013.01); *G01N 33/74* (2013.01); *A61K 2039/505* (2013.01); *C07K 2317/31* (2013.01); *C07K 2317/55* (2013.01); *C07K 2317/56* (2013.01); *C07K 2317/565* (2013.01); *C07K 2317/60* (2013.01); *C07K 2317/622* (2013.01); *C07K 2317/64* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 5,840,526 A | 11/1998 | Casterman et al. |
| 2009/0130105 A1 | 5/2009 | Glaser et al. |
| 2009/0181022 A1 | 7/2009 | Nielsen et al. |
| 2010/0055033 A1 | 3/2010 | Dimitrov et al. |
| 2010/0081796 A1 | 4/2010 | Brinkmann et al. |
| 2010/0092460 A1 | 4/2010 | Blanchetot et al. |
| 2011/0008358 A1 | 1/2011 | Dimitrov et al. |
| 2011/0104163 A1 | 5/2011 | Dimitrov et al. |
| 2011/0123529 A1 | 5/2011 | Laeremans et al. |

FOREIGN PATENT DOCUMENTS

| | | |
|---|---|---|
| WO | WO2004/003019 | 1/2004 |
| WO | WO2005/058967 | 6/2005 |
| WO | WO2007/000328 | 1/2007 |
| WO | WO2007/022172 | 2/2007 |
| WO | WO2007/070432 | 6/2007 |
| WO | WO2009/134776 | 11/2009 |

OTHER PUBLICATIONS

Asano et al., "Highly effective recombinant format of a humanized IgG-like bispecific antibody for cancer immunotherapy with retargeting of lymphocytes to tumor cells," *Journal of Biological Chemistry* 282(38): 27659-27665, (Sep. 21, 2007).

Chames and Baty, "Bispecific antibodies for cancer therapy: The light at the end of the tunnel?," *mAbs* 1(6):539-547 (2009).

Chen et al., "Human monoclonal antibodies targeting nonoverlapping epitopes on insulin-like growth factor II as a novel type of candidate cancer therapeutics", *Molecular Cancer Therapeutics* 11(7):1400-1410 (Jul. 2012).

Dong et al., "A stable IgG-like bispecific antibody targeting the epidermal growth factor receptor and the type I insulin-like growth factor receptor demonstrates superior anti-tumor activity," *mAbs* 3(3):273-288 (2011).

(Continued)

*Primary Examiner* — Marianne P Allen
(74) *Attorney, Agent, or Firm* — Klarquist Sparkman, LLP

(57) ABSTRACT

Monoclonal antibodies (mAbs), antigen binding fragments and engineered antibody domains (eAds) that specifically bind IGF-II are disclosed herein. In some embodiments, these mAbs and eAds are included in a bispecific mAb. In some embodiments, the bispecific antibody specifically binds two different epitopes of IGF-II. Methods of using these mAbs, antigen binding fragments, and eAds, bispecific antibodies, and nucleic acids encoding these mAbs, antigen binding fragments, and eAds, bispecific antibodies are also disclosed.

41 Claims, 9 Drawing Sheets

(56) References Cited

OTHER PUBLICATIONS

Dong et al., "Stable IgG-like bispecific antibodies directed toward the type I insulin-like growth factor receptor demonstrate enhanced ligand blockade and anti-tumor activity," *Journal of Biological Chemistry* 286(6):4703-4717 (Feb. 11, 2011).

Hudson and Souriau, "Engineered antibodies," *Nature Medicine* 9(1):129-134 (Jan. 2003).

Peyrat et al., "Plasma insulin-like growth factor-1 (IGF-1) concentrations in human breast cancer," *Eur. J. Cancer* 29A(4):492-497 (1993) (abstract only).

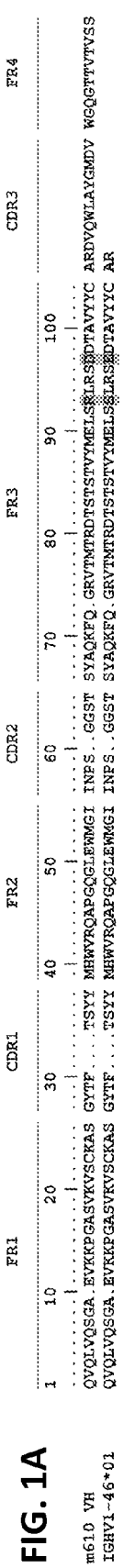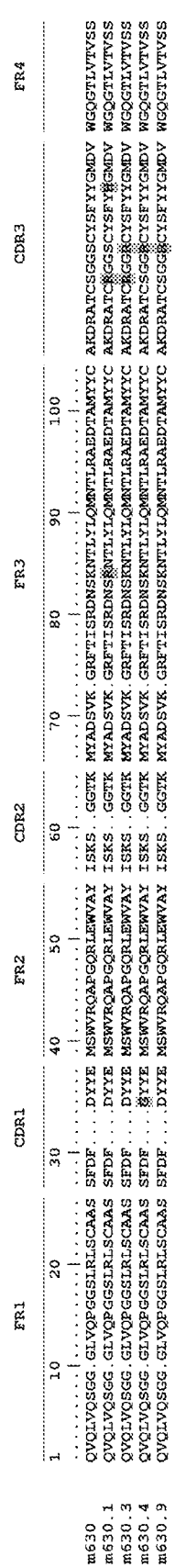

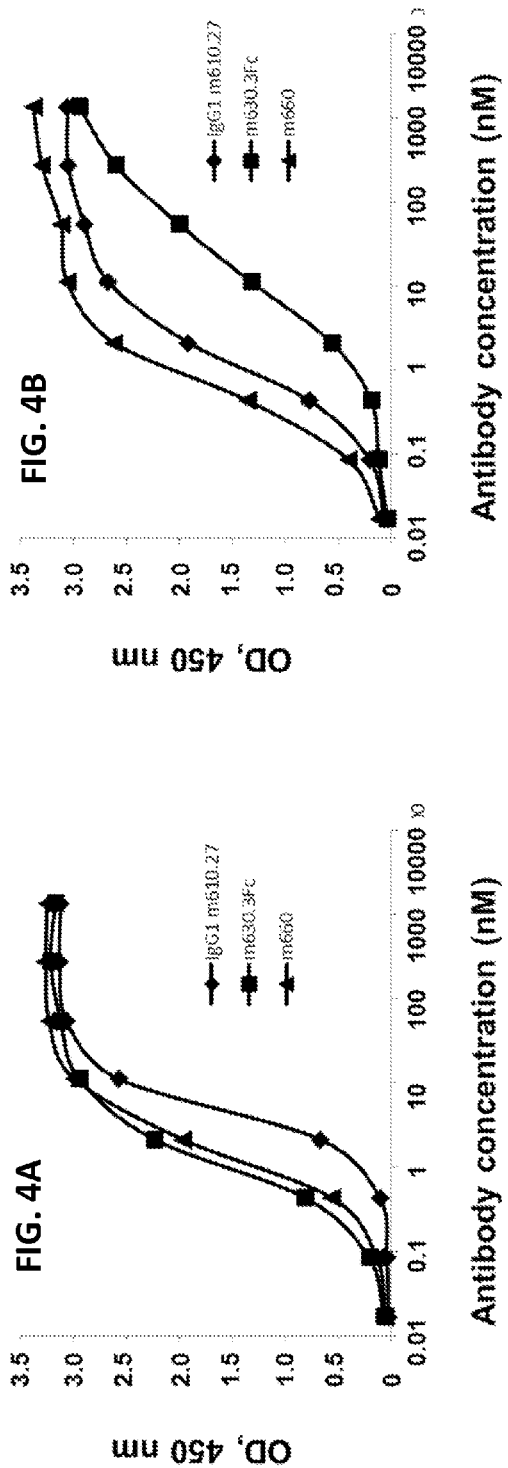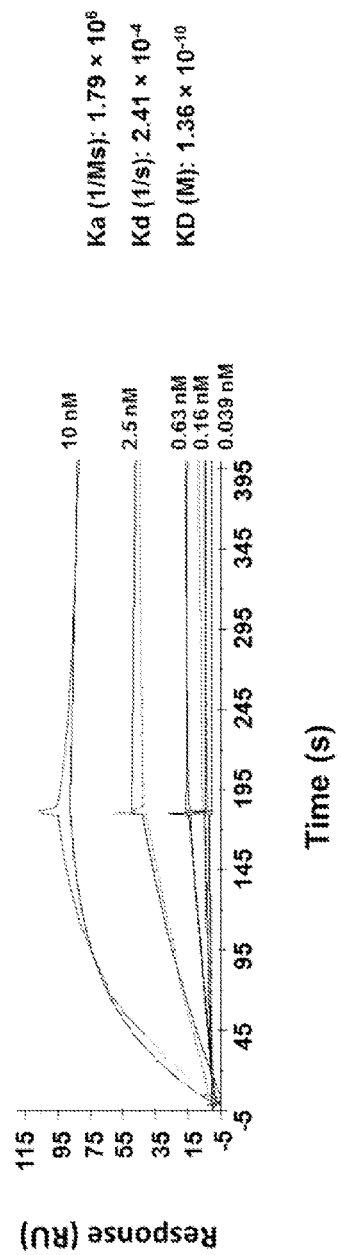

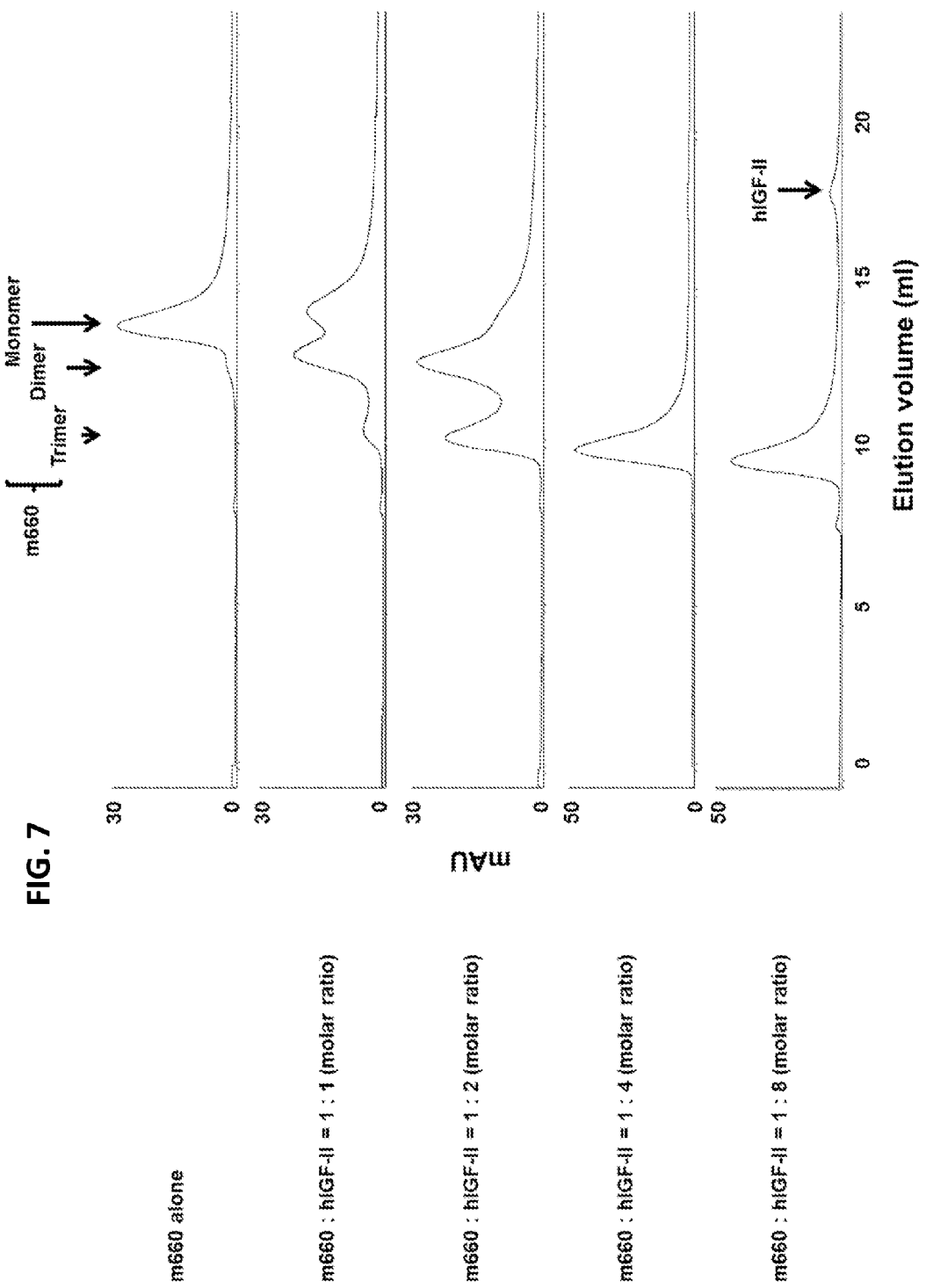

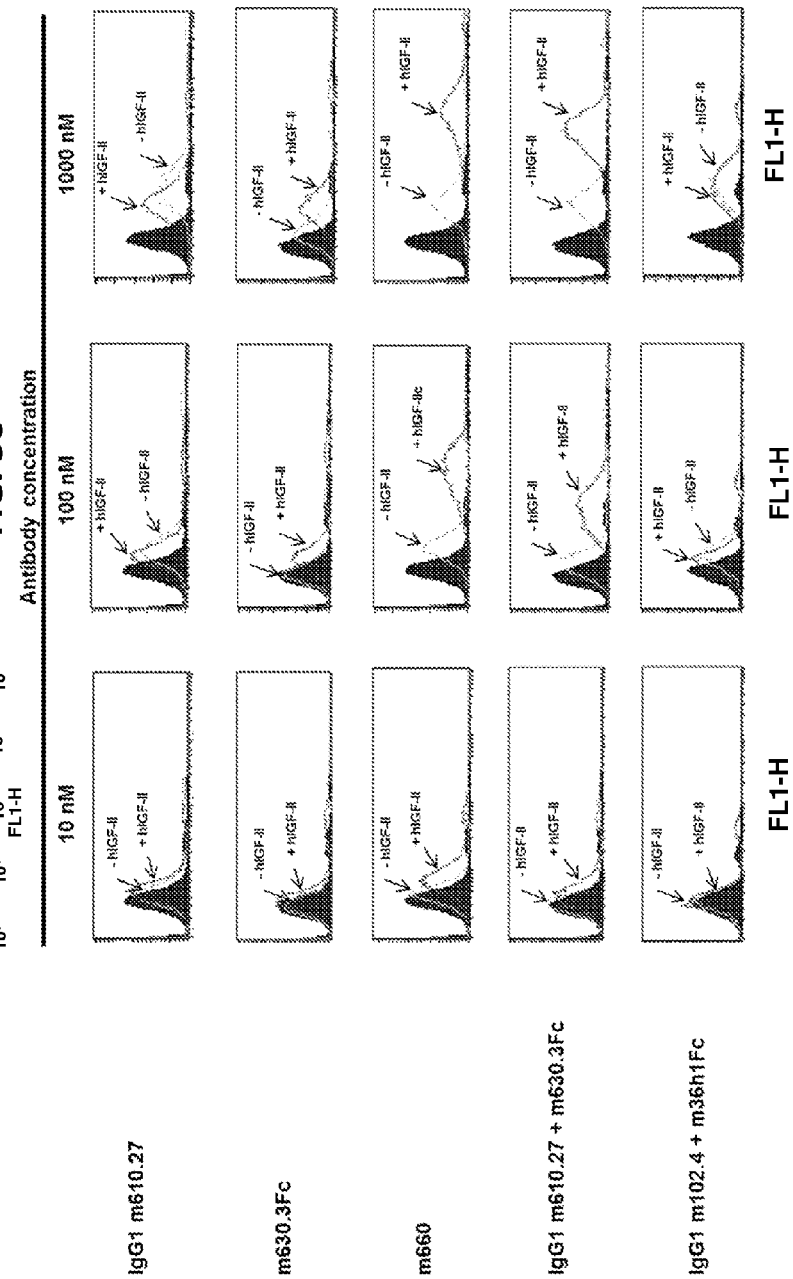

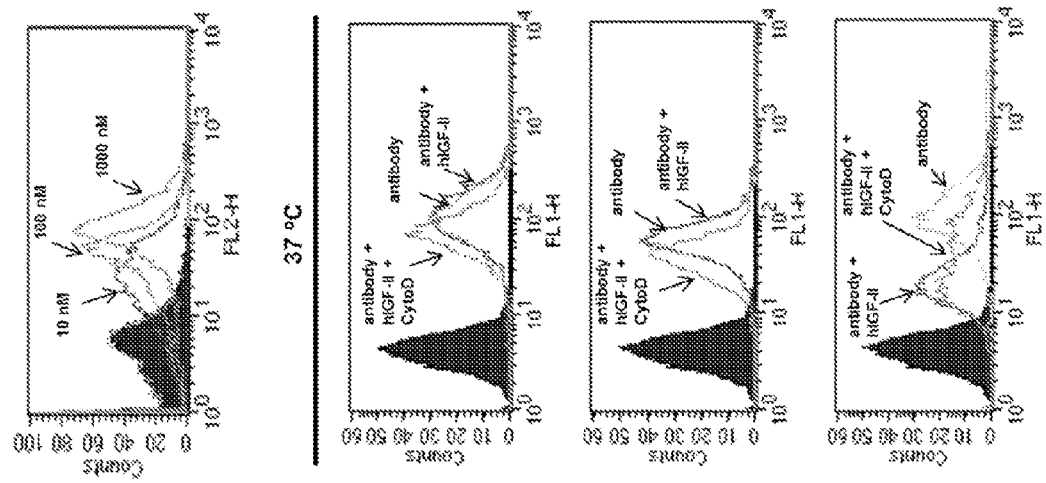
FIG. 9A
FIG. 9B
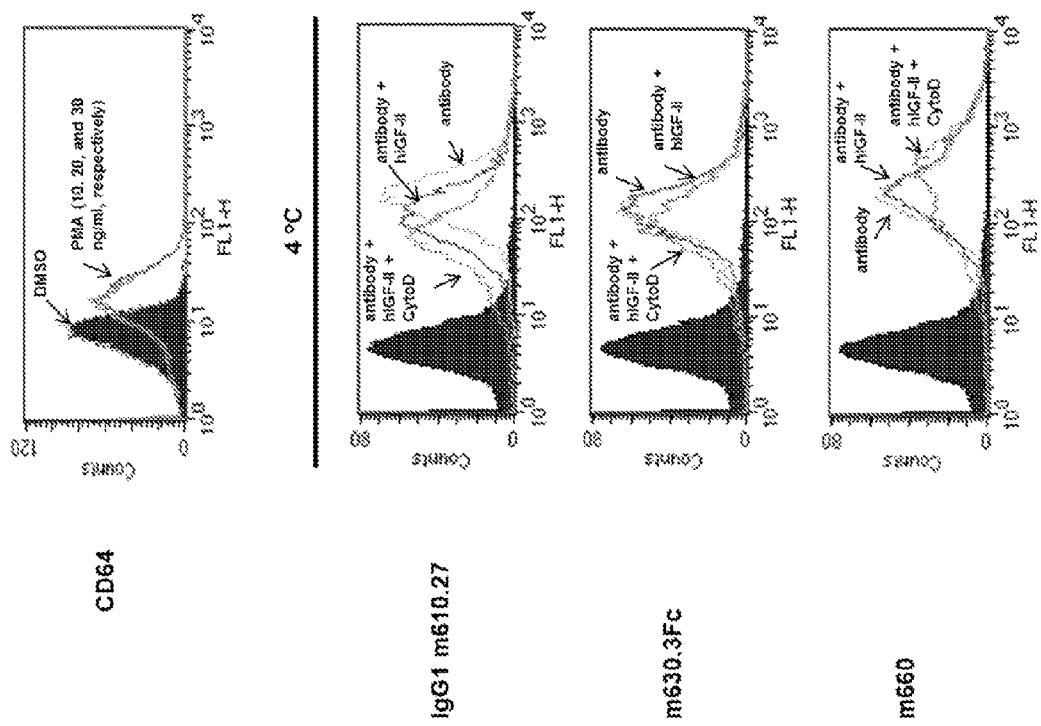
FIG. 9C

MONOSPECIFIC AND BISPECIFIC HUMAN MONOCLONAL ANTIBODIES TARGETING INSULIN-LIKE GROWTH FACTOR II (IGF-II)

CROSS REFERENCE TO RELATED APPLICATIONS

This the U.S. national stage of PCT Application No. PCT/US2012/060443, filed Oct. 16, 2012, which was published in English under PCT Article 21(2), which application claims the benefit of U.S. Provisional Application No. 61/548,164, filed Oct. 17, 2011, which is incorporated by reference in its entirety.

FIELD OF THE DISCLOSURE

This application relates to monoclonal antibodies (mAbs), bispecific antibodies and engineered antibody domains (eAds) that specifically bind insulin-like growth factor II (IGF-II), and their use to diagnose and treat cancer.

BACKGROUND

There is an increasing interest in targeting soluble ligands as a compensation strategy for receptor-directed therapy of diseases mediated by ligand-receptor interactions. Insulin-like growth factors (IGFs), IGF-I and IGF-II, are circulating small soluble ligands (Ryan and Goss, 2008, Oncologist 13:16-24; Samani et al., 2007, Endocr Rev 28:20-47). They bind to the IGF receptor type I (IGF-IR) and activate multiple intracellular signaling pathways resulting in cell proliferation, survival, differentiation, and transformation. IGF-II also binds to insulin receptor (IR), primarily A isoform (IR-A), with high affinity. Many cells and tissues have hybrid receptors assembled with one chain of the IGF-IR and one of the IR. Elevated expression of the receptors and/or the ligands has been detected in some cancer tissues such as human breast carcinomas and linked to the pathogenesis of them.

Small-molecule tyrosine kinase inhibitors and mAbs against IGF-IR have shown benefits in human clinical trials (Ryan and Gross, supra). However, resistance to the IGF-IR-directed agents has developed (Hendrickson and Haluska, 2009, Curr Opin Investig Drugs 10:1032-40). A possible resistance mechanism is that cancer development and progression could rely solely on the actions taken by IR when the IGF-IR pathway is blocked. Thus, targeting both IR and IGF-IR may be necessary to completely inhibit the signal transductions. While IR is also functionally important for glucose homeostasis, targeting IGF-II is another strategy which could leave the insulin-IR interactions unaffected. Recently, several mAbs specific to IGF-II (or cross-reactive with IGF-I) have been identified that inhibit the growth and migration of human cancer cells in vitro and in vivo (Dransfield et al., 2010, Mol Cancer Ther 9:1809-19; Feng et al., 2006, Mol Cancer Ther 5:114-20; Gao et al., 2011, Cancer Res 71:1029-40; Goya et al., 2004, Cancer Res 64:6252-8; Kimura et al., 2010, Clin Cancer Res 16:121-9). However, a need remains for additional agents that target IGF-II and efficiently irreversibly remove it from the circulation.

SUMMARY OF THE DISCLOSURE

MAbs and engineered antibody domains (eAds) that specifically bind a ligand, specifically IGF-II, are disclosed herein. In some embodiments, these mAbs and eAds are included in a bispecific antibody. In some embodiments, the bispecific antibody specifically binds two different epitopes of IGF-II.

In some embodiments, the bispecific antibody includes an eAd that specifically binds a first epitope of IGF-II, and mAb or an antigen binding fragment thereof, such as (but not limited to) a single-chain Fv (scFv) that specifically binds a second epitope of IGF-II, wherein the first epitope and the second epitope are different.

Nucleic acids encoding these mAbs, eAds and bispecific antibodies, vectors including these nucleic acids, and host cells transformed with these vectors are also disclosed herein.

Method of using these mAbs, eAds, bispecific antibodies, nucleic acids, expression vectors and host cells are also disclosed. In some embodiments, methods are provided for detecting cancer. In additional embodiments, methods are provided for treating cancer, such as breast cancer. In further embodiments, methods are also provided for inhibiting the phosphorylation of the IGF-IR and IR, and for detecting IGF-II.

The foregoing and other features and advantages of the invention will become more apparent from the following detailed description of a several embodiments which proceeds with reference to the accompanying figures.

BRIEF DESCRIPTION OF THE FIGURES

FIGS. 1A-1B: The amino acid sequences of m610.27 (FIG. 1A) and m630.3 (FIG. 1B) in alignment with their corresponding germlines of human antibody V genes and/or wild types. The complementarity determining regions (CDRs) and framework regions (FRs) are indicated according to the ImMunoGeneTics annotation (imgt.cines.fr/). The somatic mutations in the V genes of the antibodies and the mutations induced by random mutagenesis are highlighted with gray background. In FIG. 1A, the m610.27 $V_H$ amino acid sequence is SEQ ID NO: 1. The germline sequence (IGVH1-46*01, SEQ ID NO: 34) is SEQ ID NO: 1, wherein position 93 is substituted for an S, position 97 is substituted for an E. The m610.27 $V_L$ amino acid sequence is SEQ ID NO: 2. The germline sequence (IGKV1-39*01, SEQ ID NO: 35) is SEQ ID NO: 2, wherein position 10 is a S. A comparison is also shown to m610 (SEQ ID NO: 36), which is SEQ ID NO: 1 with the following substitutions: position 10 is a P, position 48 is a K, position 51 is a K, position 55 is a Y, position 103 is a Y, the $6^{th}$ amino acid of CDR3 is a T, the $8^{th}$ amino acid of CDR3 is an L and the last amino acid of FR4 is a R. In FIG. 1B, m630 is SEQ ID NO: 5, wherein $X_1$ is D, $X_2$ is K, $X_3$ is S, $X_4$ is S, and $X_5$ is Y; m630.1 is SEQ ID NO: 5, wherein $X_1$ is D, $X_2$ is R, $X_3$ is R, $X_4$ is S, and $X_5$ is H; m630.3 is SEQ ID NO: 5, wherein $X_1$ is D, $X_2$ is K, $X_3$ is R, $X_4$ is R, and $X_5$ is Y; m630.4 is SEQ ID NO: 5, wherein $X_1$ is G, $X_2$ is K, $X_3$ is S, $X_4$ is R, and $X_5$ is Y; m630.9 is SEQ ID NO: 5, wherein $X_1$ is D, $X_2$ is K, $X_3$ is S, $X_4$ is R, and $X_5$ is Y.

(FIG. 2A) Fab m610.27 was converted to an $IgG_1$ format regularly. (FIG. 2B) m630.3Fc was constructed by joining eAd m630.3 to the N terminus of human IgG1 Fc through a hinge linker. (FIG. 2C) The bispecific antibody, m660, was generated by fusing scFv m610.27 and eAd m630.3 to the N termini of the heavy and light chain constant regions of a human IgG1, respectively, via a linker composed of three repeats of $G_4S$ motif. (FIG. 2D) Reducing and nonreducing SDS-PAGE of the antibodies purified from 293 free style cell cultures.

(FIG. 3A) Binding of IgG1 m610.27 and m630.3Fc to human IGF-II (hIGF-II), human IGF-I (hIGF-I) and human insulin. (FIG. 3B) Binding of the antibodies to mIGF-II. (FIG. 3C) Competition of m630.3Fc with IgG1 m610.27 and IgG1 m708.5 in binding to hIGF-II. (FIG. 3D) Competition of m630.3Fc with IgG1 m610.27 and IgG$_1$ m708.5 in binding to mIGF-II. In the binding ELISA, antigens were directly coated on the 96-well plates at a concentration of 2 µg/ml. Bound antibodies were detected by HRP-conjugated goat anti-human IgG (Fc-specific) antibody. In the competition ELISA, antigens were captured by the antibody competitors coated on the 96-well plates at a concentration of 2 µg/ml. Bound m630.3Fc was detected by HRP-conjugated rabbit anti-c-Myc tag antibody. The half-maximal binding ($EC_{50}$) was calculated by fitting the data to the Langmuir adsorption isotherm.

FIGS. 4A-4C: Binding activity of m660 measured by ELISA with hIGF-II (FIG. 4A) and long hIGF-II (FIG. 4B), and by SPR with hIGF-II (FIG. 4C). ELISA was performed by coating IGF-II on 96-well plates. Bound antibodies were detected by HRP-conjugated goat anti-human IgG (Fc-specific) antibody. SPR analysis was performed on Biacore X100 by according to the manufacturer's instructions. The tested antibody concentration corresponding to each sensorgram and the calculated kinetic constants are shown on the right.

FIG. 7: Size-exclusion chromatography analysis of m660-hIGF-II complexes. The bold arrows shown at the top indicate the positions where a monomer, dimer or trimer of m660 should elute. The bold arrow at the bottom indicates a small peak corresponding to the elution of free hIGF-II.

FIGS. 8A-8C: FACS binding of antibody-hIGF-II complexes to BJAB cells. (FIG. 8A) Expression of FcγRII on BJAB cells was detected by FITC-conjugated mouse anti-human CD32 (FcγRII) antibody. The diagram for reference cells is with solid fill. The diagrams for cells incubated with FITC-conjugated mouse anti-human CD16 (FcγRII) or anti-human CD32 (FcγRII) antibody at different dilutions (v/v) are indicated by arrows. (FIG. 8B) Binding of biotinylated hIGF-II to BJAB cells. Bound hIGF-II was detected by streptavidin-PE conjugate. The diagram with solid fill is for reference cells incubated with streptavidin-PE only. The diagrams for cells incubated with hIGF-II at concentrations of 10, 100, and 1,000 nM are indicated by arrows. (FIG. 8C) Interactions of antibody-hIGF-II complexes with BJAB cells. Bound antibodies in the absence or presence of hIGF-II were detected by FITC-conjugated goat F(ab')$_2$ anti-human IgG (Fc-specific) antibody. The diagrams for reference cells are with solid fill. The diagrams for cells incubated with 10 nM antibodies in the absence or presence of 20 (for monospecific antibody) or 40 (for bispecific antibody) mM hIGF-II are indicated by arrows.

FIGS. 9A-9C: FACS binding of m660-hIGF-II complexes to PMA-stimulated U937 cells. (FIG. 9A) Expression of FcγRI on U937 cells was detected by FITC-conjugated mouse anti-human CD64 (FcγRI) antibody at 1:100 dilution (v/v). The diagram for reference cells that were not stimulated is with solid fill. The diagram for cells mock-stimulated with PMA solvent Dimethyl sulfoxide (DMSO) or stimulated with 10, 20, and 30 ng/ml PMA, respectively, are indicated by arrows. (FIG. 9B) Binding of biotinylated hIGF-II to U937 cells. Bound hIGF-II was detected by streptavidin-PE conjugate. The diagrams for reference cells are with solid fill. The diagrams for cells incubated with hIGF-II at concentrations of 10, 100, and 1,000 nM are indicated by arrows. (FIG. 9C) Interactions of antibody-hIGF-II complexes with U937 cells. Bound antibodies were detected by FITC-conjugated goat F(ab')$_2$ anti-human IgG (Fc-specific) antibody. The diagram with solid fill is for the reference cells incubated with the secondary antibody only. The diagrams for cells incubated with 10 nM antibody alone, 10 nM antibody plus 20 (for all monospecific antibodies) or 40 (for m660) nM hIGF-II, and an combination of the antibody, hIGF-II and 50 µM Cytochalasin D (CytoD) are indicated by arrows.

SEQUENCE LISTING

Figure 2B:
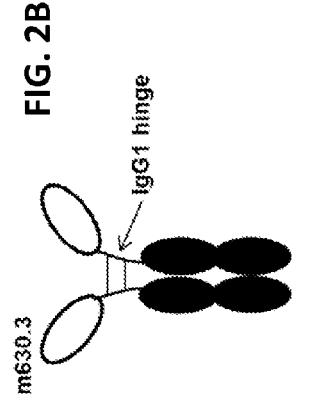
FIGS. 2A-2D: Schematic representation of antibody structures and antibody expression.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

The Sequence Listing is submitted as an ASCII text file [4239-87577-03_Sequence_Listing.txt, Apr. 8, 2014, 34.2 KB], which is incorporated by reference herein.

SEQ ID NO: 1 is the amino acid sequence of the heavy chain variable domain of m610.27.

SEQ ID NO: 2 is the amino acid sequence of the light chain variable domain of m610.27.

SEQ ID NO: 3 is the amino acid sequence of a heavy chain constant domain ($IgG_1$).

SEQ ID NO: 4 is the amino acid sequence of a light chain constant domain ($IgG_1$).

SEQ ID NO: 5 is the amino acid sequence of the eAd consensus sequence.

SEQ ID NO: 6 is the amino acid sequence of an eAd linked to an Fc domain ($IgG_1$).

SEQ ID NO: 7 is the amino acid sequence of an scFv linked to a heavy chain constant domain ($IgG_1$).

SEQ ID NO: 8 is the amino acid sequence of an eAd linked to a light chain constant domain ($IgG_1$).

SEQ ID NO: 9 is an exemplary nucleic acid sequence encoding the heavy chain of $IgG_1$ m610.27.

SEQ ID NO: 10 is an exemplary nucleic acid sequence encoding the light chain of IgG1 m610.27.

SEQ ID NO: 11 is an exemplary nucleic acid sequence encoding eAd 630.

SEQ ID NO: 12 is an exemplary nucleic acid sequence encoding eAd 630.1.

SEQ ID NO: 13 is an exemplary nucleic acid sequence encoding eAd 630.3.

SEQ ID NO: 14 is an exemplary nucleic acid sequence encoding eAd 630.4.

SEQ ID NO: 15 is an exemplary nucleic acid sequence encoding eAd 630.9.

SEQ ID NO: 16 is an exemplary nucleic acid sequence encoding eAd 630.3 and an IgG1 Fc domain.

SEQ ID NO: 17 is an exemplary nucleic acid sequence encoding the heavy chain of m660, which contains scFv m610.27 and the IgG1 heavy chain constant domain.

SEQ ID NO: 18 is an exemplary nucleic acid sequence encoding the light chain of m660, which contains eAd m630.3 and the IgG1 light chain constant domain.

SEQ ID NOs: 19-32 are the nucleic acid sequences of primers.

SEQ ID NO: 33 is the amino acid sequence of an exemplary linker.

SEQ ID NO: 34 is the germline sequence IGVH1-46*01.

SEQ ID NO: 35 is the germline sequence IGKV1-39*01.

SEQ ID NO: 36 is the amino acid sequence of the light chain variable domain of m610.

DETAILED DESCRIPTION OF SEVERAL EMBODIMENTS

Ligand-specific antibodies can be used for the detection of the ligand and for diagnosis. However, when administered in vivo for therapeutic applications, these antibodies could act as carrier proteins and make ligands generally unavailable to some clearance mechanisms such as renal filtration and proteolytic digestion because of the long half-life and high stability of antibodies (Mihara et al., 1991, Immunology 74:55-9; Rehlaender et al., 1991, Pharm Res 18:745-52). The dissociation of immune complexes allow for slow release of ligands that continue to exert functions. Murine mAbs have been shown to prolong the serum half-life and bioactivity of human interleukins in mice, although they completely neutralized the interleukins in vitro (Finkelman et al., 1993, J Immunol 151:1235-44; May et al., 1993, J Immunol 151:3225-36; Mihara et al., 1991, supra). Therefore, strategies to efficiently irreversibly eliminate ligands are desirable to promote the inhibitory activities of antibodies. As disclosed herein, bispecific antibodies can be used to remove a ligand, such as IGF-II, from the circulation.

MAbs have been identified that bind IGF-II with high affinity. In addition, eAds have been identified that surprisingly bind a different epitope of IGF-II than these mAbs. Bispecific antibodies are disclosed that include these mAbs, antigen binding fragments thereof, and eAds, and thus bind two different epitopes of IGF-II.

The mAbs, eAds, antigen binding fragments and bispecific antibodies inhibit the phosphorylation of the IGF-IR and IR, and inhibit the growth and migration of human cancer cells in vitro and in vivo. Thus, uses are disclosed for these mAbs, eAds, antigen binding fragments and bispecific antibodies, such as for detection of IGF-II, diagnosis of cancer, and treatment of cancer.

TERMS

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of this disclosure, the following explanations of specific terms are provided:

Administration: The introduction of a composition into a subject by a chosen route. For example, if the chosen route is intravenous, the composition is administered by introducing the composition into a vein of the subject.

Amplification: Of a nucleic acid molecule (such as, a DNA or RNA molecule) refers to use of a technique that increases the number of copies of a nucleic acid molecule in a specimen. An example of amplification is the polymerase chain reaction, in which a biological sample collected from a subject is contacted with a pair of oligonucleotide primers, under conditions that allow for the hybridization of the primers to a nucleic acid template in the sample. The primers are extended under suitable conditions, dissociated from the template, and then re-annealed, extended, and dissociated to amplify the number of copies of the nucleic acid. The product of amplification may be characterized by electrophoresis, restriction endonuclease cleavage patterns, oligonucleotide hybridization or ligation, and/or nucleic acid sequencing using standard techniques. Other examples of amplification include strand displacement amplification, as disclosed in U.S. Pat. No. 5,744,311; transcription-free isothermal amplification, as disclosed in U.S. Pat. No. 6,033,881; repair chain reaction amplification, as disclosed in WO 90/01069; ligase chain reaction amplification, as disclosed in EP-A-320 308; gap filling ligase chain reaction amplification, as disclosed in U.S. Pat. No. 5,427,930; and NASBA™ RNA transcription-free amplification, as disclosed in U.S. Pat. No. 6,025,134.

Animal: Living multi-cellular vertebrate organisms, a category that includes, for example, mammals and birds. The term mammal includes both human and non-human mammals. Similarly, the term "subject" includes both human and veterinary subjects.

Antibody: A polypeptide ligand comprising at least a light chain or heavy chain immunoglobulin variable region which specifically recognizes and specifically binds an epitope of an antigen, such as IGF-II, or a fragment thereof. Immunoglobulin molecules are composed of a heavy and a light chain, each of which has a variable region, termed the variable heavy ($V_H$) region and the variable light ($V_L$) region. Together, in a native antibody, the $V_H$ region and the $V_L$ region bind the antigen recognized by the antibody. In some embodiments, only the heavy chain variable domain is required. For example, naturally occurring camelid antibodies consisting of a heavy chain only are functional and stable in the absence of light chain (see, e.g., Hamers-Casterman et al., *Nature*, 363:446-448, 1993; Sheriff et al., *Nat. Struct. Biol.*, 3:733-736, 1996).

Antibodies include intact immunoglobulins. Antigen binding fragments are well known in the art, such as single-domain antibodies (e.g. VH domain antibodies), Fab fragments, Fab' fragments, F(ab)'$_2$ fragments, single chain Fv proteins ("scFv"), and disulfide stabilized Fv proteins ("dsFv"). A scFv protein is a fusion protein in which a light chain variable region of an immunoglobulin and a heavy chain variable region of an immunoglobulin are bound by a linker, while in dsFvs, the chains have been mutated to introduce a disulfide bond to stabilize the association of the chains. The term also includes genetically engineered forms such as chimeric antibodies (for example, humanized murine antibodies), heteroconjugate antibodies (such as, bispecific antibodies). See also, *Pierce Catalog and Handbook*, 1994-1995 (Pierce Chemical Co., Rockford, Ill.); Kuby, *J., Immunology*, 3$^{rd}$ Ed., W. H. Freeman & Co., New York, 1997.

Typically, a naturally occurring immunoglobulin has heavy (H) chains and light (L) chains interconnected by disulfide bonds. There are two types of light chain, lambda (λ) and kappa (κ). There are five main heavy chain classes (or isotypes) which determine the functional activity of an antibody molecule: IgM, IgD, IgG, IgA and IgE.

Each heavy and light chain contains a constant region and a variable region, (the regions are also known as "domains"). In combination, the heavy and the light chain variable regions specifically bind the antigen. Light and heavy chain variable regions contain a "framework" region interrupted by three hypervariable regions, also called "complementarity-determining regions" or "CDRs." The extent of the framework region and CDRs has been defined. See, for example, Kabat et al. (see, Kabat et al., *Sequences of Proteins of Immunological Interest*, U.S. Department of Health and Human Services, 1991) and ImMunoGeneTics database (IMGT) (see, Lefranc, *Nucleic Acids Res* 29:207-9, 2001; and //imgt.cines.fr/IM-GT_vquest/vquest?livret=0&Option=humanIg;). The Kabat database is now maintained online (ncbi.nlm.nih.gov/igblast/). The sequences of the framework regions of different light or heavy chains are relatively conserved within a species, such as humans. The framework region of an antibody, that is the combined framework regions of the constituent light and heavy chains, serves to position and align the CDRs in three-dimensional space.

The CDRs are primarily responsible for binding to an epitope of an antigen. The CDRs of each chain are typically referred to as CDR1, CDR2, and CDR3, numbered sequentially starting from the N-terminus, and are also typically identified by the chain in which the particular CDR is located. Thus, a $V_H$ CDR3 (or H-CDR3) is located in the variable domain of the heavy chain of the antibody in which it is found, whereas a $V_L$ CDR1 (Or L-CDR1) is the CDR1 from the variable domain of the light chain of the antibody in which it is found. An antibody that binds IGF-II, for example, will have a specific $V_H$ region and the $V_L$ region sequence, and thus specific CDR sequences. Antibodies with different specificities (i.e. different combining sites for different antigens) have different CDRs. Although it is the CDRs that vary from antibody to antibody, only a limited number of amino acid positions within the CDRs are directly involved in antigen binding. These positions within the CDRs are called specificity determining residues (SDRs).

References to "$V_H$" or "VH" refer to the variable region of an immunoglobulin heavy chain, including that of an Fv, scFv, dsFv or Fab. References to "$V_L$" or "VL" refer to the variable region of an immunoglobulin light chain, including that of an Fv, scFv, dsFv or Fab.

A "monoclonal antibody" or an "mAb" is an antibody produced by a single clone of B-lymphocytes or by a cell into which the light and heavy chain genes of a single antibody have been transfected. MAbs are produced by methods known to those of skill in the art, for instance by making hybrid antibody-forming cells from a fusion of myeloma cells with immune spleen cells. MAbs include humanized mAbs.

A "chimeric antibody" has framework residues from one species, such as human, and CDRs (which generally confer antigen binding) from another species, such as a murine antibody that specifically binds IGF-II.

A "human" antibody (also called a "fully human" antibody) is an antibody that includes human framework regions and all of the CDRs from a human immunoglobulin. In one example, the framework and the CDRs are from the same originating human heavy and/or light chain amino acid sequence. However, frameworks from one human antibody can be engineered to include CDRs from a different human antibody. A "humanized" immunoglobulin is an immunoglobulin including a human framework region and one or more CDRs from a non-human (for example a mouse, rat, or synthetic) immunoglobulin. The non-human immunoglobulin providing the CDRs is termed a "donor," and the human immunoglobulin providing the framework is termed an "acceptor." In one embodiment, all the CDRs are from the donor immunoglobulin in a humanized immunoglobulin. Constant regions need not be present, but if they are, they must be substantially identical to human immunoglobulin constant regions, i.e., at least about 85-90%, such as about 95% or more identical. Hence, all parts of a humanized immunoglobulin, except possibly the CDRs, are substantially identical to corresponding parts of natural human immunoglobulin sequences. A "humanized antibody" is an antibody comprising a humanized light chain and a humanized heavy chain immunoglobulin. A humanized antibody binds to the same antigen as the donor antibody that provides the CDRs. The acceptor framework of a humanized immunoglobulin or antibody may have a limited number of substitutions by amino acids taken from the donor framework. Humanized or other mAbs can have additional conservative amino acid substitutions which have substantially no effect on antigen binding or other immunoglobulin functions. Humanized immunoglobulins can be constructed by means of genetic engineering (see for example, U.S. Pat. No. 5,585,089).

An "engineered antibody domain," "eAd" or "single domain antibody" includes a single monomeric variable antibody domain. The variable region, in turn, comprises complimentary determining regions (CDRs) that confer binding specificity, and framework regions, which those parts of the variable domain other than the CDRs. Generally, an eAd has a molecular weight of only 12-15 kDa, and thus is smaller than a mAb with two heavy chains and two light chains (approximately 150-160 kDa) and Fab fragments (approximately 50 kDa). In one embodiment, an eAd includes a variable heavy chain domain with H-CDR1, H-CDR2 and H-CDR3, and specifically binds a target antigen, but does not include light chain CDRs or a light chain variable domain. eAds are highly expressed in microbial cell culture, show favorable biophysical properties including solubility and temperature stability, and are well suited to selection and affinity maturation by in vitro selection systems such as phage display. eAds also are bioactive as monomers and, due to their small size and inherent stability, can be formatted into larger molecules to create drugs with prolonged serum half-lives or other pharmacological activities. An eAd can include any suitable framework region and can be human or humanized Binding affinity: Affinity of an antibody for an antigen. In one embodiment, affinity is calculated by a modification of the Scatchard method described by Frankel et al., *Mol. Immunol.*, 16:101-106, 1979. In another embodiment, binding affinity is measured by an antigen/antibody dissociation rate. In another embodiment, a high binding affinity is measured by a competition radioimmunoassay. In another embodiment, binding affinity is measured by ELISA. An antibody that "specifically binds" an antigenic epitope, such as and epitope of IGF-II with a high affinity, and does not significantly bind other unrelated epitopes.

Bi-specific antibody: A recombinant molecule composed of two different antigen binding moieties and consequently binds to two different antigenic epitopes. Bi-specific antibodies include chemically or genetically linked molecules of two antigen-binding moieties. The antigen binding moieties can be linked using a linker. The antigen binding moieties can be monoclonal antibodies, antigen-binding fragments (e.g., Fab, scFv), eAds, or combinations thereof. A bispecific antibody can include one or more constant domains, but does not necessarily include a constant domain.

Chemotherapeutic agents: Any chemical agent with therapeutic usefulness in the treatment of diseases characterized by abnormal cell growth. Such diseases include tumors, neoplasms, and cancer as well as diseases characterized by hyperplastic growth such as psoriasis. In one embodiment, a chemotherapeutic agent is an agent of use in treating a lymphoma, leukemia, or another tumor. In one embodiment, a chemotherapeutic agent is a radioactive compound. One of skill in the art can readily identify a chemotherapeutic agent of use (see for example, Slapak and Kufe, *Principles of Cancer Therapy*, Chapter 86 in Harrison's Principles of Internal Medicine, 14th edition; Perry et al., *Chemotherapy, Ch.* 17 in Abeloff, Clinical Oncology $2^{nd}$ ed., © 2000 Churchill Livingstone, Inc; Baltzer, L., Berkery, R. (eds): *Oncology Pocket Guide to Chemotherapy,* 2nd ed. St. Louis, Mosby-Year Book, 1995; Fischer, D. S., Knobf, M. F., Durivage, H. J. (eds): *The Cancer Chemotherapy Handbook,* 4th ed. St. Louis, Mosby-Year Book, 1993). Combination chemotherapy is the administration of more than one agent to treat cancer. One example is the administration of an antibody that binds IGF-II or a fragment thereof used in combination with a radioactive or chemical compound.

Conservative variants: "Conservative" amino acid substitutions are those substitutions that do not substantially affect or decrease the affinity of a protein, such as an antibody to IGF-II. For example, a human antibody that specifically binds IGF-II can include at most about 1, at most about 2, at most about 5, and most about 10, or at most about 15 conservative substitutions and specifically bind the IGF-II polypeptide. The term conservative variation also includes the use of a substituted amino acid in place of an unsubstituted parent amino acid, provided that antibody specifically binds IGF-II. Non-conservative substitutions are those that reduce an activity or binding to IGF-II.

Conservative amino acid substitution tables providing functionally similar amino acids are well known to one of ordinary skill in the art. The following six groups are examples of amino acids that are considered to be conservative substitutions for one another:

1) Alanine (A), Serine (S), Threonine (T);
2) Aspartic acid (D), Glutamic acid (E);
3) Asparagine (N), Glutamine (Q);
4) Arginine (R), Lysine (K);
5) Isoleucine (I), Leucine (L), Methionine (M), Valine (V); and
6) Phenylalanine (F), Tyrosine (Y), Tryptophan (W).

Contacting: Placement in direct physical association; includes both in solid and liquid form.

Cytotoxicity: The toxicity of a molecule, such as an immunotoxin, to the cells intended to be targeted, as opposed to the cells of the rest of an organism. In one embodiment, in contrast, the term "toxicity" refers to toxicity of an immunotoxin to cells other than those that are the cells intended to be targeted by the targeting moiety of the immunotoxin, and the term "animal toxicity" refers to toxicity of the immunotoxin to an animal by toxicity of the immunotoxin to cells other than those intended to be targeted by the immunotoxin.

Degenerate variant: In the context of the present disclosure, a "degenerate variant" refers to a polynucleotide encoding a IGF-II polypeptide or an antibody that binds IGF-II that includes a sequence that is degenerate as a result of the genetic code. There are 20 natural amino acids, most of which are specified by more than one codon. Therefore, all degenerate nucleotide sequences are included as long as the amino acid sequence of the IGF-II polypeptide or antibody that binds IGF-II encoded by the nucleotide sequence is unchanged.

Diagnostic: Identifying the presence or nature of a pathologic condition, such as, but not limited to, liver cancer, ovarian cancer, melanoma or lung cancer. Diagnostic methods differ in their sensitivity and specificity. The "sensitivity" of a diagnostic assay is the percentage of diseased individuals who test positive (percent of true positives). The "specificity" of a diagnostic assay is one minus the false positive rate, where the false positive rate is defined as the proportion of those without the disease who test positive. While a particular diagnostic method may not provide a definitive diagnosis of a condition, it suffices if the method provides a positive indication that aids in diagnosis. "Prognostic" is the probability of development (e.g., severity) of a pathologic condition, such as liver cancer or metastasis.

Effector molecule: The portion of a chimeric molecule that is intended to have a desired effect on a cell to which the chimeric molecule is targeted. Effector molecule is also known as an effector moiety (EM), therapeutic agent, or diagnostic agent, or similar terms.

Therapeutic agents include such compounds as nucleic acids, proteins, peptides, amino acids or derivatives, glycoproteins, radioisotopes, lipids, carbohydrates, or recombinant viruses. Nucleic acid therapeutic and diagnostic moieties include antisense nucleic acids, derivatized oligonucleotides for covalent cross-linking with single or duplex DNA, and triplex forming oligonucleotides. Alternatively, the molecule linked to a targeting moiety, such as an anti-IGF-II antibody, may be an encapsulation system, such as a liposome or micelle that contains a therapeutic composition such as a drug, a nucleic acid (such as an antisense nucleic acid), or another therapeutic moiety that can be shielded from direct exposure to the circulatory system. Means of preparing liposomes attached to antibodies are well known to those of skill in the art (see, for example, U.S. Pat. No. 4,957,735; and Connor et al., *Pharm. Ther.* 28:341-365, 1985). Diagnostic agents or moieties include radioisotopes and other detectable labels. Detectable labels useful for such purposes are also well known in the art, and include radioactive isotopes such as $^{35}S$ $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$, fluorophores, chemiluminescent agents, and enzymes.

Epitope: An antigenic determinant. These are particular chemical groups or peptide sequences on a molecule that are antigenic, i.e. that elicit a specific immune response. An antibody specifically binds a particular antigenic epitope on a polypeptide, such as IGF-II.

Expressed: Translation of a nucleic acid into a protein. Proteins may be expressed and remain intracellular, become a component of the cell surface membrane, or be secreted into the extracellular matrix or medium.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see for example, Bitter et al., *Methods in Enzymology* 153:516-544, 1987). For example, when cloning in bacterial systems, inducible promoters such as pL of bacteriophage lambda, plac, ptrp, ptac (ptrp-lac hybrid promoter) and the like may be used. In one embodiment, when cloning in mammalian cell systems, promoters derived from the genome of mammalian cells (such as metallothionein promoter) or from mammalian viruses (such as the retrovirus long terminal repeat; the adenovirus late promoter; the vaccinia virus 7.5K promoter) can be used. Promoters produced by recombinant DNA or synthetic techniques may also be used to provide for transcription of the nucleic acid sequences.

Framework region: Amino acid sequences interposed between CDRs. Framework regions include variable light and variable heavy framework regions. The framework regions serve to hold the CDRs in an appropriate orientation for antigen binding.

HAMA (human anti-murine antibody) response: An immune response in a human subject to the variable and constant regions of a murine antibody that has been administered to the patient. Repeated antibody administration may lead to an increased rate of clearance of the antibody from the patient's serum and may also elicit allergic reactions in the patient.

Host cells: Cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used.

Immune response: A response of a cell of the immune system, such as a B cell, T cell, or monocyte, to a stimulus. In one embodiment, the response is specific for a particular antigen (an "antigen-specific response"). In one embodiment, an immune response is a T cell response, such as a $CD4^+$ response or a $CD8^+$ response. In another embodiment, the response is a B cell response, and results in the production of specific antibodies.

Immunoconjugate: A covalent linkage of an effector molecule to an antibody, antigen binding fragment thereof, eAd or bispecific antibody. The effector molecule can be a detectable label or an immunotoxin. Specific, non-limiting examples of toxins include, but are not limited to, abrin, ricin, *Pseudomonas* exotoxin (PE, such as PE35, PE37, PE38, and PE40), diphtheria toxin (DT), botulinum toxin, or modified toxins thereof, or other toxic agents that directly or indirectly inhibit cell growth or kill cells. For example, PE and DT are highly toxic compounds that typically bring about death through liver toxicity. PE and DT, however, can be modified into a form for use as an immunotoxin by removing the native targeting component of the toxin (such as the domain Ia of PE and the B chain of DT) and replacing it with a different targeting moiety, such as an antibody. A "chimeric molecule" is a targeting moiety, such as a ligand or an antibody, conjugated (coupled) to an effector molecule. The term "conjugated" or "linked" refers to making two polypeptides into one contiguous polypeptide molecule. In one embodiment, an antibody is joined to an effector molecule. In another embodiment, an antibody joined to an effector molecule is further joined to a lipid or other molecule to a protein or peptide to increase its half-life in the body. The linkage can be either by chemical or recombinant means. In one embodiment, the linkage is chemical, wherein a reaction between the antibody moiety and the effector molecule has produced a covalent bond formed between the two molecules to form one molecule. A peptide linker (short peptide sequence) can optionally be included between the antibody and the effector molecule. Because immunoconjugates were originally prepared from two molecules with separate functionalities, such as an antibody and an effector molecule, they are also sometimes referred to as "chimeric molecules." The term "chimeric molecule," as used herein, therefore refers to a targeting moiety, such as a ligand or an antibody, conjugated (coupled) to an effector molecule.

Immunogenic peptide: A peptide which comprises an allele-specific motif or other sequence, such as an N-terminal repeat, such that the peptide will bind an MHC molecule and induce a cytotoxic T lymphocyte ("CTL") response, or a B cell response (e.g. antibody production) against the antigen from which the immunogenic peptide is derived.

In one embodiment, immunogenic peptides are identified using sequence motifs or other methods, such as neural net or polynomial determinations, known in the art. Typically, algorithms are used to determine the "binding threshold" of peptides to select those with scores that give them a high probability of binding at a certain affinity and will be immunogenic. The algorithms are based either on the effects on MHC binding of a particular amino acid at a particular position, the effects on antibody binding of a particular amino acid at a particular position, or the effects on binding of a particular substitution in a motif-containing peptide. Within the context of an immunogenic peptide, a "conserved residue" is one which appears in a significantly higher frequency than would be expected by random distribution at a particular position in a peptide. In one embodiment, a conserved residue is one where the MHC structure may provide a contact point with the immunogenic peptide. In one specific non-limiting example, an immunogenic polypeptide includes a region of IGF-II, or a fragment thereof, wherein the polypeptide that is expressed on the cell surface of a host cell that expresses the full-length IGF-II polypeptide.

Immunologically reactive conditions: Includes reference to conditions which allow an antibody raised against a particular epitope to bind to that epitope to a detectably greater degree than, and/or to the substantial exclusion of, binding to substantially all other epitopes. Immunologically reactive conditions are dependent upon the format of the antibody binding reaction and typically are those utilized in immunoassay protocols or those conditions encountered in vivo. See Harlow & Lane, supra, for a description of immunoassay formats and conditions. The immunologically reactive conditions employed in the methods are "physiological conditions" which include reference to conditions (such as temperature, osmolarity, pH) that are typical inside a living mammal or a mammalian cell. While it is recognized that some organs are subject to extreme conditions, the intra-organismal and intracellular environment normally lies around pH 7 (i.e., from pH 6.0 to pH 8.0, more typically pH 6.5 to 7.5), contains water as the predominant solvent, and exists at a temperature above 0° C. and below 50° C. Osmolarity is within the range that is supportive of cell viability and proliferation.

Inhibiting or treating a disease: Inhibiting the full development of a disease or condition, for example, in a subject who is at risk for a disease such as a tumor (for example, a cancer such as breast cancer, leukemia or a carcinoma). "Treatment" refers to a therapeutic intervention that ameliorates a sign or symptom of a disease or pathological condition after it has begun to develop. As used herein, the term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of metastases, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Isolated: An "isolated" biological component, such as a nucleic acid, protein (including antibodies) or organelle, has been substantially separated or purified away from other biological components in the environment (such as a cell) in which the component naturally occurs, i.e., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids. In some embodiments, the biological component is at least 95%, 96%, 97%, 98% or 99% pure.

Label: A detectable compound or composition that is conjugated directly or indirectly to another molecule, such as an antibody or a protein, to facilitate detection of that molecule. Specific, non-limiting examples of labels include fluorescent tags, enzymatic linkages, and radioactive isotopes. In one example, a "labeled antibody" refers to incorporation of another molecule in the antibody. For example, the label is a detectable marker, such as the incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Various methods of labeling polypeptides and glycoproteins are known in the art and may be used. Examples of labels for polypeptides include, but are not limited to, the following: radioisotopes or radionucleotides (such as $^{35}S$ $^{11}C$, $^{13}N$, $^{15}O$, $^{18}F$, $^{19}F$, $^{99m}Tc$, $^{131}I$, $^{3}H$, $^{14}C$, $^{15}N$, $^{90}Y$, $^{99}Tc$, $^{111}In$ and $^{125}I$), fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

Linker: In some cases, a linker is a peptide, such as within an antibody binding fragment (such as an Fv fragment), which serves to indirectly bond the variable heavy chain to the variable light chain. "Linker" can also refer to a peptide serving to link a targeting moiety, such as an antibody, to an effector molecule, such as a cytotoxin or a detectable label, or that links and eAd to a mAb or antigen binding fragment thereof.

The terms "conjugating," "joining," "bonding" or "linking" refer to making two polypeptides into one contiguous polypeptide molecule, or to covalently attaching a radionuclide or other molecule to a polypeptide, such as an scFv. In the specific context, the terms include reference to joining a ligand, such as an antibody moiety, to an effector molecule. The linkage can be either by chemical or recombinant means. "Chemical means" refers to a reaction between the antibody moiety and the effector molecule such that there is a covalent bond formed between the two molecules to form one molecule.

Mammal: This term includes both human and non-human mammals. Similarly, the term "subject" includes both human and veterinary subjects.

Neoplasia, malignancy, cancer or tumor: A neoplasm is an abnormal growth of tissue or cells that results from excessive cell division. Neoplastic growth can produce a tumor. The amount of a tumor in an individual is the "tumor burden" which can be measured as the number, volume, or weight of the tumor. A tumor that does not metastasize is referred to as "benign." A tumor that invades the surrounding tissue and/or can metastasize is referred to as "malignant." Examples of hematological tumors include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Examples of solid tumors, such as sarcomas and carcinomas, include fibrosarcoma, myxosarcoma, liposarcoma, chondrosarcoma, osteogenic sarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). In several examples, a tumor is breast cancer.

Nucleic acid: A polymer composed of nucleotide units (ribonucleotides, deoxyribonucleotides, related naturally occurring structural variants, and synthetic non-naturally occurring analogs thereof) linked via phosphodiester bonds, related naturally occurring structural variants, and synthetic non-naturally occurring analogs thereof. Thus, the term includes nucleotide polymers in which the nucleotides and the linkages between them include non-naturally occurring synthetic analogs, such as, for example and without limitation, phosphorothioates, phosphoramidates, methyl phosphonates, chiral-methyl phosphonates, 2-O-methyl ribonucleotides, peptide-nucleic acids (PNAs), and the like. Such polynucleotides can be synthesized, for example, using an automated DNA synthesizer. The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe nucleotide sequences: the left-hand end of a single-stranded nucleotide sequence is the 5'-end; the left-hand direction of a double-stranded nucleotide sequence is referred to as the 5'-direction. The direction of 5' to 3' addition of nucleotides to nascent RNA transcripts is referred to as the transcription direction. The DNA strand having the same sequence as an mRNA is referred to as the "coding strand;" sequences on the DNA strand having the same sequence as an mRNA transcribed from that DNA and which are located 5' to the 5'-end of the RNA transcript are referred to as "upstream sequences;" sequences on the DNA strand having the same sequence as the RNA and which are 3' to the 3' end of the coding RNA transcript are referred to as "downstream sequences."

"cDNA" refers to a DNA that is complementary or identical to an mRNA, in either single stranded or double stranded form.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant nucleic acid" refers to a nucleic acid having nucleotide sequences that are not naturally joined together. This includes nucleic acid vectors comprising an amplified or assembled nucleic acid which can be used to transform a suitable host cell. A host cell that comprises the recombinant nucleic acid is referred to as a "recombinant host cell." The gene is then expressed in the recombinant host cell to produce, such as a "recombinant polypeptide." A recombinant nucleic acid may serve a non-coding function (such as a promoter, origin of replication, ribosome-binding site, etc.) as well.

A first sequence is an "antisense" with respect to a second sequence if a polynucleotide whose sequence is the first sequence specifically hybridizes with a polynucleotide whose sequence is the second sequence.

Terms used to describe sequence relationships between two or more nucleotide sequences or amino acid sequences include "reference sequence," "selected from," "comparison window," "identical," "percentage of sequence identity," "substantially identical," "complementary," and "substantially complementary."

For sequence comparison of nucleic acid sequences, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters are used. Methods of alignment of sequences for comparison are well known in the art. Optimal alignment of sequences for comparison can be conducted, for example, by the local homology algorithm of Smith & Waterman, *Adv. Appl. Math.* 2:482, 1981, by the homology alignment algorithm of Needleman & Wunsch, *J. Mol. Biol.* 48:443, 1970, by the search for similarity method of Pearson & Lipman, *Proc. Nat'l. Acad. Sci. USA* 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see for example, *Current Protocols in Molecular Biology* (Ausubel et al., eds 1995 supplement)).

One example of a useful algorithm is PILEUP. PILEUP uses a simplification of the progressive alignment method of Feng & Doolittle, *J. Mol. Evol.* 35:351-360, 1987. The method used is similar to the method described by Higgins & Sharp, *CABIOS* 5:151-153, 1989. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, such as version 7.0 (Devereaux et al., *Nuc. Acids Res.* 12:387-395, 1984.

Another example of algorithms that are suitable for determining percent sequence identity and sequence similarity are the BLAST and the BLAST 2.0 algorithm, which are described in Altschul et al., *J. Mol. Biol.* 215:403-410, 1990 and Altschul et al., *Nucleic Acids Res.* 25:3389-3402, 1977. Software for performing BLAST analyses is publicly available through the National Center for Biotechnology Information (ncbi.nlm.nih.gov/). The BLASTN program (for nucleotide sequences) uses as defaults a word length (W) of 11, alignments (B) of 50, expectation (E) of 10, M=5, N=−4, and a comparison of both strands. The BLASTP program (for amino acid sequences) uses as defaults a word length (W) of 3, and expectation (E) of 10, and the BLOSUM62 scoring matrix (see Henikoff & Henikoff, *Proc. Natl. Acad. Sci. USA* 89:10915, 1989).

Operably linked: A first nucleic acid sequence is operably linked with a second nucleic acid sequence when the first nucleic acid sequence is placed in a functional relationship with the second nucleic acid sequence. For instance, a promoter, such as the CMV promoter, is operably linked to a coding sequence if the promoter affects the transcription or expression of the coding sequence. Generally, operably linked DNA sequences are contiguous and, where necessary to join two protein-coding regions, in the same reading frame.

Peptide: A chain of amino acids of between 3 and 30 amino acids in length. In one embodiment, a peptide is from about 10 to about 25 amino acids in length. In yet another embodiment, a peptide is from about 11 to about 20 amino acids in length. In yet another embodiment, a peptide is about 9 to 12 amino acids in length.

An "IGF-II peptide" is a series of contiguous amino acid residues from an IGF-II protein. In one example, with respect to immunogenic compositions comprising an IGF-II peptide, the term further refers to variations of these peptides in which there are conservative substitutions of amino acids, so long as the variations do not alter by more than about 20% (such as no more than about 1%, about 5%, or about 10%) the ability of the peptide to produce a B cell response, or, when bound to a Major Histocompatibility Complex Class 1 molecule, to activate cytotoxic T lymphocytes against cells expressing wild-type IGF-II protein. Induction of CTLs using synthetic peptides and CTL cytotoxicity assays are taught in, for example, U.S. Pat. No. 5,662,907.

Peptide modifications: Polypeptides, such as IGF-II polypeptides, include synthetic embodiments of peptides described herein. In addition, analogs (non-peptide organic molecules), derivatives (chemically functionalized peptide molecules obtained starting with the disclosed peptide sequences) and variants (homologs) of these proteins can be utilized in the methods described herein. Each polypeptide is comprised of a sequence of amino acids, which may be either L- and/or D-amino acids, naturally occurring and otherwise.

Peptides may be modified by a variety of chemical techniques to produce derivatives having essentially the same activity as the unmodified peptides, and optionally having other desirable properties. For example, carboxylic acid groups of the protein, whether carboxyl-terminal or side chain, may be provided in the form of a salt of a pharmaceutically-acceptable cation or esterified to form a $C_1$-$C_{16}$ ester, or converted to an amide of formula $NR_1R_2$ wherein $R_1$ and $R_2$ are each independently H or $C_1$-$C_{16}$ alkyl, or combined to form a heterocyclic ring, such as a 5- or 6-membered ring. Amino groups of the peptide, whether amino-terminal or side chain, may be in the form of a pharmaceutically-acceptable acid addition salt, such as HCl, HBr, acetic, benzoic, toluene sulfonic, maleic, tartaric and other organic salts, or may be modified to $C_1$-$C_{16}$ alkyl or dialkyl amino or further converted to an amide.

Hydroxyl groups of the peptide side chains may be converted to $C_1$-$C_{16}$ alkoxy or to a $C_1$-$C_{16}$ ester using well-recognized techniques. Phenyl and phenolic rings of the peptide side chains may be substituted with one or more halogen atoms, such as fluorine, chlorine, bromine or iodine, or with $C_1$-$C_{16}$ alkyl, $C_1$-$C_{16}$ alkoxy, carboxylic acids and esters thereof, or amides of such carboxylic acids. Methylene groups of the peptide side chains can be extended to homologous $C_2$-$C_4$ alkylenes. Thiols can be protected with any one of a number of well-recognized protecting groups, such as acetamide groups. Those skilled in the art will also recognize methods for introducing cyclic structures into the IGF-II peptides to select and provide conformational constraints to the structure that result in enhanced stability.

Peptidomimetic and organomimetic embodiments are envisioned, whereby the three-dimensional arrangement of the chemical constituents of such peptido- and organomimetics mimic the three-dimensional arrangement of the peptide backbone and component amino acid side chains, resulting in such peptido- and organomimetics of a IGF-II polypeptide having measurable or enhanced ability to generate an immune response. For computer modeling applications, a pharmacophore is an idealized, three-dimensional definition of the structural requirements for biological activity. Peptido- and organomimetics can be designed to fit each pharmacophore with current computer modeling software (using computer assisted drug design or CADD). See Walters, "Computer-Assisted Modeling of Drugs", in Klegerman & Groves, eds., 1993, *Pharmaceutical Biotechnology*, Interpharm Press, Buffalo Grove, Ill., pp. 165-174 and *Principles of Pharmacology* Munson (ed.) 1995, Ch. 102, for descriptions of techniques used in CADD. Also included are mimetics prepared using such techniques.

Pharmaceutical agent: A chemical compound or composition capable of inducing a desired therapeutic or prophylactic effect when properly administered to a subject or a cell.

Pharmaceutically acceptable carriers: The pharmaceutically acceptable carriers of use are conventional. *Remington's Pharmaceutical Sciences*, by E. W. Martin, Mack Publishing Co., Easton, Pa., 15th Edition, 1975, describes compositions and formulations suitable for pharmaceutical delivery of the antibodies herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop, such as a reduction in tumor burden or a decrease in the number of size of metastases. "Ameliorating" refers to the reduction in the number or severity of signs or symptoms of a disease, such as cancer.

Promoter: A promoter is an array of nucleic acid control sequences that directs transcription of a nucleic acid. A promoter includes necessary nucleic acid sequences near the start site of transcription, for example, in the case of a polymerase II type promoter, a TATA element. A promoter also optionally includes distal enhancer or repressor elements which can be located as much as several thousand base pairs from the start site of transcription. Both constitutive and inducible promoters are included (see for example, Bitter et al., *Methods in Enzymology* 153:516-544, 1987).

Specific, non-limiting examples of promoters include promoters derived from the genome of mammalian cells (such as the metallothionein promoter) or from mammalian viruses (such as the retrovirus long terminal repeat; the adenovirus late promoter; the vaccinia virus 7.5K promoter) may be used. Promoters produced by recombinant DNA or synthetic techniques may also be used. A polynucleotide can be inserted into an expression vector that contains a promoter sequence which facilitates the efficient transcription of the inserted genetic sequence of the host. The expression vector typically contains an origin of replication, a promoter, as well as specific nucleic acid sequences that allow phenotypic selection of the transformed cells.

Purified: The term purified does not require absolute purity; rather, it is intended as a relative term. Thus, for example, a purified peptide preparation is one in which the peptide or protein is more enriched than the peptide or protein is in its natural environment within a cell. In one embodiment, a preparation is purified such that the protein or peptide represents at least 50% of the total peptide or protein content of the preparation.

The IGF-II polypeptides disclosed herein, or antibodies that specifically bind IGF-II, can be purified by any of the means known in the art. See for example *Guide to Protein Purification*, ed. Deutscher, *Meth. Enzymol.* 185, Academic Press, San Diego, 1990; and Scopes, *Protein Purification: Principles and Practice*, Springer Verlag, New York, 1982. Substantial purification denotes purification from other proteins or cellular components. A substantially purified protein is at least 60%, 70%, 80%, 90%, 95% or 98% pure. Thus, in one specific, non-limiting example, a substantially purified protein is 90% free of other proteins or cellular components.

Recombinant: A recombinant nucleic acid is one that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques.

Recombinant toxins: Chimeric proteins in which a cell targeting moiety is fused to a toxin (Pastan et al., *Science*, 254:1173-1177, 1991). If the cell targeting moiety is the Fv portion of an antibody, the molecule is termed a recombinant immunotoxin (Chaudhary et al., *Nature*, 339:394-397, 1989). The toxin moiety is genetically altered so that it cannot bind to the toxin receptor present on most normal cells. Recombinant immunotoxins selectively kill cells which are recognized by the antigen binding domain. These recombinant toxins and immunotoxins can be used to treat cancer, for example, a cancer in which IGF-II is expressed.

Sample (or biological sample): A biological specimen containing genomic DNA, RNA (including mRNA), protein, or combinations thereof, obtained from a subject. Examples include, but are not limited to, peripheral blood, tissue, cells, urine, saliva, tissue biopsy, fine needle aspirate, surgical specimen, and autopsy material. In one example, a sample includes a HCC tissue biopsy.

Sequence identity: The similarity between amino acid or nucleic acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of a polypeptide or nucleic acid molecule will possess a relatively high degree of sequence identity when aligned using standard methods.

Methods of alignment of sequences for comparison are well known in the art. Various programs and alignment algorithms are described in: Smith and Waterman, *Adv. Appl. Math.* 2:482, 1981; Needleman and Wunsch, *J. Mol. Biol.* 48:443, 1970; Pearson and Lipman, *Proc. Natl. Acad. Sci. U.S.A.* 85:2444, 1988; Higgins and Sharp, *Gene* 73:237, 1988; Higgins and Sharp, *CABIOS* 5:151, 1989; Corpet et al., *Nucleic Acids Research* 16:10881, 1988; and Pearson and Lipman, *Proc. Natl. Acad. Sci. U.S.A.* 85:2444, 1988. Altschul et al., *Nature Genet.* 6:119, 1994, presents a detailed consideration of sequence alignment methods and homology calculations.

The NCBI Basic Local Alignment Search Tool (BLAST) (Altschul et al., *J. Mol. Biol.* 215:403, 1990) is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of a $V_L$ or a $V_H$ of an antibody that specifically binds a IGF-II polypeptide are typically characterized by possession of at least about 75%, for example at least about 80%, 90%, 95%, 96%, 97%, 98% or 99% sequence identity counted over the full length alignment with the amino acid sequence of the antibody using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and may possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Specific binding agent: An agent that binds substantially only to a defined target. Thus an IGF-II specific binding agent is an agent that binds substantially to an IGF-II polypeptide. In one embodiment, the specific binding agent is a human mAb, antigen binding fragment thereof, eAd or bispecific antibody that specifically binds the IGF-II polypeptide.

The term "specifically binds" refers, with respect to an antigen such as IGF-II, to the preferential association of an antibody or other ligand, in whole or part, with a cell or tissue bearing that antigen and not to cells or tissues lacking that antigen. It is, of course, recognized that a certain degree of non-specific interaction may occur between a molecule and a non-target cell or tissue. Nevertheless, specific binding may be distinguished as mediated through specific recognition of the antigen. Although selectively reactive antibodies bind antigen, they may do so with low affinity. On the other hand, specific binding results in a much stronger association between the antibody (or other ligand) and cells bearing the antigen than between the bound antibody (or other ligand) and cells lacking the antigen. Specific binding typically results in greater than 2-fold, such as greater than 5-fold, greater than 10-fold, or greater than 100-fold increase in amount of bound antibody or other ligand (per unit time) to a cell or tissue bearing the IGF-II polypeptide as compared to a cell or tissue lacking the polypeptide. Specific binding to a protein under such conditions requires an antibody that is selected for its specificity for a particular protein. A variety of immunoassay formats are appropriate for selecting antibodies or other ligands specifically immunoreactive with a particular protein. For example, solid-phase ELISA immunoassays are routinely used to select mAbs specifically immunoreactive with a protein. See Harlow & Lane, *Antibodies, A Laboratory Manual*, Cold Spring Harbor Publications, New York (1988), for a description of immunoassay formats and conditions that can be used to determine specific immunoreactivity.

Subject: Living multi-cellular vertebrate organisms, a category that includes both human and veterinary subjects, including human and non-human mammals.

Therapeutically effective amount: A quantity of a specific substance sufficient to achieve a desired effect in a subject being treated. For instance, this can be the amount necessary to inhibit or suppress growth of a tumor. In one embodiment, a therapeutically effective amount is the amount necessary to eliminate, reduce the size, or prevent metastasis of a tumor. When administered to a subject, a dosage will generally be used that will achieve target tissue concentrations (for example, in tumors) that has been shown to achieve a desired in vitro effect.

Toxin: A molecule that is cytotoxic for a cell. Toxins include abrin, ricin, *Pseudomonas* exotoxin (PE), diphtheria toxin (DT), botulinum toxin, saporin, restrictocin or gelonin, or modified toxins thereof. For example, PE and DT are highly toxic compounds that typically bring about death through liver toxicity. PE and DT, however, can be modified into a form for use as an immunotoxin by removing the native targeting component of the toxin (such as domain Ia of PE or the B chain of DT) and replacing it with a different targeting moiety, such as an antibody.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. Hence "comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. All GEN-BANK® Accession numbers are herein incorporated by reference as they appear in the database on Sep. 5, 2011. In case of conflict, the present specification, including explanations of terms, will control. In addition, the materials, methods, and examples are illustrative only and not intended to be limiting.

Monoclonal Antibodies, Antigen Binding Fragments, Engineered Antibody Domains and Bispecific Antibodies The two ligands of the insulin like growth factor (IGF) system, IGF-I and IGF-II, are single-chain polypeptides sharing 62% homology with proinsulin. The degree of homology between human and mouse IGF-I is 97%, while the degree of homology between human and mouse IGF-II is 91%. Amino acid sequences of mammalian IGF-I and IGF-II, such as the mouse and human proteins, are available on the internet through GENBANK®, see for example GENBANK® Accession No. CAA00082 (human IGF-II, Jan. 28, 1993), AAB21519 (human IGF-II, May 17, 2002), NP_034644 (mouse IGF-II, updated Aug. 6, 2006) NP_034642 (mouse IGF-I, updated Aug. 6, 2006), which are incorporated herein by reference. The amino acid sequence of the IR is available through GENBANK®, see Accession Nos. P6213 (Jan. 1, 1998) and NP000199 (Apr. 19, 2006), both incorporated herein by reference. MAbs, antigen binding fragments thereof, eAds and bispecific antibodies are disclosed herein that specifically bind IGF-II.

Binding of IGFs to IGF-IR activates its intracellular tyrosine kinase domain, which results in autophosphorylation of the receptor. This in turn results in activation of various pathways that serve to increase cell proliferation, cell motility, and protection from apoptosis. IGF-IR has been linked to increased growth, survival, and oncogenic transformation of cancer cells (Kaleko et al., *Mol Cell Biol* 10:464-473, 1990; Baserga et al., *Biochim Biophys Acta* 1332:F105-F126, 1997; Blakesley et al., *J Endocrinol* 152:339-344, 1997; Khandwala et al., *Endocr Rev* 21:215-244, 2000), and overexpression of IGF-IR has been observed in a variety of tumor types (Bergmann et al., *Cancer Res* 55:2007-2011, 1995; Werner et al., *Adv Cancer Res* 68:183-223, 1996; Happerfield et al., *J Pathol* 183:412-417, 1997; Xie et al., *Cancer Res* 59:3588-3591, 1999; Khandwala et al., *Endocr Rev* 21:215-244, 2000; Hellawell et al., *Cancer Res* 62:2942-2950, 2002; Weber et al., *Cancer* 95:2086-2095, 2002). The ligands of IGF-IR, IGF-I and IGF-II, are known to functions as mitogens in a variety of cancer cell lines (Cullen et al., *Cancer Res* 50:48-53, 1990; Ankrapp et al., *Cancer Res* 53:3399-3404, 1993; Kappel et al., *Cancer Res* 54:2803-2807 1994; Guo et al., *J Am Coll Surg* 181:145-154, 1995; Steller et al., *Cancer Res* 56:1761-1765, 1996; Hermanto et al., *Cell Growth Differ* 11:655-664, 2000). Many tumors overexpress the IGF-II ligand (Werner et al., *Adv Cancer Res* 68:183-223, 1996), exhibiting IGF-II expression levels several fold higher than those of IGF-I. Antibodies to IGF proteins have been shown to decrease cell proliferation, increase apoptosis, and reduce tumor cell growth and metastasis (Fitzsimmons et al., *Endocrinology* 136:3100-3106, 1995; Goya, Cancer Res 64:6252-6258 2004; Miyamoto, *Clin Cancer Res* 11:3494-3502, 2005).

Disclosed herein are mAbs, antigen binding fragment thereof, bispecific antibodies and/or eAds that bind IGF-II with an equilibrium constant ($K_d$) of 1 nM or less. In another example, the antibodies bind insulin-like growth factor II (IGF-II) with an equilibrium association constant ($K_d$) of 1 nM or less, wherein the antibodies bind IGF-I with an equilibrium association constant ($K_d$) of 1 µM or greater, and wherein the antibodies inhibits phosphorylation of the IGF-IR. In additional embodiments, the antibodies inhibit the phosphorylation of the IR. In several embodiments, the mAbs bind human IGF-II with a binding affinity of $0.1 \times 10^{-8}$ M, at least about $0.3 \times 10^{-8}$ M, at least about $0.5 \times 10^{-8}$ M, at least about $0.75 \times 10^{-8}$ M, at least about $1.0 \times 10^{-8}$ M, at least about $1.3 \times 10^{-8}$ M at least about $1.5 \times 10^{-8}$ M, or at least about $2.0 \times 10^{-8}$ M.

In several embodiments, the mAb, bispecific antibody, antigen binding fragment or an eAd includes the heavy chain variable region of the m610.27 (m610.27 $V_H$) amino acid sequence:

```
                                              (SEQ ID NO: 1)
QVQLVQSGAEVKKPGASVKVSCKASGYTFTSYYMHWVRQAPGQGLEW

MGIINPSGGSTSYAQKFQGRVTMTRDTSTSTVYMELSRLRSDDTAVYYCA

RDVQWLAYGMDVWGQGTTVTVSS.
```

Thus, in some embodiments, the heavy chain of the antibody includes one or more of amino acids 26-33 of SEQ ID NO: 1, amino acids 51-58 of SEQ ID NO: 1, and amino acids 97-109 of SEQ ID NO: 1, and specifically binds IGF-II. In additional embodiments, the heavy chain variable domain of the antibody includes amino acids 26-33 of SEQ ID NO: 1, amino acids 51-58 of SEQ ID NO: 1, and amino acids 97-109 of SEQ ID NO: 1, and specifically binds IGF-II. In further embodiments, the antibody includes the amino acid sequence set forth as SEQ ID NO: 1.

In additional embodiments, the mAb, antigen binding fragment, eAd, bispecific antibody, or antigen binding fragment includes the light chain variable region m610.27 $V_L$ amino acid sequence:

(SEQ ID NO: 2)
DIQMTQSPSSLSASVGDRVTITCRASQSISSYLNWYQQKPGRAPDLLINA

ASSLQSGVPSRFSGSGSGTDFTLTISSLQPEDFATYFCQQSYSLPFTFGG

GTKVEIKG.

Thus, in some embodiments, the light chain of the antibody includes at least one of amino acids 27-32 of SEQ ID NO: 2, amino acids 50-52 of SEQ ID NO: 2, and amino acids 89-98 of SEQ ID NO: 2, and specifically binds IGF-II. In additional embodiments, the light chain variable domain of the antibody includes amino acids 27-32 of SEQ ID NO: 2, amino acids 50-52 of SEQ ID NO: 2, and amino acids 89-98 of SEQ ID NO: 2, and specifically binds IGF-II. In further embodiments, the antibody includes the amino acid sequence set forth as SEQ ID NO: 2.

In some embodiments, a heavy chain of the mAb, antigen binding fragment or bispecific antibody that specifically binds IGF-II includes a heavy chain comprising amino acids 26-33 of SEQ ID NO: 1, amino acids 51-58 of SEQ ID NO: 1, and amino acids 97-109 of SEQ ID NO: 1, and a light chain comprising amino acids 27-32 of SEQ ID NO: 2, amino acids 50-52 of SEQ ID NO: 2, and amino acids 89-98 of SEQ ID NO: 2. In additional embodiments, a heavy chain of the mAb, antigen binding fragment or bispecific antibody that specifically binds IGF-II includes a heavy chain comprising the amino acid sequence set forth as SEQ ID NO: 1, and a light chain comprising the amino acid sequence set forth as SEQ ID NO: 2.

The mAb can be of any isotype. The mAb can be, for example, an IgM or an IgG antibody, such as $IgG_1$ or an $IgG_2$. The class of an antibody that specifically binds IGF-II can be switched with another. In one aspect, a nucleic acid molecule encoding $V_L$ or $V_H$ is isolated using methods well-known in the art, such that it does not include any nucleic acid sequences encoding the constant region of the light or heavy chain, respectively. The nucleic acid molecule encoding $V_L$ or $V_H$ is then operatively linked to a nucleic acid sequence encoding a $C_L$ or $C_H$ from a different class of immunoglobulin molecule. This can be achieved using a vector or nucleic acid molecule that comprises a $C_L$ or $C_H$ chain, as known in the art. For example, an antibody that specifically binds IGF-II that was originally IgM may be class switched to an IgG. Class switching can be used to convert one IgG subclass to another, such as from $IgG_1$ to $IgG_2$.

In some embodiments, the mAb, or a bispecific antibody, includes a heavy chain constant domain comprising, or consisting of, the amino acid sequence set forth as SEQ ID NO: 3:

(SEQ ID NO: 3)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKKVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSRDELTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

In some embodiments, the mAb, or bispecific antibody, includes a light chain constant domain comprising, or consisting of the amino acid sequence set forth as SEQ ID NO: 4:

(SEQ ID NO: 4)
GTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

Fully human mAbs include a human framework region. This human framework region can be the framework regions in SEQ ID NO: 1, SEQ ID NO: 2 or SEQ ID NO: 5 (these sequences include CDR sequences as well as framework sequences). However, the framework regions can be from another source.

Antibody fragments are encompassed by the present disclosure, such as Fab, F(ab')$_2$, and Fv which include a heavy chain and light chain variable region and are capable of binding the epitopic determinant on IGF-II. These antibody fragments retain the ability to selectively bind with the antigen. The fragments can be included in a bispecific antibody. These antigen binding fragments include:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', the fragment of an antibody molecule can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')$_2$ is a dimer of two Fab' fragments held together by two disulfide bonds;

(4) Fv, a genetically engineered fragment containing the variable region of the light chain and the variable region of the heavy chain expressed as two chains; and (5) Single chain antibody (such as scFv), defined as a genetically engineered molecule containing the variable region of the light chain, the variable region of the heavy chain, linked by a suitable polypeptide linker as a genetically fused single chain molecule.

(6) A dimer of a single chain antibody (scFV$_2$), defined as a dimer of an scFV. This has also been termed a "minantibody."

Methods of making these fragments are known in the art (see for example, Harlow and Lane, *Antibodies: A Laboratory Manual*, Cold Spring Harbor Laboratory, New York, 1988). In several examples, the variable region included in the antibody is the variable region of m610.27. In one group of embodiments, the antibodies have $V_H$ CDRsm610.27, or a combination of these CDRs, as discussed above.

In a further group of embodiments, the antibodies are Fv antibodies, which are typically about 25 kDa and contain a complete antigen-binding site with three CDRs per each heavy chain and each light chain. To produce these antibodies, the $V_H$ and the $V_L$ can be expressed from two individual nucleic acid constructs in a host cell. If the $V_H$ and the $V_L$ are expressed non-contiguously, the chains of the Fv antibody are typically held together by noncovalent interactions. However, these chains tend to dissociate upon dilution, so methods have been developed to crosslink the chains through glutaraldehyde, intermolecular disulfides, or a peptide linker. Thus, in one example, the Fv can be a disulfide stabilized Fv (dsFv), wherein the heavy chain variable region and the light chain variable region are chemically linked by disulfide bonds.

In an additional example, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing scFvs are known in the art (see Whitlow et al., *Methods: a Companion to Methods in Enzymology*, Vol. 2, page 97, 1991; Bird et al., *Science* 242: 423, 1988; U.S. Pat. No. 4,946,778; Pack et al., *Bio/Technology* 11:1271, 1993; and Sandhu, supra). Dimers of a single chain antibody (scFV$_2$), are also contemplated.

Antibody fragments can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see U.S. Pat. No. 4,036,945 and U.S. Pat. No. 4,331,647, and references contained therein; Nisonhoff et al., *Arch. Biochem. Biophys.* 89:230, 1960; Porter, *Biochem. J.* 73:119, 1959; Edelman et al., *Methods in Enzymology*, Vol. 1, page 422, Academic Press, 1967; and Coligan et al. at sections 2.8.1-2.8.10 and 2.10.1-2.10.4).

Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

One of skill will realize that conservative variants of the antibodies can be produced. Such conservative variants employed in antibody fragments, such as dsFv fragments or in scFv fragments, will retain critical amino acid residues necessary for correct folding and stabilizing between the $V_H$ and the $V_L$ regions, and will retain the charge characteristics of the residues in order to preserve the low pI and low toxicity of the molecules. Amino acid substitutions (such as at most one, at most two, at most three, at most four, or at most five amino acid substitutions) can be made in the $V_H$ and the $V_L$ regions to increase yield. Conservative amino acid substitution tables providing functionally similar amino acids are well known to one of ordinary skill in the art (see above). Thus, one of skill in the art can readily review the sequences shown above, identify a conservative substitution, and produce the conservative variant using well-known molecular techniques.

EAds and bispecific antibodies comprising an eAd are provided herein. The eAd, or bispecific antibody can include the CDRs or the variable domain of the following amino acid sequence:
QVQLVQSGGGLVQPGGSLRLSCAASS<u>FDFX$_1$YYEMS</u>WVRQAPGQRLEWVA <u>YISKSGGTKMYADSVKGRF</u>TISRDNSX$_2$NTLYLQMNTLRAEDTAMYYC
<u>AKDRATCX$_3$GGX$_4$CYSFYX$_5$GMDV</u>WGQGTLVTVSS (SEQ ID NO: 5, wherein X$_1$ is D or G, X$_2$ is K or R, X$_3$ is S or R, X$_4$ is S or R, and X$_5$ is Y or H and wherein the CDR sequences are underlined).

In some embodiments, the eAd, or bispecific antibody comprises the CDRs or the variable domain of the following amino acid sequence (m630, see FIG. 1): QVQLVQSGGGLVQPGGSLRLSCAASS<u>FDFDYYEMS</u>WVRQAPGQRLEWVAY <u>ISKSGGTKMYADSVKGRF</u>TISRDNSKNTLYLQMNTLRAEDTAMYYC
<u>AKDRATCSGGSCYSFYYGMDV</u>WGQGTLVTVSS (SEQ ID NO: 5, wherein X$_1$ is D, X$_2$ is K, X$_3$ is S, X$_4$ is S, and X$_5$ is Y and wherein the CDR sequences are underlined).

In other embodiments, the eAd or bispecific antibody comprises the CDRs or the variable domain of the following amino acid sequence (m630.1, see FIG. 1): QVQLVQSGGGLVQPGGSLRLSCAASS<u>FDFDYYEMS</u>WVRQAPGQRLEWVAY <u>ISKSGGTKMYADSVKGRF</u>TISRDNSRNTLYLQMNTLRAEDTAMYYC
<u>AKDRATCRGGSCYSFYHGMDV</u>WGQGTLVTVSS (SEQ ID NO: 5, wherein X$_1$ is D, X$_2$ is R, X$_3$ is R, X$_4$ is S, and X$_5$ is H and wherein the CDR sequences are underlined).

In some embodiments, the eAd or bispecific antibody comprises the CDRs or the variable domain of the following amino acid sequence (m630.3, see FIG. 1): QVQLVQSGGGLVQPGGSLRLSCAASS<u>FDFDYYEMS</u>WVRQAPGQRLEWVAY <u>ISKSGGTKMYADSVKGRF</u>TISRDNSKNTLYLQMNTLRAEDTAMYYC
<u>AKDRATCRGGRCYSFYYGMDV</u>WGQGTLVTVSS (SEQ ID NO: 5, wherein X$_1$ is D, X$_2$ is K, X$_3$ is R, X$_4$ is R, and X$_5$ is Y and wherein the CDR sequences are underlined).

In additional embodiments, the eAd, or bispecific antibody comprises the CDRs or the variable domain of the following amino acid sequence (m630.4, see FIG. 1): QVQLVQSGGGLVQPGGSLRLSCAASS<u>FDFGYYEMS</u>WVRQAPGQRLEWVAY <u>ISKSGGTKMYADSVKGRF</u>TISRDNSKNTLYLQMNTLRAEDTAMYY
C<u>AKDRATCSGGRCYSFYYGMDV</u>WGQGTLVTVSS (SEQ ID NO: 5, wherein X$_1$ is G, X$_2$ is K, X$_3$ is S, X$_4$ is R, and X$_5$ is Y and wherein the CDR sequences are underlined).

In more embodiments, the eAd, or bispecific antibody comprises the CDRs or the variable domain of the following amino acid sequence (m630.9, see FIG. 1): QVQLVQSGGGLVQPGGSLRLSCAASS<u>FDFDYYEMS</u>WVRQAPGQRLEWVAY <u>ISKSGGTKMYADSVKGRF</u>TISRDNSKNTLYLQMNTLRAEDTAMYYC
<u>AKDRATCSGGRCYSFYYGMDV</u>WGQGTLVTVSS (SEQ ID NO: 5, wherein X$_1$ is D, X$_2$ is K, X$_3$ is S, X$_4$ is R, and X$_5$ is Y and wherein the CDR sequences are underlined).

Thus, in some embodiments, the eAd or bispecific antibody includes one or more of amino acids 26-33 of SEQ ID NO: 5, amino acids 51-58 of SEQ ID NO: 5, and amino acids 97-117 of SEQ ID NO: 5, and specifically binds IGF-II. In additional embodiments, the eAd or bispecific antibody includes amino acids 26-33 of SEQ ID NO: 5, amino acids 51-58 of SEQ ID NO: 5, and amino acids 97-109 of SEQ ID NO: 5, and specifically binds IGF-II. In further embodiments, the eAd or bispecific antibody includes the amino acid sequence set forth as SEQ ID NO: 5. In specific non-limiting examples, the eAd or bispecific antibody can include amino acids 26-33 of SEQ ID NO: 5, amino acids 51-58 of SEQ ID NO: 5, and/or amino acids 97-117 of SEQ ID NO: 5, wherein (a) X$_1$ is a D, X$_2$ is a K, X$_3$ is S, X$_4$ is S, and X$_5$ is Y (m630); (b) X$_1$ is D, X$_2$ is a R, X$_3$ is R, X$_4$ is S, and X$_5$ is H (m630.1); (c) wherein X$_1$ is D, X$_2$ is a K, X$_3$ is R, X$_4$ is R, and X$_5$ is Y (m630.3); (d) X$_1$ is G, X$_2$ is a K, X$_3$ is S, X$_4$ is R, and X$_5$ is Y (m630.4); or (e) X$_1$ is D, X$_2$ is a K, X$_3$ is S, X$_4$ is R, and X$_5$ is Y (m630.9).

An eAd can be attached to a constant domain, such as an IgG or an IgM constant domain. An exemplary construct is illustrated in FIG. 2B. Suitable constant domains are disclosed, for example, as SEQ ID NO: 3 and SEQ ID NO: 4. In one specific non-limiting example, a fusion of m630.3 and a constant domain is produced. For example, the following construct is provided in which m630.3 (shown in bold) is fused to a linker (shown in italics) which is fused to a human IgG1 Fc domain (shown underlined):

(SEQ ID NO: 6)
QVQLVQSGGGLVQPGGSLRLSCAASSFDFDYYEMSWVRQAPGQRLE

WVAYISKSGGTKMYADSVKGRFTISRDNSKNTLYLQMNTLRAEDTA

MYYCAKDRATCRGGRCYSFYYGMDVWGQGTLVTVSS*GPDKTHTCPP*

*CPAPELLGGPSVFLFPPKPKDTLMISRTPEVTCVVVDVSHEDPEVKFNWY*

*VDGVEVHNAKTKPREEQYNSTYRVVSVLTVLHQDWLNGKEYKCKVSNK*

*ALPAPIEKTISKAKGQPREPQVYTLPPSRDELTKNQVSLTCLVKGFYPSD*

*IAVEWESNGQPENNYKTTPPVLDSDGSFFLYSKLTVDKSRWQQGNVFSCS*

*VMHEALHNHYTQKSLSLSPGK*.

Figure 2D:
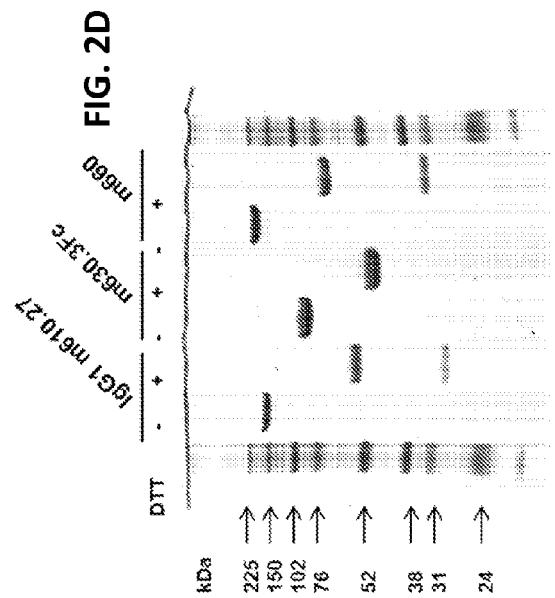
Figure 2A:
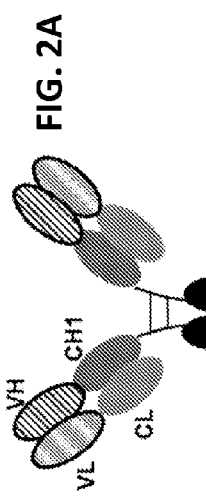
Figure 2C:
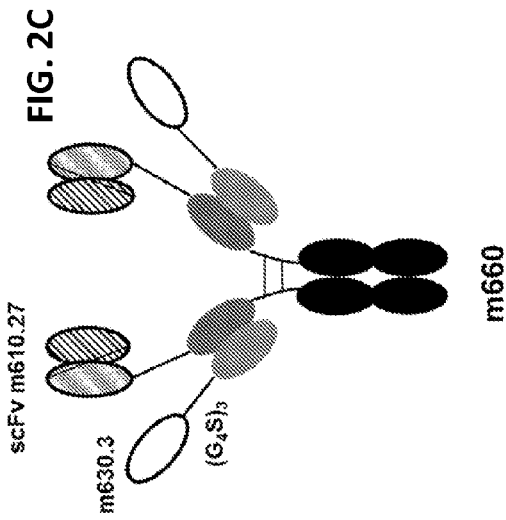

Exemplary bispecific antibodies include an antigen binding fragment that specifically binds one epitope of IGF-II and an eAd that specifically binds a different epitope of IGF-II. In some embodiments, these bispecific antibodies include an antigen binding fragment of m610.27. In another embodiment, the bispecific antibody includes an antigen binding fragment of an antibody that comprises the heavy chain CDRs of m610.27, for example amino acids 26-33, 51-58, and 97-109 of SEQ ID NO: 1 and/or the light chain CDRs of m610.27, for example amino acids 27-32, 50-52 and 89-98 of SEQ ID NO: 2. This antigen binding fragment can be, but is not limited to, an scFv fragment. The antigen binding fragment can be bound to a first constant domain. An exemplary construct is illustrated in FIG. 2A. The bispecific antibody can also include an eAd disclosed herein. The eAd can be bound to a constant domain. An exemplary construct is shown in FIG. 2B. A bispecific antibody can be produced that includes the antigen binding fragment ligated to a constant domain and an eAd ligated to a constant domain. Thus, a bispecific antibody can include an scFv and a constant domain, and an eAd and a second constant domain. An exemplary construct is shown in FIG. 2C. One example includes the following amino acid sequence in which scFv m610.27 (shown in bold) is fused to a linker (shown in italics) which is fused to a human IgG1 heavy chain constant region (shown underlined):

(SEQ ID NO: 7)
QVQLVQSGAEVKKPGASVKVSCKASGYTFTSYYMHWVRQAPGQGLE

WMGIINPSGGSTSYAQKFQGRVTMTRDTSTSTVYMELSRLRSDDTAV

YYCARDVQWLAYGMDVWGQGTTVTVSS*GGGGSGGGGSGGGGSDIQ*

*MTQSPSSLSASVGDRVTITCRASQSISSYLNWYQQKPGRAPDLLINAAS*

*SLQSGVPSRFSGSGSGTDFTLTISSLQPEDFATYFCQQSYSLPFTFGGG*

TKVEIKR*GGGGSGGGGSGGGGSS*ASTKGPSVFPLAPSSKSTSGGTAALG

CLVKDYFPEPVTVSWNSGALTSGVHTFPAVLQSSGLYSLSSVVTVPSSSL

GTQTYICNVNHKPSNTKVDKKVEPKSCDKTHTCPPCPAPELLGGPSVFLF

-continued
PPKPKDTLMISRTPEVTCVVVDVSHEDPEVKFNWYVDGVEVHNAKTKPRE

EQYNSTYRVVSVLTVLHQDWLNGKEYKCKVSNKALPAPIEKTISKAKGQP

REPQVYTLPPSRDELTKNQVSLTCLVKGFYPSDIAVEWESNGQPENNYKT

TPPVLDSDGSFFLYSKLTVDKSRWQQGNVFSCSVMHEALHNHYTQKSLSL

SPGK.

Another example includes the following amino acid sequence in which m630.3 (shown in bold) is fused to a linker (shown in italics) which is fused to a human IgG1 light chain constant region (shown underlined):

(SEQ ID NO: 8)
QVQLVQSGGGLVQPGGSLRLSCAASSFDFDYYEMSWVRQAPGQRLE

WVAYISKSGGTKMYADSVKGRFTISRDNSKNTLYLQMNTLRAEDTA

MYYCAKDRATCRGGRCYSFYYGMDVWGQGTLVTVSS*GGGGSGGGGS*

*GGGGS*RTVAAPSVFIFPPSDEQLKSGTASVVCLLNNFYPREAKVQWKVDN

ALQSGNSQESVTEQDSKDSTYSLSSTLTLSKADYEKHKVYACEVTHQGLS

SPVTKSFNRGEC.

One type of derivatized antibody is produced by crosslinking two or more antibodies, antigen binding fragments, eAds (of the same type or of different types) to create bispecific antibodies. Suitable crosslinkers include those that are heterobifunctional, having two distinctly reactive groups separated by an appropriate spacer (such as m-maleimidobenzoyl-N-hydroxysuccinimide ester) or homobifunctional (such as disuccinimidyl suberate). Such linkers are available from Pierce Chemical Company, Rockford, Ill. Exemplary bispecific antibodies are disclosed in the examples section.

Polypeptides typically contain a variety of functional groups; such as carboxylic acid (COOH), free amine (—NH$_2$) or sulfhydryl (—SH) groups, which are available for reaction with a suitable functional group on an antibody to result in the binding of the effector molecule. Alternatively, the antibody, antigen binding fragment, eAd or bispecific antibody is derivatized to expose or attach additional reactive functional groups. The derivatization may involve attachment of any of a number of linker molecules such as those available from Pierce Chemical Company, Rockford, Ill. The linker can be any molecule used to join the antibody to the effector molecule. The linker is capable of forming covalent bonds to both the antibody and to the effector molecule. Suitable linkers are well known to those of skill in the art and include, but are not limited to, straight or branched-chain carbon linkers, heterocyclic carbon linkers, or peptide linkers. Where the antibody, antigen binding fragment, eAd or bispecific antibody and the effector molecule are polypeptides, the linkers may be joined to the constituent amino acids through their side groups (such as through a disulfide linkage to cysteine) or to the alpha carbon amino and carboxyl groups of the terminal amino acids. In fact, similar methods can be used to form a bispecific antibody, such as by attaching a mAb or antigen binding fragment to an eAd.

In one embodiment, the bispecific antibody includes an eAd that specifically binds a first epitope of IGF-II, wherein the eAd is covalently linked to a first constant domain; and antigen binding fragment (such as an scFv) that specifically binds a second epitope of IGF-II, wherein the antigen binding fragment is covalently linked to a second constant domain. The first constant domain is covalently linked to the second constant domain, such that the bi-specific mAb specifically binds IGF-II. Any of the eAds and scFvs of any of the monoclonal antibodies disclosed herein can be included. Exemplary constructs are shown in FIG. 2C.

The mAbs, bispecific antibodies, eAd or any of the antibody fragments disclosed herein that specifically bind IGF-II can be derivatized or linked to another molecule (such as another peptide or protein). In general, the antibodies or portion thereof is derivatized such that the binding to IGF-II is not affected adversely by the derivatization or labeling. For example, the antibody can be functionally linked (by chemical coupling, genetic fusion, noncovalent association or otherwise) to one or more other molecular entities, such as another antibody (for example, to form a bispecific antibody), a detection agent, a pharmaceutical agent, and/or a protein or peptide that can mediate associate of the antibody or antibody portion with another molecule (such as a streptavidin core region or a polyhistidine tag).

Effector molecules, such as therapeutic, diagnostic, or detection moieties can be linked to an antibody, antibody fragment, bispecific antibody or eAd that specifically binds IGF-II, using any number of means known to those of skill in the art. Both covalent and noncovalent attachment means may be used. The procedure for attaching an effector molecule to an antibody varies according to the chemical structure of the effector. In some circumstances, it is desirable to free the effector molecule from the antibody, antigen binding fragment, eAd or bispecific antibody when the immunoconjugate has reached its target site. Therefore, in these circumstances, immunoconjugates will comprise linkages that are cleavable in the vicinity of the target site. Cleavage of the linker to release the effector molecule from the antibody may be prompted by enzymatic activity or conditions to which the immunoconjugate is subjected either inside the target cell or in the vicinity of the target site. In view of the large number of methods that have been reported for attaching a variety of radiodiagnostic compounds, radiotherapeutic compounds, labels (such as enzymes or fluorescent molecules) drugs, toxins, and other agents, one skilled in the art will be able to determine a suitable method for attaching a given agent to an antibody or other polypeptide.

A mAb, antigen binding fragment, eAd or bispecific antibody that specifically binds IGF-II can be labeled with a detectable moiety. Useful detection agents include fluorescent compounds, including fluorescein, fluorescein isothiocyanate, rhodamine, 5-dimethylamine-1-napthalenesulfonyl chloride, phycoerythrin, lanthanide phosphors and the like. Bioluminescent markers are also of use, such as luciferase, green fluorescent protein (GFP), yellow fluorescent protein (YFP). A mAb, antigen binding fragment, eAd or bispecific antibody can also be labeled with enzymes that are useful for detection, such as horseradish peroxidase, β-galactosidase, luciferase, alkaline phosphatase, glucose oxidase and the like. A detectable enzyme can be detected by adding additional reagents that the enzyme uses to produce a reaction product that can be discerned. For example, when the agent horseradish peroxidase is present, the addition of hydrogen peroxide and diaminobenzidine leads to a colored reaction product, which is visually detectable. A mAb, antigen binding fragment, eAd or bispecific antibody may also be labeled with biotin, and detected through indirect measurement of avidin or streptavidin binding. It should be noted that the avidin itself can be labeled with an enzyme or a fluorescent label.

A mAb, antigen binding fragment, eAd or bispecific antibody may be labeled with a magnetic agent, such as gadolinium. A mAb, antigen binding fragment, eAd or bispecific antibody can also be labeled with lanthanides (such as europium and dysprosium), and manganese. Paramagnetic particles such as superparamagnetic iron oxide are also of use as labels. A mAb, antigen binding fragment, eAd or bispecific antibody may also be labeled with a predetermined polypeptide epitopes recognized by a secondary reporter (such as leucine zipper pair sequences, binding sites for secondary antibodies, metal binding domains, epitope tags). In some embodiments, labels are attached by spacer arms of various lengths to reduce potential steric hindrance.

A mAb, antigen binding fragment, eAd or bispecific antibody can also be labeled with a radiolabeled amino acid. The radiolabel may be used for both diagnostic and therapeutic purposes. For instance, the radiolabel may be used to detect IGF-II by x-ray, emission spectra, or other diagnostic techniques. Examples of labels for polypeptides include, but are not limited to, the following radioisotopes or radionuclides: $^{3}H$, $^{14}C$, $^{15}N$, $^{35}S$, $^{90}Y$, $^{99}Tc$, $^{111}In$, $^{125}I$, $^{131}I$.

A mAb, antigen binding fragment, eAd or bispecific antibody can also be derivatized with a chemical group such as polyethylene glycol (PEG), a methyl or ethyl group, or a carbohydrate group. These groups may be useful to improve the biological characteristics of the antibody, such as to increase serum half-life or to increase tissue binding.

In one embodiment, the mAb, antigen binding fragment, eAd or bispecific antibody that specifically binds IGF-II inhibits phosphorylation of the IGF-IR. IGF-II binds the IGF-IR, and causes tyrosine phosphorylation. Tyrosine phosphorylation of IGF-IR is one of the early responses to potent mitogenic stimuli, such as the binding of IGF-I or IFG-II. The IGF-IR binds IGF-I and IGF-II with high affinity to activate cellular proliferation in both normal growth and development and malignant transformation and has tyrosine kinase activity. IGF-IR is highly over expressed in most malignant tissues where it functions as an anti-apoptotic agent by enhancing cell survival. Tyrosine phosphorylation status of proteins can be determined using anti-phosphotyrosine antibodies. In addition, because of the binding specificity of the SH2 domain to phosphorylated tyrosine residues, a specific pattern of tyrosine phosphorylation can be elucidated to determine phosphorylation status.

Immunoassays for determining IGF-IR tyrosine phosphorylation or for measuring total IGF-IR levels are an ELISA or Western blot. If only the cell surface level of IGF-IR is to be measured, the cells are not lysed, and the cell surface levels of IGF-IR are measured using one of the assays described herein. In one example, the immunoassay for determining cell surface levels of IGF-IR includes the steps of labeling the cell surface proteins with a detectable label, such as $^{32}P$, immunoprecipitating the IGF-IR with an anti-IGF-IR antibody and then detecting the phosphorylated IGF-IR.

Nucleic Acids and Host Cells

Nucleic acids encoding the amino acid sequences of the eAd and mAbs that specifically bind IGF-II are also provided herein. The nucleic acid molecules can encode a heavy chain variable domain and/or a light chain variable domain. Exemplary nucleic acid sequences are as follows:

```
Heavy chain nucleotide sequence (m610.27)
(SEQ ID NO: 9):
CAAGTGCAGCTGGTGCAGTCTGGGGCTGAGGTGAAGAAGCCTGGGGC

CTCAGTGAAGGTTTCCTGCAAGGCATCTGGATACACCTTCACCAGCTA

CTATATGCACTGGGTGCGACAGGCCCCTGGACAAGGGCTTGAGTGGAT

GGGAATAATCAACCCTAGTGGTGGTAGCACAAGCTACGCACAGAAGT
```

TCCAGGGCAGAGTCACCATGACCAGGGACACGTCCACGAGCACAGTC

TACATGGAGCTGAGCAGGCTGAGATCTGACGACACGGCCGTGTATTAC

TGTGCGAGAGATGTGCAGTGGCTGGCATACGGTATGGACGTCTGGGGC

CAAGGGACCACGGTCACCGTGAGCTCAGCCTCCACCAAGGGCCCATC

GGTCTTCCCCCTGGCACCCTCCTCCAAGAGCACCTCTGGGGGCACAGC

GGCCCTGGGCTGCCTGGTCAAGGACTACTTCCCCGAACCGGTGACGGT

GTCGTGGAACTCAGGCGCCCTGACCAGCGGCGTGCACACCTTCCCGGC

TGTCCTACAGTCCTCAGGACTCTACTCCCTCAGCAGCGTGGTGACCGT

GCCCTCCAGCAGCTTGGGCACCCAGACCTACATCTGCAACGTGAATCA

CAAGCCCAGCAACACCAAGGTGGACAAGAAAGTTGAGCCCAAATCTT

GTGACAAAACTCACACATGCCCACCGTGCCCAGCACCTGAACTCCTGG

GGGGACCGTCAGTCTTCCTCTTCCCCCCAAAACCCAAGGACACCCTCA

TGATCTCCCGGACCCCTGAGGTCACATGCGTGGTGGTGGACGTGAGCC

ACGAAGACCCTGAGGTCAAGTTCAACTGGTACGTGGACGGCGTGGAG

GTGCATAATGCCAAGACAAAGCCGCGGGAGGAGCAGTACAACAGCAC

GTACCGTGTGGTCAGCGTCCTCACCGTCCTGCACCAGGACTGGCTGAA

TGGCAAGGAGTACAAGTGCAAGGTCTCCAACAAAGCCCTCCCAGCCC

CCATCGAGAAAACCATCTCCAAAGCCAAAGGGCAGCCCCGAGAACCA

CAGGTGTACACCCTGCCCCCATCCCGGGATGAGCTGACCAAGAACCAG

GTCAGCCTGACCTGCCTGGTCAAAGGCTTCTATCCCAGCGACATCGCC

GTGGAGTGGGAGAGCAATGGGCAGCCGGAGAACAACTACAAGACCAC

GCCTCCCGTGCTGGACTCCGACGGCTCCTTCTTCCTCTACAGCAAGCTC

ACCGTGGACAAGAGCAGGTGGCAGCAGGGGAACGTCTTCTCATGCTC

CGTGATGCATGAGGCTCTGCACAACCACTACACGCAGAAGAGCCTCTC

CCTGTCTCCGGGTAAA

Light chain nucleotide sequence (m610.27)
(SEQ ID NO: 10):
GACATCCAGATGACCCAGTCTCCATCCTCCCTGTCTGCATCTGTAGGAGA

CAGAGTCACCATCACTTGCCGGGCAAGTCAGAGCATTAGTAGCTATTTA

AATTGGTATCAGCAGAAGCCAGGGAGAGCCCCTGACCTCCTGATCAATG

CTGCATCCAGTTTGCAAAGTGGGGTCCCATCAAGGTTCAGTGGCAGTGG

ATCTGGGACCGACTTCACTCTCACCATCAGCAGTCTCCAACCTGAAGATT

TTGCAACTTACTTCTGTCAACAGAGTTACAGTCTTCCGTTCACTTTCGGC

GGAGGGACCAAGGTGGAGATCAAAGGAACTGTGGCTGCACCATCTGTCT

TCATCTTCCCGCCATCTGATGAGCAGTTGAAATCTGGAACTGCCTCTGTT

GTGTGCCTGCTGAATAACTTCTATCCCAGAGAGGCCAAAGTACAGTGGA

AGGTGGATAACGCCCTCCAATCGGGTAACTCCCAGGAGAGTGTCACAGA

GCAGGACAGCAAGGACAGCACCTACAGCCTCAGCAGCACCCTGACGCTG

AGCAAAGCAGACTACGAGAAACACAAAGTCTACGCCTGCGAAGTCACCC

ATCAGGGCCTGAGCTCGCCCGTCACAAAGAGCTTCAACAGGGGAGAGTG

T

EAd (m630) (SEQ ID NO: 11):
CAGGTGCAGCTGGTGCAGTCTGGGGGAGGCTTGGTACAGCCTGGAGGGT

CCCTGAGACTCTCCTGTGCAGCCTCTTCTTTCGATTTCGATTATTATGAA

ATGAGCTGGGTCCGCCAGGCTCCAGGACAACGGCTTGAGTGGGTTGCATA

CATTAGTAAGAGTGGCGGTACCAAAATGTATGCAGACTCGGTGAAGGGC

CGATTCACCATCTCCAGAGACAATTCCAAGAACACGCTGTATCTGCAAA

TGAACACCCTGAGAGCCGAGGACACAGCCATGTATTACTGTGCGAAAGA

TCGGGCAACTTGTAGTGGTGGTAGCTGCTACTCCTTTTACTACGGTATGG

ACGTCTGGGGCCAAGGCACCCTGGTCACCGTCTCCTCA

EAd (m630.1) (SEQ ID NO: 12):
CAGGTGCAGCTGGTGCAGTCTGGGGGAGGCTTGGTACAGCCTGGAGGGT

CCCTGAGACTCTCCTGTGCAGCCTCTTCTTTCGATTTCGATTATTATGAA

ATGAGCTGGGTCCGCCAGGCTCCAGGACAACGGCTTGAGTGGGTTGCATA

CATTAGTAAGAGTGGCGGTACCAAAATGTATGCAGACTCGGTGAAGGGC

CGATTCACCATCTCCAGAGACAATTCCAGGAACACGCTGTATCTGCAAA

TGAACACCCTGAGAGCCGAGGACACAGCCATGTATTACTGTGCGAAAGA

TCGGGCAACTTGTAGAGGTGGTAGCTGCTACTCCTTTTACCACGGTATGG

ACGTCTGGGGCCAAGGCACCCTGGTCACCGTCTCCTCA

EAd (m630.3) (SEQ ID NO: 13):
CAGGTGCAGCTGGTGCAGTCTGGGGGAGGCTTGGTACAGCCTGGAGGGT

CCCTGAGACTCTCCTGTGCAGCCTCTTCTTTCGATTTCGATTATTATGAA

ATGAGCTGGGTCCGCCAGGCTCCAGGACAACGGCTTGAGTGGGTTGCATA

CATTAGTAAGAGTGGCGGTACCAAAATGTATGCAGACTCGGTGAAGGGC

CGATTCACCATCTCCAGAGACAATTCCAAGAACACGCTGTATCTGCAAA

TGAACACCCTGAGAGCCGAGGACACAGCCATGTATTACTGTGCGAAAGA

TCGGGCAACTTGTAGAGGTGGTCGCTGCTACTCCTTTTACTACGGTATGG

ACGTCTGGGGCCAAGGCACCCTGGTCACCGTCTCCTCA

EAd (m630.4) (SEQ ID NO: 14):
CAGGTGCAGCTGGTGCAGTCTGGGGGAGGCTTGGTACAGCCTGGAGGGT

CCCTGAGACTCTCCTGTGCAGCCTCTTCTTTCGATTTCGGTTATTATGAA

ATGAGCTGGGTCCGCCAGGCTCCAGGACAACGGCTTGAGTGGGTTGCATA

CATTAGTAAGAGTGGCGGTACCAAAATGTATGCAGACTCGGTGAAGGGC

CGATTCACCATCTCCAGAGACAATTCCAAGAACACGCTGTATCTGCAAA

TGAACACCCTGAGAGCCGAGGACACAGCCATGTATTACTGTGCGAAAGA

TCGGGCAACTTGTAGTGGTGGTAGATGCTACTCCTTTTACTACGGTATGG

ACGTCTGGGGCCAAGGCACCCTGGTCACCGTCTCCTCA

EAd (m630.9) (SEQ ID NO: 15):
CAGGTGCAGCTGGTGCAGTCTGGGGGAGGCTTGGTACAGCCTGGAGGGT

CCCTGAGACTCTCCTGTGCAGCCTCTTCTTTCGATTATTATGAA

ATGAGCTGGGTCCGCCAGGCCCCAGGACAACGGCTTGAGTGGGTTGCATA

CATTAGTAAGAGTGGCGGTACCAAAATGTATGCAGACTCGGTGAAGGGC

CGATTCACCATCTCCAGAGACAATTCCAAGAACACGCTGTATCTGCAAA

TGAACACCCTGAGAGCCGAGGACACAGCCATGTATTACTGTGCGAAAGA

EAd-Fc (m630.3Fc) (SEQ ID NO: 16):
CAGGTGCAGCTGGTGCAGTCTGGGGGAGGCTTGGTACAGCCTGGAGGGT

CCCTGAGACTCTCCTGTGCAGCCTCTTCTTTCGATTTCGATTATTATGAA

ATGAGCTGGGTCCGCCAGGCTCCAGGACAACGGCTTGAGTGGGTTGCATA

CATTAGTAAGAGTGGCGGTACCAAAATGTATGCAGACTCGGTGAAGGGC

CGATTCACCATCTCCAGAGACAATTCCAAGAACACGCTGTATCTGCAAA

TGAACACCCTGAGAGCCGAGGACACAGCCATGTATTACTGTGCGAAAGA

TCGGGCAACTTGTAGAGGTGGTCGCTGCTACTCCTTTTACTACGGTATGG

ACGTCTGGGGCCAAGGCACCCTGGTCACCGTCTCCTCAGGGCCCGACAA

AACTCACACATGCCCACCGTGCCCAGCACCTGAACTCCTGGGGGACCG

TCAGTCTTCCTCTTCCCCCCAAAACCCAAGGACACCCTCATGATCTCCCG

GACCCCTGAGGTCACATGCGTGGTGGTGGACGTGAGCCACGAAGACCCT

GAGGTCAAGTTCAACTGGTACGTGGACGGCGTGGAGGTGCATAATGCCA

AGACAAAGCCGCGGGAGGAGCAGTACAACAGCACGTACCGTGTGGTCA

GCGTCCTCACCGTCCTGCACCAGGACTGGCTGAATGGCAAGGAGTACAA

GTGCAAGGTCTCCAACAAAGCCCTCCCAGCCCCCATCGAGAAAACCATC

TCCAAAGCCAAAGGGCAGCCCCGAGAACCACAGGTGTACACCCTGCCCC

CATCCCGGGATGAGCTGACCAAGAACCAGGTCAGCCTGACCTGCCTGGT

CAAAGGCTTCTATCCCAGCGACATCGCCGTGGAGTGGGAGAGCAATGGG

CAGCCGGAGAACAACTACAAGACCACGCCTCCCGTGCTGGACTCCGACG

GCTCCTTCTTCCTCTACAGCAAGCTCACCGTGGACAAGAGCAGGTGGCA

GCAGGGGAACGTCTTCTCATGCTCCGTGATGCATGAGGCTCTGCACAAC

CACTACACGCAGAAGAGCCTCTCCCTGTCTCCGGGTAAA m660, heavy chain
(SEQ ID NO: 17, part of m660):
CAAGTGCAGCTGGTGCAGTCTGGGGCTGAGGTGAAGAAGCCTGGGGCCT

CAGTGAAGGTTTCCTGCAAGGCATCTGGATACACCTTCACCAGCTACTAT

ATGCACTGGGTGCGACAGGCCCCTGGACAAGGGCTTGAGTGGATGGGAA

TAATCAACCCTAGTGGTGGTAGCACAAGCTACGCACAGAAGTTCCAGGG

CAGAGTCACCATGACCAGGGACACGTCCACGAGCACAGTCTACATGGAG

CTGAGCAGGCTGAGATCTGACGACACGGCCGTGTATTACTGTGCGAGAG

ATGTGCAGTGGCTGGCATACGGTATGGACGTCTGGGGCCAAGGGACCAC

GGTCACCGTCTCCTCAGGTGGAGGCGGTTCAGGCGGAGGTGGCTCTGGC

GGTGGCGGATCAGACATCCAGATGACCCAGTCTCCATCCTCCCTGTCTGC

ATCTGTAGGAGACAGAGTCACCATCACTTGCCGGGCAAGTCAGAGCATT

AGTAGCTATTTAAATTGGTATCAGCAGAAGCCAGGGAGAGCCCCTGACC

TCCTGATCAATGCTGCATCCAGTTTGCAAAGTGGGGTCCCATCAAGGTTC

AGTGGCAGTGGATCTGGGACCGACTTCACTCTCACCATCAGCAGTCTCCA

ACCTGAAGATTTTGCAACTTACTTCTGTCAACAGAGTTACAGTCTTCCGT

TCACTTTCGGCGGAGGGACCAAGGTGGAGATCAAACGAGGTGGAGGCG

GTTCAGGCGGAGGTGGCTCTGGCGGTGGCGGATCGAGCTCAGCCTCCAC

CAAGGGCCCATCGGTCTTCCCCCTGGCACCCTCCTCCAAGAGCACCTCTG

GGGGCACAGCGGCCCTGGGCTGCCTGGTCAAGGACTACTTCCCCGAACC

GGTGACGGTGTCGTGGAACTCAGGCGCCCTGACCAGCGGCGTGCACACC

TTCCCGGCTGTCCTACAGTCCTCAGGACTCTACTCCCTCAGCAGCGTGGT

GACCGTGCCCTCCAGCAGCTTGGGCACCCAGACCTACATCTGCAACGTG

AATCACAAGCCCAGCAACACCAAGGTGGACAAGAAAGTTGAGCCCAAA

TCTTGTGACAAAACTCACACATGCCCACCGTGCCCAGCACCTGAACTCCT

GGGGGGACCGTCAGTCTTCCTCTTCCCCCCAAAACCCAAGGACACCCTC

ATGATCTCCCGGACCCCTGAGGTCACATGCGTGGTGGTGGACGTGAGCC

ACGAAGACCCTGAGGTCAAGTTCAACTGGTACGTGGACGGCGTGGAGGT

GCATAATGCCAAGACAAAGCCGCGGGAGGAGCAGTACAACAGCACGTA

CCGTGTGGTCAGCGTCCTCACCGTCCTGCACCAGGACTGGCTGAATGGC

AAGGAGTACAAGTGCAAGGTCTCCAACAAAGCCCTCCCAGCCCCCATCG

AGAAAACCATCTCCAAAGCCAAAGGGCAGCCCCGAGAACCACAGGTGT

ACACCCTGCCCCCATCCCGGGATGAGCTGACCAAGAACCAGGTCAGCCT

GACCTGCCTGGTCAAAGGCTTCTATCCCAGCGACATCGCCGTGGAGTGG

GAGAGCAATGGGCAGCCGGAGAACAACTACAAGACCACGCCTCCCGTG

CTGGACTCCGACGGCTCCTTCTTCCTCTACAGCAAGCTCACCGTGGACAA

GAGCAGGTGGCAGCAGGGGAACGTCTTCTCATGCTCCGTGATGCATGAG

GCTCTGCACAACCACTACACGCAGAAGAGCCTCTCCCTGTCTCCGGGTA

AA m660, light chain
(SEQ ID NO: 18, part of m660):
CAGGTGCAGCTGGTGCAGTCTGGGGGAGGCTTGGTACAGCCTGGAGGGT

CCCTGAGACTCTCCTGTGCAGCCTCTTCTTTCGATTTCGATTATTATGAA

ATGAGCTGGGTCCGCCAGGCTCCAGGACAACGGCTTGAGTGGGTTGCATA

CATTAGTAAGAGTGGCGGTACCAAAATGTATGCAGACTCGGTGAAGGGC

CGATTCACCATCTCCAGAGACAATTCCAAGAACACGCTGTATCTGCAAA

TGAACACCCTGAGAGCCGAGGACACAGCCATGTATTACTGTGCGAAAGA

TCGGGCAACTTGTAGAGGTGGTCGCTGCTACTCCTTTTACTACGGTATGG

ACGTCTGGGGCCAAGGCACCCTGGTCACCGTCTCCTCAGGTGGAGGCGG

TTCAGGCGGAGGTGGCTCTGGCGGTGGCGGATCACGAACTGTGGCTGCA

CCATCTGTCTTCATCTTCCCGCCATCTGATGAGCAGTTGAAATCTGGAAC

TGCCTCTGTTGTGTGCCTGCTGAATAACTTCTATCCCAGAGAGGCCAAAG

TACAGTGGAAGGTGGATAACGCCCTCCAATCGGGTAACTCCCAGGAGAG

TGTCACAGAGCAGGACAGCAAGGACAGCACCTACAGCCTCAGCAGCACC

CTGACGCTGAGCAAAGCAGACTACGAGAAACACAAAGTCTACGCCTGCG

AAGTCACCCATCAGGGCCTGAGCTCGCCCGTCACAAAGAGCTTCAACAG

GGGAGAGTGT

Recombinant nucleotide acid molecules encoding antibodies, antigen binding fragments, eAd, components of bispecific antibodies (such as an eAd and a constant domain or an scFv and a constant domain), or a bispecific antibody, can readily be produced by one of skill in the art, using the amino acid sequences provided herein, and the genetic code. In addition, one of skill can readily construct a variety of clones containing functionally equivalent nucleic acids, such as nucleic acids which differ in sequence but which encode the same protein sequence. Thus, nucleic acids encoding mAbs, antigen binding fragments, eAds, Fc fusion proteins, bispecific antibodies and their components, conjugates and fusion proteins are provided herein.

Nucleic acid sequences encoding mAbs, antigen binding fragments, eAds and bispecific antibodies that specifically bind IGF-II can be prepared by any suitable method including, for example, cloning of appropriate sequences or by direct chemical synthesis by methods such as the phosphotriester method of Narang et al., *Meth. Enzymol.* 68:90-99, 1979; the phosphodiester method of Brown et al., *Meth. Enzymol.* 68:109-151, 1979; the diethylphosphoramidite method of Beaucage et al., *Tetra. Lett.* 22:1859-1862, 1981; the solid phase phosphoramidite triester method described by Beaucage & Caruthers, *Tetra. Letts.* 22(20):1859-1862, 1981, for example, using an automated synthesizer as described in, for example, Needham-VanDevanter et al., *Nucl. Acids Res.* 12:6159-6168, 1984; and, the solid support method of U.S. Pat. No. 4,458,066. Chemical synthesis produces a single stranded oligonucleotide. This can be converted into double stranded DNA by hybridization with a complementary sequence, or by polymerization with a DNA polymerase using the single strand as a template. One of skill would recognize that while chemical synthesis of DNA is generally limited to sequences of about 100 bases, longer sequences may be obtained by the ligation of shorter sequences.

Exemplary nucleic acids encoding mAbs, antigen binding fragments, eAds or bispecific antibody that specifically binds IGF-II can be prepared by cloning techniques. Examples of appropriate cloning and sequencing techniques, and instructions sufficient to direct persons of skill through many cloning exercises are found in Sambrook et al., supra, Berger and Kimmel (eds.), supra, and Ausubel, supra. Product information from manufacturers of biological reagents and experimental equipment also provide useful information. Such manufacturers include the SIGMA Chemical Company (Saint Louis, Mo.), R&D Systems (Minneapolis, Minn.), Pharmacia Amersham (Piscataway, N.J.), CLONTECH Laboratories, Inc. (Palo Alto, Calif.), Chem Genes Corp., Aldrich Chemical Company (Milwaukee, Wis.), Glen Research, Inc., GIBCO BRL Life Technologies, Inc. (Gaithersburg, Md.), Fluka Chemica-Biochemika Analytika (Fluka Chemie AG, Buchs, Switzerland), Invitrogen (San Diego, Calif.), and Applied Biosystems (Foster City, Calif.), as well as many other commercial sources known to one of skill Nucleic acids can also be prepared by amplification methods. Amplification methods include polymerase chain reaction (PCR), the ligase chain reaction (LCR), the transcription-based amplification system (TAS), the self-sustained sequence replication system (3SR). A wide variety of cloning methods, host cells, and in vitro amplification methodologies are well known to persons of skill In one example, an antibody or eAd of use is prepared by inserting the cDNA which encodes a variable region from an antibody or an eAd into a vector which comprises the cDNA encoding an effector molecule (EM), such as an enzyme or label. The insertion is made so that the variable region and the EM are read in frame so that one continuous polypeptide is produced. Thus, the encoded polypeptide contains a functional Fv region or an eAd and a functional EM region. In one embodiment, cDNA encoding an enzyme is ligated to a scFv or an eAd so that the enzyme is located at the carboxyl terminus of the scFv. In several examples, cDNA encoding a horseradish peroxidase or alkaline phosphatase, or a polypeptide marker of interest is ligated to a scFv or an eAd so that the enzyme (or polypeptide marker) is located at the amino terminus of the scFv or the eAd. In another example, the label is located at the amino terminus of the scFv or the eAd. In a further example, cDNA encoding the protein or polypeptide marker is ligated to a heavy chain variable region of an antibody, so that the enzyme or polypeptide marker is located at the carboxyl terminus of the heavy chain variable region. The heavy chain-variable region can subsequently be ligated to a light chain variable region of the antibody using disulfide bonds, or can be linked to an eAd. In yet another example, cDNA encoding an enzyme or a polypeptide marker is ligated to a light chain variable region of an antibody, so that the enzyme or polypeptide marker is located at the carboxyl terminus of the light chain variable region. The light chain-variable region can subsequently be ligated to a heavy chain variable region of the antibody using disulfide bonds.

Once the nucleic acids encoding the mAb, antigen binding fragment, eAd or bispecific antibody that specifically bind IGF-II is isolated and cloned, the protein can be expressed in a recombinantly engineered cell such as bacteria, plant, yeast, insect and mammalian cells using a suitable expression vector. One or more DNA sequences encoding the antibody or fragment thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art. Hybridomas expressing the antibodies of interest are also encompassed by this disclosure.

Polynucleotide sequences encoding the mAb, antigen binding fragment, eAd or bispecific antibody that specifically bind IGF-II, can be operatively linked to expression control sequences. An expression control sequence operatively linked to a coding sequence is ligated such that expression of the coding sequence is achieved under conditions compatible with the expression control sequences. The expression control sequences include, but are not limited to appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

The polynucleotide sequences encoding the antibody, labeled antibody, or functional fragment thereof can be inserted into an expression vector including, but not limited to a plasmid, virus or other vehicle that can be manipulated to allow insertion or incorporation of sequences and can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art.

Transformation of a host cell with recombinant DNA may be carried out by conventional techniques as are well known to those skilled in the art. Where the host is prokaryotic, such as *E. coli*, competent cells which are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors may be used. Eukaryotic cells can also be cotransformed with polynucleotide sequences encoding the antibody, labeled antibody, or functional (antigen binding) fragment thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982). One of skill in the art can readily use an expression systems such as plasmids and vectors of use in producing proteins in cells including higher eukaryotic cells such as the COS, CHO, HeLa and myeloma cell lines.

Isolation and purification of recombinantly expressed polypeptide can be carried out by conventional means including preparative chromatography and immunological separations. Once expressed, the antibody, labeled antibody or functional fragment thereof can be purified according to standard procedures of the art, including ammonium sulfate precipitation, affinity columns, column chromatography, and the like (see, generally, R. Scopes, *Protein Purification*, Springer-Verlag, N.Y., 1982). Substantially pure compositions of at least about 90 to 95% homogeneity are disclosed herein, and 98 to 99% or more homogeneity can be used for pharmaceutical purposes. Once purified, partially or to homogeneity as desired, if to be used therapeutically, the polypeptides should be substantially free of endotoxin.

Methods for expression of single chain antibodies (or eAds) and/or refolding to an appropriate active form, including single chain antibodies, from bacteria such as *E. coli* have been described and are well-known and are applicable to the antibodies disclosed herein. See, Buchner et al., *Anal. Biochem.* 205:263-270, 1992; Pluckthun, *Biotechnology* 9:545, 1991; Huse et al., *Science* 246:1275, 1989 and Ward et al., *Nature* 341:544, 1989, all incorporated by reference herein.

Often, functional heterologous proteins from *E. coli* or other bacteria are isolated from inclusion bodies and require solubilization using strong denaturants, and subsequent refolding. During the solubilization step, as is well known in the art, a reducing agent must be present to separate disulfide bonds. An exemplary buffer with a reducing agent is: 0.1 M Tris pH 8, 6 M guanidine, 2 mM EDTA, 0.3 M DTE (dithioerythritol). Reoxidation of the disulfide bonds can occur in the presence of low molecular weight thiol reagents in reduced and oxidized form, as described in Saxena et al., *Biochemistry* 9: 5015-5021, 1970, incorporated by reference herein, and especially as described by Buchner et al., supra.

Renaturation is typically accomplished by dilution (for example, 100-fold) of the denatured and reduced protein into refolding buffer. An exemplary buffer is 0.1 M Tris, pH 8.0, 0.5 M L-arginine, 8 mM oxidized glutathione (GSSG), and 2 mM EDTA.

As a modification to the two chain antibody purification protocol, the heavy and light chain regions are separately solubilized and reduced and then combined in the refolding solution. An exemplary yield is obtained when these two proteins are mixed in a molar ratio such that a 5 fold molar excess of one protein over the other is not exceeded. Excess oxidized glutathione or other oxidizing low molecular weight compounds can be added to the refolding solution after the redox-shuffling is completed.

In addition to recombinant methods, the mAbs, antigen binding fragments, eAds and bispecific antibodies that are disclosed herein can also be constructed in whole or in part using standard peptide synthesis. Solid phase synthesis of the polypeptides of less than about 50 amino acids in length can be accomplished by attaching the C-terminal amino acid of the sequence to an insoluble support followed by sequential addition of the remaining amino acids in the sequence. Techniques for solid phase synthesis are described by Barany & Merrifield, *The Peptides: Analysis, Synthesis, Biology. Vol. 2:Special Methods in Peptide Synthesis*, Part A. pp. 3-284; Merrifield et al., *J. Am. Chem. Soc.* 85:2149-2156, 1963, and Stewart et al., *Solid Phase Peptide Synthesis, 2nd ed.*, Pierce Chem. Co., Rockford, Ill., 1984. Proteins of greater length may be synthesized by condensation of the amino and carboxyl termini of shorter fragments. Methods of forming peptide bonds by activation of a carboxyl terminal end (such as by the use of the coupling reagent N,N'-dicylohexylcarbodimide) are well known in the art.

It is disclosed herein that bispecific antibodies can be produced that bind different epitopes of the same antigen. These bispecific antibodies are of use for detection of IFG-II, diagnosis and treatment. Recombinant human antibodies and eAds that specifically bind an epitope of IGF-II with high affinity, in addition to those disclosed herein, can be isolated by screening of a recombinant combinatorial antibody library, preferably a scFv phage display library, prepared using cDNAs of the variable regions of heavy and light chains prepared from mRNA derived from human lymphocytes. Methodologies for preparing and screening such libraries are known in the art. There are commercially available kits for generating phage display libraries (for example, the Pharmacia Recombinant Phage Antibody System, catalog no. 27-9400-01; and the Stratagene SurfZAP™ phage display kit, catalog no. 240612). There are also other methods and reagents that can be used in generating and screening antibody display libraries (see, for example, U.S. Pat. No. 5,223, 409; PCT Publication No. WO 92/18619; PCT Publication No. WO 91/17271; PCT Publication No. WO 92/20791; PCT Publication No. WO 92/15679; PCT Publication No. WO 93/01288; PCT Publication No. WO 92/01047; PCT Publication No. WO 92/09690; Fuchs et al., Bio/Technology 9:1370-1372, 1991; Hay et al., Hum. Antibod. Hybridomas 3:81-85, 1992; Huse et al., Science 246:1275-1281, 1989; McCafferty et al., Nature 348:552-554, 1990; Griffiths et al. EMBO J 12:725-734, 1993)

In one embodiment, an antibody that specifically bind IGF-II, is first used to select human heavy and light chain sequences having similar binding activity toward IGF-II, such as using the epitope imprinting methods disclosed in PCT Publication No. WO 93/06213. The antibody libraries used in this method are scFv libraries prepared and screened, using methods such as those as described in PCT Publication No. WO 92/01047, McCafferty et al., Nature 348:552-554, 1990; and/or Griffiths et al., EMBO J 12:725-734, 1993 using human IGF-II as the antigen. These methods can be used to produce bispecific antibodies, wherein each component binds a different epitope of the same antigen.

Once initial human variable light chain ($V_L$) and variable heavy chain ($V_H$) segments are selected, "mix and match" experiments, in which different pairs of the initially selected $V_L$ and $V_H$ segments are screened for binding to IGF-II. These assays are performed to select $V_L/V_H$ pair combinations of interest. Additionally, to increase binding affinity of the antibody, the $V_L$ and $V_H$ segments can be randomly mutated, such as within H-CDR3 region or the L-CDR3 region, in a process analogous to the in vivo somatic mutation process responsible for affinity maturation of antibodies during a natural immune response. This in vitro affinity maturation can be accomplished by amplifying $V_H$ and $V_L$ regions using PCR primers complimentary to the H-CDR3 or L-CDR3, respectively. In this process, the primers have been "spiked" with a random mixture of the four nucleotide bases at certain positions such that the resultant PCR products encode $V_H$ and $V_L$ segments into which random mutations have been introduced into the $V_H$ and/or $V_L$ CDR3 regions. These randomly mutated $V_H$ and $V_L$ segments can be tested to determine the binding affinity for IGF-II, and to determine the epitope bound by the antibody.

Following screening and isolation of an antibody that binds IGF-II with high affinity from a recombinant immunoglobulin display library, nucleic acid encoding the selected antibody can be recovered from the display package (for example, from the phage genome) and subcloned into other expression vectors by standard recombinant DNA techniques, as described above. If desired, the nucleic acid can be further manipulated to create other antibody fragments, also as described below. To express a recombinant human antibody isolated by screening of a combinatorial library, the DNA encoding the antibody is cloned into a recombinant expression vector and introduced into mammalian host cells, as described above.

Compositions and Therapeutic Methods

Compositions are provided that include a therapeutically effective amount of one or more of the mAbs, antigen binding fragments, eAd or bispecific antibodies that specifically bind IGF-II that are disclosed herein in a carrier. Compositions are provided that include a therapeutically effective amount of one or more nucleic acids encoding the mAbs, antigen binding fragments, eAd or bispecific antibodies that specifically bind IGF-II in a carrier. The compositions can be prepared in unit dosage forms for administration to a subject. The amount and timing of administration are at the discretion of the treating physician to achieve the desired purposes. The antibody can be formulated for systemic or local (such as intra-tumor) administration. In one example, pharmaceutical composition is formulated for parenteral administration, such as intravenous administration. In other examples, the pharmaceutical composition is formulated for intramuscular administration.

The compositions for administration can include a solution of the mAb, eAd or bispecific antibody that specifically binds IGF-II, or a nucleic acid encoding the mAb, eAd or bispecific antibody, dissolved in a pharmaceutically acceptable carrier, such as an aqueous carrier. A variety of aqueous carriers can be used, for example, buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

A typical pharmaceutical composition for intravenous administration includes about 0.1 to 10 mg of antibody per subject per day. Dosages from 0.1 up to about 100 mg per subject per day may be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as *Remington's Pharmaceutical Science,* 19th ed., Mack Publishing Company, Easton, Pa. (1995).

Antibodies, antigen binding fragments, eAd and bispecific antibodies can be provided in lyophilized form and rehydrated with sterile water before administration, although they are also provided in sterile solutions of known concentration. The antibody solution is then added to an infusion bag containing 0.9% sodium chloride, USP, and typically administered at a dosage of from 0.5 to 15 mg/kg of body weight. Considerable experience is available in the art in the administration of antibody drugs, which have been marketed in the U.S. since the approval of RITUXAN® in 1997. Antibodies can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

A therapeutically effective amount of a nucleic acid encoding a mAb, eAd or bispecific antibody can also be administered to a subject. One approach to administration of nucleic acids is direct immunization with plasmid DNA, such as with a mammalian expression plasmid. The nucleotide sequence encoding the disclosed antibody can be placed under the control of a promoter to increase expression of the molecule. Immunization by nucleic acid constructs is well known in the art and taught, for example, in U.S. Pat. No. 5,643,578, and U.S. Pat. No. 5,593,972 and U.S. Pat. No. 5,817,637. U.S. Pat. No. 5,880,103 describes several methods of delivery of nucleic acids encoding immunogenic peptides or other antigens to an organism. The methods include liposomal delivery of the nucleic acids.

In another approach to using nucleic acids for immunization, a disclosed mAb, eAd or bispecific antibody can also be expressed by attenuated viral hosts or vectors or bacterial vectors. Recombinant vaccinia virus, adeno-associated virus (AAV), herpes virus, retrovirus, cytogmegalovirus, poxvirus or other viral vectors can be used to express the antibody. For example, vaccinia vectors and methods useful in immunization protocols are described in U.S. Pat. No. 4,722,848. BCG (Bacillus Calmette Guerin) provides another vector for expression of the disclosed antibodies (see Stover, *Nature* 351:456-460, 1991).

In one embodiment, a nucleic acid encoding a disclosed mAb, eAd or bispecific antibody is introduced directly into cells. For example, the nucleic acid can be loaded onto gold microspheres by standard methods and introduced into the skin by a device such as Bio-Rad's Heliosä Gene Gun. The nucleic acids can be "naked," consisting of plasmids under control of a strong promoter.

Typically, the DNA is injected into muscle, although it can also be injected directly into other sites. Dosages for injection are usually around 0.5 mg/kg to about 50 mg/kg, and typically are about 0.005 mg/kg to about 5 mg/kg (see, e.g., U.S. Pat. No. 5,589,466).

In another embodiment, a method is provided for inhibiting IGF-IR and/or insulin receptor (IR) activity by administering a mAb, eAd or bispecific antibody that specifically binds IGF-II, or a nucleic acid encoding the mAb, eAd or bispecific antibody, to a subject in need thereof. Thus, the antibodies disclosed herein can be used therapeutically. In one example, the subject is human. The antibody may be administered to a non-human mammal expressing an IGF-II with which the antibody cross-reacts (such as a primate, or a cynomolgus or rhesus monkey). It should be noted that animal models, such as primate models, can be useful for evaluating the therapeutic efficacy of antibodies of this invention.

The mAb, eAd, bispecific antibody or the nucleic acid encoding the mAb, eAd or bispecific antibody, can be administered to a subject having a disease or disorders in which the presence of high levels of IGF-1 receptor activity and/or high levels of IR receptor activity has been shown to be or is suspected of being either responsible for the pathophysiology of the disease or disorder or is a factor that contributes to a worsening of the disease or disorder. Accordingly, inhibition of IGF-1 receptor (IGF-IR) activity is expected to alleviate the symptoms and/or progression of the disorder. Such disorders may be evidenced, for example, by an increase in the levels of IGF-IR on the cell surface or by increased tyrosine autophosphorylation of IGF-IR in the affected cells or tissues of a subject suffering from the disorder.

The mAb, eAd, or bispecific antibody that specifically binds IGF-II can slow or inhibit the growth of cells, such as tumor cells, either in vivo or in vitro. In the in vivo applications, a therapeutically effective amount of an antibody is administered to a subject in an amount sufficient to inhibit growth of a tumor, or to inhibit a sign or a symptom of the tumor. Suitable subjects may include those with a tumor that expresses the IGF-1 receptor, such as those suffering from a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer. In one embodiment, a method is provided for the treatment of cancer such as brain, squamous cell, bladder, gastric, pancreatic, breast, head, neck, esophageal, prostate, colorectal, lung, renal, kidney, ovarian, gynecological or thyroid cancer.

Methods are also provided herein for the treatment of subjects having multiple myeloma, liquid tumor, liver cancer, thymus disorder, T-cell mediated auto-immune disease, endocronological disorder, ischemia, neurodegenerative disorder, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (such as uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (such as cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (such as renal cell carcinoma, carcinoma of the renal pelvis), or neoplasms of the central nervous system (such as primary CNS lymphoma, spinal axis tumors, brain stem gliomas or pituitary adenomas). In several examples, the human antibody that binds IGF-II is administered to a patient with prostate cancer, glioma or fibrosarcoma. In additional examples, a therapeutically effective amount of a mAb, eAd or bispecific antibody that specifically binds IGF-II, or a nucleic acid encoding the mAb, eAd or bispecific antibody, is administered to a subject with lung, breast, prostate or colon cancer. In other examples, the method causes the tumor not to increase in weight or volume or to decrease in weight or volume.

Amounts effective for this use will depend upon the severity of the disease and the general state of the patient's health. A therapeutically effective amount of the mAb, eAd, bispecific antibody, or the nucleic acid encoding the mAb, eAd or bispecific antibody, is that which provides either subjective relief of a symptom(s) or an objectively identifiable improvement as noted by the clinician or other qualified observer. In one example, the amount of the mAb, eAd, bispecific antibody, or a nucleic acid encoding the mAb, eAd or bispecific antibody, is sufficient to inhibit phosphorylation of the IGF-I receptor. These compositions can be administered in conjunction with another chemotherapeutic agent, either simultaneously or sequentially.

Many chemotherapeutic agents are presently known in the art. In one embodiment, the chemotherapeutic agents is selected from the group consisting of mitotic inhibitors, alkylating agents, anti-metabolites, intercalating antibiotics, growth factor inhibitors, cell cycle inhibitors, enzymes, topoisomerase inhibitors, anti-survival agents, biological response modifiers, anti-hormones, e.g. anti-androgens, and anti-angiogenesis agents.

Anti-angiogenesis agents, such as MMP-2 (matrix-metalloproteinase 2) inhibitors, MMP-9 (matrix-metalloproteinase 9) inhibitors, and COX-II (cyclooxygenase II) inhibitors, can be used in conjunction with a compound of the invention. Examples of useful COX-II inhibitors include CELEBREX™ (alecoxib), valdecoxib, and rofecoxib. Examples of useful matrix metalloproteinase inhibitors are described in PCT Publication No. WO 96/33172 (published Oct. 24, 1996), PCT Publication No. WO 96/27583 (published Mar. 7, 1996), European Patent Application No. 97304971.1 (filed Jul. 8, 1997), European Patent Application No. 99308617.2 (filed Oct. 29, 1999), PCT Publication No. WO 98/07697 (published Feb. 26, 1998), PCT Publication No WO 98/03516 (published Jan. 29, 1998), PCT Publication No WO 98/34918 (published Aug. 13, 1998), PCT Publication No WO 98/34915 (published Aug. 13, 1998), PCT Publication No WO 98/33768 (published Aug. 6, 1998), PCT Publication No WO 98/30566 (published Jul. 16, 1998), European Patent Publication 606,046 (published Jul. 13, 1994), European Patent Publication 931,788 (published Jul. 28, 1999), PCT Publication No WO 90/05719 (published May 31, 1990), PCT Publication No WO 99/52910 (published Oct. 21, 1999), PCT Publication No WO 99/52889 (published Oct. 21, 1999), PCT Publication No WO 99/29667 (published Jun. 17, 1999), PCT International Application No. PCT/IB98/01113 (filed Jul. 21, 1998), European Patent Application No. 99302232.1 (filed Mar. 25, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997). In one example, the MMP inhibitors do not induce arthralgia upon administration. In another example, the MMP inhibitor selectively inhibits MMP-2 and/or MMP-9 relative to the other matrix-metalloproteinases (such as MMP-1, MMP-3, MMP-4, MMP-5, MMP-6, MMP-7, MMP-8, MMP-10, MMP-11, MMP-12, and MMP-13). Some specific examples of MMP inhibitors of use are AG-3340, RO 32-3555, RS 13-0830, 3-[[4-(4-fluoro-phenoxy)-benzenesulfonyl]-(1-hydroxycarbamoyl-cyclopentyl)-amino]-propionic acid; 3-exo-3-[4-(4-fluoro-phenoxy)-benzenesulfonylamino]-8-oxa-bicyclo[3.2.1]octane-3-carboxylic acid hydroxyamide; (2R,3R) 1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]-tetrahydro-pyran-4-carboxylic acid hydroxyamide; 3-[[4-(4-fluoro-phenoxy)-benzenesulfonyl]-(1-hydroxycarbamoyl-cyclobutyl)-amino]-propionic acid; 4-[4-(4-chloro-phenoxy)-benzenesulfonylamino]-tetrahydro-pyran-4-carboxylic acid hydroxyamide; (R) 3-[4-(4-chloro-phenoxy)-benzenesulfonylamino]-tetrahydro-pyran-3-carboxylic acid hydroxyamide; (2R,3R) 1-[4-(4-fluoro-2-methyl-benzyloxy)-benzenesulfonyl]-3-hydroxy-3-methyl-piperidine-2-carboxylic acid hydroxyamide; 3-[[4-(4-fluoro-phenoxy)-benzenesulfonyl]-(1-hydroxycarbamoyl-1-methyl-ethyl)-amino]-propionic acid; 3-[[4-(4-fluoro-phenoxy)-benzenesulfonyl]-(4-hydroxycarbamoyl-tetrahydro-pyran-4-yl)-amino]-propionic acid; 3-exo-3-[4-(4-chloro-phenoxy)-benzenesulfonylamino]-8-oxaicyclo[3.2.1]octane-3-carboxylic acid hydroxyamide; 3-endo-3-[4-(4-fluoro-phenoxy)-benzenesulfonylamino]-8-oxa-icyclo[3.2.1]octane-3-carboxylic acid hydroxyamide; and (R) 3-[4-(4-fluoro-phenoxy)-benzenesulfonylamino]-tetrahydro-furan-3-carboxylic acid hydroxyamide; and pharmaceutically acceptable salts and solvates of said compounds.

The disclosed mAbs, and eAds, bispecific antibodies that specifically bind IGF-II, or nucleic acids encoding these mAbs, eAd or bispecific antibodies, can also be used with signal transduction inhibitors, such as agents that can inhibit EGF-R (epidermal growth factor receptor) responses, such as EGF-R antibodies, EGF antibodies, and molecules that are EGF-R inhibitors; VEGF (vascular endothelial growth factor) inhibitors, such as VEGF receptors and molecules that can inhibit VEGF; and erbB2 receptor inhibitors, such as organic molecules or antibodies that bind to the erbB2 receptor, for example, HERCEPTIN™ (Genentech, Inc.). EGF-R inhibitors are described in, for example in PCT Publication Nos. WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998). EGFR-inhibiting agents also include, but are not limited to, the mAbs C225 and anti-EGFR 22Mab (ImClone Systems Incorporated), ABX-EGF (Abgenix/Cell Genesys), EMD-7200 (Merck KgaA), EMD-5590 (Merck KgaA), MDX-447/H-477 (Medarex Inc. and Merck KgaA), and the compounds ZD-1834, ZD-1838 and ZD-1839 (AstraZeneca), PKI-166 (Novartis), PKI-166/CGP-75166 (Novartis), PTK 787 (Novartis), CP 701 (Cephalon), leflunomide (Pharmacia/Sugen), Cl-1033 (Warner Lambert Parke Davis), Cl-1033/PD 183,805 (Warner Lambert Parke Davis), CL-387,785 (Wyeth-Ayerst), BBR-1611 (Boehringer Mannheim GmbH/Roche), Naamidine A (Bristol Myers Squibb), RC-3940-II (Pharmacia), BIBX-1382 (Boehringer Ingelheim), OLX-103 (Merck & Co.), VRCTC-310 (Ventech Research), EGF fusion toxin (Seragen Inc.), DAB-389 (Seragen/Lilgand), ZM-252808 (Imperial Cancer Research Fund), RG-50864 (INSERM), LFM-A12 (Parker Hughes Cancer Center), WHI-P97 (Parker Hughes Cancer Center), GW-282974 (Glaxo), KT-8391 (Kyowa Hakko) and EGF-R Vaccine (York Medical/Centro de Immunologia Molecular (CIM)).

VEGF inhibitors, for example SU-5416 and SU-6668 (Sugen Inc.), SH-268 (Schering), and NX-1838 (NeXstar) can also be used in conjunction with an antibody that specifically binds IGF-II. VEGF inhibitors are described in, for example in PCT Publication No. WO 99/24440 (published May 20, 1999), PCT International Application PCT/IB99/00797 (filed May 3, 1999), PCT Publication No. WO 95/21613 (published Aug. 17, 1995), PCT Publication No. WO 99/61422 (published Dec. 2, 1999), U.S. Pat. No. 5,834,504 (issued Nov. 10, 1998), PCT Publication No. WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), PCT Publication No. WO 99/10349 (published Mar. 4, 1999), PCT Publication No. WO 97/32856 (published Sep. 12, 1997), PCT Publication No. WO 97/22596 (published Jun. 26, 1997), PCT Publication No. WO 98/54093 (published Dec. 3, 1998), PCT Publication No. WO 98/02438 (published Jan. 22, 1998), WO 99/16755 (published Apr. 8, 1999), and PCT Publication No. WO 98/02437 (published Jan. 22, 1998). Other examples of some specific VEGF inhibitors are IM862 (Cytran Inc.); anti-VEGF mAb of Genentech, Inc.; and angiozyme, a synthetic ribozyme from Ribozyme and Chiron. These and other VEGF inhibitors can be used in conjunction with an antibody that specifically binds IGF-II.

ErbB2 receptor inhibitors, such as GW-282974 (Glaxo Wellcome plc), and the mAbs AR-209 (Aronex Pharmaceuticals Inc.) and 2B-1 (Chiron), can furthermore be combined with the compound of the invention, for example those indicated in PCT Publication No. WO 98/02434 (published Jan. 22, 1998), PCT Publication No. WO 99/35146 (published Jul. 15, 1999), PCT Publication No. WO 99/35132 (published Jul. 15, 1999), PCT Publication No. WO 98/02437 (published Jan. 22, 1998), PCT Publication No. WO 97/13760 (published Apr. 17, 1997), PCT Publication No. WO 95/19970 (published Jul. 27, 1995), U.S. Pat. No. 5,587,458 (issued Dec. 24, 1996), and U.S. Pat. No. 5,877,305 (issued Mar. 2, 1999). ErbB2 receptor inhibitors of use are also described in U.S. Provisional Application No. 60/117,341, filed Jan. 27, 1999, and in U.S. Provisional Application No. 60/117,346, filed Jan. 27, 1999.

Single or multiple administrations of the compositions are administered depending on the dosage and frequency as required and tolerated by the patient. In any event, the composition should provide a sufficient quantity of at least one of the antibodies disclosed herein to effectively treat the patient. The dosage can be administered once but may be applied periodically until either a therapeutic result is achieved or until side effects warrant discontinuation of therapy. In one example, a dose of the antibody, antigen binding fragment, eAd or bispecific antibody is infused for thirty minutes every other day. In this example, about one to about ten doses can be administered, such as three or six doses can be administered every other day. In a further example, a continuous infusion is administered for about five to about ten days. The subject can be treated at regular intervals, such as monthly, until a desired therapeutic result is achieved. Generally, the dose is sufficient to treat or ameliorate symptoms or signs of disease without producing unacceptable toxicity to the patient. In one example, the dose is sufficient to decrease the phosphorylation of the IGF-I receptor.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 µm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example, Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992) both of which are incorporated herein by reference.

Polymers can be used for ion-controlled release of the compositions disclosed herein. Various degradable and non-degradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501, 728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat. No. 5,506,206; U.S. Pat. No. 5,271,961; U.S. Pat. No. 5,254, 342 and U.S. Pat. No. 5,534,496).

Diagnostic Methods and Kits

A method is provided herein for the detection of IGF-II in vitro or in vivo. In one example, expression of IGF-II is detected in a biological sample. The sample can be any sample, including, but not limited to, tissue from biopsies, autopsies and pathology specimens. Biological samples also include sections of tissues, for example, frozen sections taken for histological purposes. Biological samples further include body fluids, such as blood, serum, plasma, sputum, spinal fluid or urine. A biological sample is typically obtained from a mammal, such as a primate. In one embodiment, the primate is macaque, chimpanzee, or a human.

In several embodiments, a method is provided for detecting a malignancy such as a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer.

In additional embodiments, a method is provided for detecting multiple myeloma, liquid tumor, liver cancer, thymus disorder, T-cell mediated auto-immune disease, endocronological disorder, ischemia, neurodegenerative disorder, lung cancer, bone cancer, pancreatic cancer, skin cancer, cancer of the head and neck, cutaneous or intraocular melanoma, uterine cancer, ovarian cancer, rectal cancer, cancer of the anal region, stomach cancer, colon cancer, breast cancer, gynecologic tumors (such as uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (such as cancer of the thyroid, parathyroid or adrenal glands), sarcomas of soft tissues, cancer of the urethra, cancer of the penis, prostate cancer, chronic or acute leukemia, solid tumors of childhood, lymphocytic lymphomas, cancer of the bladder, cancer of the kidney or ureter (such as renal cell carcinoma, carcinoma of the renal pelvis), or neoplasms of the central nervous system (such as primary CNS lymphoma, spinal axis tumors, brain stem gliomas or pituitary adenomas). A method is also provided for determining the prognosis of a subject with any of the malignancies listed above.

Methods are provided for detecting IGF-II in a biological sample, wherein the method includes contacting a biological sample with an antibody, antigen binding fragment, eAd or bispecific antibody that binds IGF-II under conditions conductive to the formation of an immune complex, and detecting the immune complex, to detect the IGF-II in the biological sample. In one example, the detection of IGF-II in the sample indicates that the subject has a malignancy. In another example, the detection of IGF-II in the sample indicates that the subject is prone to metastasis.

In one embodiment, the human antibody that specifically binds IGF-II is directly labeled with a detectable label. In another embodiment, the human antibody that specifically binds IGF-II (the first antibody) is unlabeled and a second antibody or other molecule that can bind the antibody, antigen binding fragment, eAd or bispecific antibody that specifically binds IGF-II is labeled. As is well known to one of skill in the art, a second antibody is chosen that is able to specifically bind the specific species and class of the first antibody. For example, if the first antibody is a human IgG, then the secondary antibody may be an anti-human-IgG. Other molecules that can bind to antibodies include, without limitation, Protein A and Protein G, both of which are available commercially.

Suitable labels for the antibody, antigen binding fragment, eAd or bispecific antibody, and for the secondary antibody are described above, and include various enzymes, prosthetic groups, fluorescent materials, luminescent materials, magnetic agents and radioactive materials. Non-limiting examples of suitable enzymes include horseradish peroxidase, alkaline phosphatase, beta-galactosidase, or acetylcholinesterase. Non-limiting examples of suitable prosthetic group complexes include streptavidin/biotin and avidin/biotin. Non-limiting examples of suitable fluorescent materials include umbelliferone, fluorescein, fluorescein isothiocyanate, rhodamine, dichlorotriazinylamine fluorescein, dansyl chloride or phycoerythrin. A non-limiting exemplary luminescent material is luminol; a non-limiting exemplary a magnetic agent is gadolinium, and non-limiting exemplary radioactive labels include $^{125}I$, $^{131}I$, $^{35}S$ or $^{3}H$.

In an alternative embodiment, IGF-II can be assayed in a biological sample by a competition immunoassay utilizing IGF-II standards labeled with a detectable substance and an unlabeled human antibody that specifically binds IGF-II. In this assay, the biological sample, the labeled IGF-II standards and the antibody, antigen binding fragment, eAd or bispecific antibody that specifically bind IGF-II are combined and the amount of labeled IGF-II standard bound to the unlabeled antibody is determined. The amount of IGF-II in the biological sample is inversely proportional to the amount of labeled IGF-II standard bound to the antibody, antigen binding fragment, eAd or bispecific antibody that specifically binds IGF-II.

The immunoassays and method disclosed herein can be used for a number of purposes. In one embodiment, the antibody, antigen binding fragment, eAd or bispecific antibody that specifically binds IGF-II can be used to detect the production of IGF-II by cells in cell culture. In another embodiment, the antibody can be used to detect the amount of IGF-II in a biological sample. Increased expression of IGF-II is associated with several types of cancer, including a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer. Thus, the level of IGF-II can be used to diagnose, or determine the prognosis of, a sarcoma, leukemia, prostate cancer, lung cancer, breast cancer, colon cancer, stomach cancer, uterine cancer, cervical cancer, esophageal cancer, liver cancer, pancreatic cancer, kidney cancer, thyroid cancer, brain cancer, or an ovarian cancer, in a subject.

In one embodiment, a kit is provided for detecting IGF-II in a biological sample, such as a blood sample. Kits for detecting a polypeptide will typically comprise an antibody, antigen binding fragment, eAd or bispecific antibody that specifically binds IGF-II, such as any of the antibodies disclosed herein. In some embodiments, an antibody fragment, such as an Fv fragment is included in the kit. For in vivo uses, the antibody can be a scFv fragment. In a further embodiment, the antibody, antigen binding fragment, eAd or bispecific antibody is labeled (for example, with a fluorescent, radioactive, or an enzymatic label).

In one embodiment, a kit includes instructional materials disclosing means of use of an antibody that specifically binds IGF-II. The instructional materials may be written, in an electronic form (such as a computer diskette or compact disk) or may be visual (such as video files). The kits may also include additional components to facilitate the particular application for which the kit is designed. Thus, for example, the kit may additionally contain means of detecting a label (such as enzyme substrates for enzymatic labels, filter sets to detect fluorescent labels, appropriate secondary labels such as a secondary antibody, or the like). The kits may additionally include buffers and other reagents routinely used for the practice of a particular method. Such kits and appropriate contents are well known to those of skill in the art.

In one embodiment, the diagnostic kit comprises an immunoassay. Although the details of the immunoassays may vary with the particular format employed, the method of detecting IGF-II in a biological sample generally includes the steps of contacting the biological sample with an antibody which specifically reacts, under immunologically reactive conditions, to an IGF-II polypeptide. The antibody is allowed to specifically bind under immunologically reactive conditions to form an immune complex, and the presence of the immune complex (bound antibody) is detected directly or indirectly.

The antibody, antigen binding fragment, eAd or bispecific antibody can be conjugated to other compounds including, but not limited to, enzymes, magnetic beads, colloidal magnetic beads, haptens, fluorochromes, metal compounds, radioactive compounds or drugs. The antibodies can also be utilized in immunoassays such as but not limited to radioimmunoassays (RIAs), enzyme linked immunosorbant assays (ELISA), or immunohistochemical assays. The antibodies can also be used for fluorescence activated cell sorting (FACS). A FACS employs a plurality of color channels, low angle and obtuse light-scattering detection channels, and impedance channels, among other more sophisticated levels of detection, to separate or sort cells (see U.S. Pat. No. 5,061,620). Any of the antibodies, antigen binding fragments, eAds or bispecific antibodies that specifically bind IGF-IL as disclosed herein, can be used in these assays. Thus, the antibodies can be used in a conventional immunoassay, including, without limitation, an ELISA, an RIA, FACS, tissue immunohistochemistry, Western blot or immunoprecipitation.

The disclosure is illustrated by the following non-limiting Examples.

EXAMPLES

Soluble ligands are important targets for therapy of cancer and other diseases. Therapeutic mAbs against such ligands usually block the interaction with the corresponding receptors but do not enhance their removal from the circulation and can increase their half-lives because of the long half-lives of the antibodies. An approach is presented herein for irreversible and fast removal of such ligands from the circulation by mAbs binding to two or more nonoverlapping epitopes on the same molecule. The resulting multivalent Fc complexes can bind to cells expressing Fc gamma receptors (FcγRs) with high avidity leading to their fast removal from the circulation. Insulin-like growth factor II (IGF-II) is an example of a soluble ligand that is an important target for human cancer therapy.

Two mAbs, m610.27 and m630.3 were identified that specifically bind to nonoverlapping epitopes on IGF-II with high (nM) affinity. These mAbs were identified by panning and screening of a Fab and eAd libraries, respectively, followed by affinity maturation.

A bispecific antibody, m660, was also generated. M660 bound with pM affinity to IGF-II and inhibited the interaction of human IGF-II (hIGF-II) with a human cancer cell line MCF-7 and hIGF-II-stimulated cell growth. In the presence of hIGF-II, large complexes of m660 were formed that bound FcγRII-expressing BJAB cells more strongly than the monospecific antibody-hIGF-II complexes. When the complexes were incubated with PMA-stimulated macrophage-like FcγRI-expressing U937 cells on ice, m660 binding was barely or not detected while the binding could be partially restored by Cytochalasin D, a phagocytosis inhibitor, suggesting efficient removal of the complexes.

Thus, provided are a pair of mAbs, m610.27 and m630.3, that target nonoverlapping epitopes on a cancer-related soluble ligand. m660 is a bispecific antibody formed from m610.27 and/or m630.3. The antibodies, and the bi-specific antibodies disclosed herein, such as, but not limited to, m610.27, m630.3, and m660, can be used for the treatment of cancer and other chronic diseases affected by soluble ligands and for detection.

Example 1

Materials and Methods

Cells, Plasmids, Soluble Ligands, Antibodies, and Phagocytosis Inhibitors:

The BJAB cells were obtained from the National Cancer Institute, Frederick, Md. Plasmids pComb3X and pDR12 were provided by Scripps Research Institute, La Jolla, Calif. The 293 free style cells, human insulin, FITC-conjugated mouse anti-human CD32 (FcγRII) and CD16 (FcγRIII) antibodies, and streptavidin-PE conjugate were obtained from Invitrogen. Human IGF-I (hIGF-I) and IGF-II (hIGF-II), and mouse IGF-II (mIGF-II) were obtained from R&D systems. Horseradish peroxidase (HRP)-conjugated mouse anti-FLAG tag antibody, HRP-conjugated goat anti-human IgG (Fc-specific) antibody, HRP-conjugated rabbit anti-c-Myc tag antibody, FITC-conjugated goat F(ab')2 anti-human IgG (Fc-specific) antibody, and Cytochalasin D were products of Sigma-Aldrich.

Panning and Screening of a Human eAd Library:

To select antibodies that did not compete with a previously reported mAb, m610, biotinylated hIGF-II was used to pan a phage-displayed human eAd library m81 with size of 2.5× $10^{10}$ members (Chen et al., 2008, Proc Natl Acad Sci USA 105:17121-6). Briefly, the phage library (approximately $5\times10^{12}$ pfu) in 1 ml PBS containing 3% milk (MPBS) was mixed with 5 μg antigen. After a 1 hour (h) incubation at room temperature, 20 μl streptavidin-conjugated magnetic beads (Invitrogen, Carlsbad, Calif.) was added and incubated for 30 min. The beads were washed 5 times with PBS containing 0.05% Tween 20 (PBST) and used to infect exponentially growing TG1 cells. Bound phage was rescued by M13KO7 helper phage. The panning was repeated three times with a decrease of the antigen (1, 0.5, and 0.1 μg for the second, third and fourth round, respectively) and 10 times wash for each round. Clones that specifically bound to hIGF-II were identified from the fourth round of panning using soluble expression-based monoclonal ELISA (semELISA) as described previously (Chen et al., 2002, Mol Immunol 47:912-21).

Construction, Panning, and Screening of Random Mutagenesis and Light-Chain Shuffling Libraries:

To affinity mature m630, which was selected from the eAd library m81, a phage-displayed library of m630 mutants (approximately $10^9$ members) was constructed. To introduce point mutations, random DNA mutagenesis was performed with the GENE-MORPH® PCR Mutagenesis Kit (Stratagene, La Jolla, Calif.) according to the manufacturer's instructions. M630 gene fragments with mutations were PCR amplified by using m630-encoding plasmid as a template and primers m36F1 (sense) (SEQ ID NO: 19):(5'-TGGTTTCGC-TACCGT GGCCCAGGCGGCCCAGGTGCAGCTGGTG-3') and HISR (antisense) (SEQ ID NO: 20):(5'-GTCGC-CGTGGTGGTGGTGGTGGTGGC CGGCCTGGCCACTTG-3')

The PCR products were gel-purified, digested with SfiI, and gel-purified again. The purified fragments were then cloned into pComb3X linearized by SfiI. A phage library was prepared by electroporation of *Escherichia coli* (*E. coli*) strain TG1 electroporation-competent cells (Stratagene, La Jolla, Calif.) with desalted and concentrated ligation, as described previously (Chen et al., 2008, J Mol Biol 382:779-89). The phage library was panned against hIGF-II coated on 96-well plates as described (Feng et al., 2006, Mol Cancer Ther 5:114-20). Clones that bound to hIGF-II were identified from the third round of panning using semELISA.

To affinity mature m610, a light chain-shuffling Fab library (approximately $10^8$ members) was constructed based on the heavy chain of m610 according to the reported protocols (Zhu and Dimitrov, 2009, Methods Mol Biol 525: 129-42, xv). The light chain repertoire was harvested from a naive human Fab library ($5\times10^9$ members) constructed from peripheral blood B cells of 10 healthy donors (Zhu et al., 2006, J Virol 80: 891-9). The new library was panned against hIGF-II coated on 96-well plates and screened for higher affinity binders using monoclonal phage ELISA (mpELISA) as described previously (Zhu et al., supra).

m36F, (sense, SEQ ID NO: 21)
5'-TGGTTTCGCTACCGTGGCCCAGCCGGCCCAGGTGCAGCTGGTG-3';

m36R1, (antisense, SEQ ID NO: 22)
5'-GTGAGTTTTGTCGGGCCCTGAGGAGACGGTGAC-3';

bnIgG20H1, (sense, SEQ ID NO: 23)
5'-GTGTTCTAGAGCCGCCACCATGGAATGGAGCTGGGTCTTT CTCTTC-3';

bnIgG20H3, (antisense, SEQ ID NO: 24)
5'-GGAGTGGACACCTGTAGTTACTGACAGGAAGAAGAGAAA GAC-3';

m610.27H2, (sense, SEQ ID NO: 25)
5'ACTACAGGTGTCCACTCCCAAGTGCAGCTGGTGCAG-3';

m610.27H4, (antisense, SEQ ID NO: 26)
5'CCTTGGAGCTCGATCCGCCACCGCCAGAGCCACCTCCGCC TGAACCGCCTCCACCTCGTTTGATCTCCACC-3';

m36.4L2, (sense, SEQ ID NO: 27)
5'-CTTACAGATGCCAGATGTCAGGTGCAGCTGGTGCAG-3';

m36.4L4, (antisense, SEQ ID NO: 28)
5'-AGAGCCACCTCCGCCTGAACCGCCTCCACCTGAGGAGACGG TGACCAG-3';

bnIgG20L1, (sense, SEQ ID NO: 29)
5'-GTGTAAGCTTACCATGGGTGTGCCCACTCAGGTCCTGGGG TTGCTG-3';

bnIgG20L3, (antisense, SEQ ID NO: 30)
5'-ACATCTGGCATCTGTAAGCCACAGCAGCAGCAACCCCAG GAC-3';

CLF, (sense, SEQ ID NO: 31)
5'-TCAGGCGGAGGTGGCTCTGGCGGTGGCGGATCACGAACTGTGGC TGCACCA-3';

bnIgG20L4, (antisense, SEQ ID NO: 32)
5'-GTGTGAATTCATTAACACTCTCCCCTGTTGAA-3'.

IgG1 m610.27 was constructed by cloning Fab m610.27 into pDR12, which allows simultaneous expression of the heavy and light chains using protocols and reagents similar to those we used previously (Feng et al., 2006, supra). Briefly, the heavy chain variable region was first cloned into pDR12 via XbaI and SacI sites. The light chain sequence was then cloned into pDR12 via HindIII and EcoRI sites. To clone m630.3Fc, m630.3 gene fragment was PCR-amplified with primers m36F and m36R1, digested with SfiI and ApaI, and cloned into pSecTagB-Fc. To generate the bispecific antibody m660, the heavy chain leader peptide gene fragment (H-leader) and scFv m610.27 were PCR-amplified with primer pairs bnIgG20H1/bnIgG20H3 and m610.27H2/m610.27H4, respectively. H-leader was joined to scFv m610.27 by overlapping PCR performed in a volume of 50 μl by using both templates (in the same molarities) for 7 cycles in the absence of primers and 15 additional cycles in the presence of primers (500 pM of bnIgG20H1 and m610.27H4). The product was digested with XbaI and SacI, and cloned into vector pDR12. To fuse m630.3 to the N terminus of the human IgG1 light chain constant region, the light chain leader peptide (L-leader), m630.3, and the human IgG1 kappa light chain constant region (CK) were amplified by PCR with primer pairs bnIgG20L1/bnIgG20L3, m36.4L2/m36.4L4, and CLF/bnIgG20L4, respectively. L-leader was linked to m630.3 and CK by overlapping PCR with primers bnIgG20L1 and bnIgG20L4 as described above. The L-leader-m630.3-CK fragment was then digested with EcoRI and HindIII, and cloned into the pDR12 construct containing scFv m610.27.

Protein Expression and Purification:

Fabs and eAds were expressed in E. coli HB2151; all fusion proteins were produced in 293 free style cells, as described previously (Chen et al., 2008, Proc Natl Acad Sci USA 105:17121-6). The Fabs and eAds, which were tagged with hexahistidine at their C terminus, were purified from the soluble fraction of HB2151 periplasm by immobilized metal ion affinity chromatography (IMAC) using Ni-NTA resin (Qiagen, Valencia, Calif.) according to the manufacturer's protocols. The Fc-fusion proteins were purified from the 293 cell culture supernatants by Protein A Sepharose 4 Fast Flow (GE Healthcare, Piscataway, N.J.) column chromatography.

Size-Exclusion Chromatography:

A Superdex75 10/300 GL column (GE Healthcare, Piscataway, N.J.) was calibrated with protein molecular mass standards of 14 kDa ribonuclease A, 25 kDa chymotrypsin, 44 kDa ovalbumin, 67 kDa albumin, 158 kDa aldolase, 232 kDa catalase, 440 kDa ferritin and 669 kDa thyroglobulin. Proteins in PBS were loaded onto the pre-equilibrated column and eluted with PBS at 0.5 ml/min.

ELISA:

ELISA was performed as described previously (Chen et al., 2008, supra). Bound Fabs and eAds were detected by HRP-conjugated mouse anti-FLAG tag antibody. The antibody-Fc fusion proteins binding to IGF-II directly coated on 96-well plates were detected by HRP-conjugated goat anti-human IgG (Fc-specific) antibody. In the competition ELISA with IGF-II captured by IgG1s, bound m630.3Fc was detected by HRP-conjugated rabbit anti-c-Myc tag antibody. The half-maximal binding ($EC_{50}$) was calculated by fitting the data to the Langmuir adsorption isotherm.

Surface Plasmon Resonance (SPR) Analysis:

The binding kinetics of the antibodies was assessed by SPR analysis on Biacore X100 (GE Healthcare) according to the manufacturer's instructions. Briefly, antibodies were diluted in sodium acetate (pH 5.0) and immobilized directly onto a CM5 sensor chip with standard amine coupling method. The reference cell was injected with N-hydroxysuccinimide/1-ethyl-3-(3-dimethyaminopropy) carbodiimide and ethanolamine without injection of IGF-II. IGF-II was diluted with running buffer HBS-EP (100 mM HEPES, pH 7.4, 1.5 M NaCl, 30 mM EDTA, 0.5% surfactant 20). All analytes were tested at 10, 2.5, 0.63, 0.16, and 0.039 nM concentrations. The kinetic constants were calculated from the sensorgrams fitted with the monovalent binding model of the BiacoreX100 Evaluation software 2.0.

Flow Cytometry (FACS):

To measure the interactions of IGF-II with MCF-7, BJAB and U937 cells, biotinylated IGF-II was mixed with or without antibodies and added to approximately $10^5$ cells in 200 µl PBS containing 0.1% BSA (PBSA). After 1 h incubation on ice, the cells were washed twice and resuspended in 200 µl PBSA, and 1 µl streptavidin-PE conjugate was added. Following a 30-minute (min) incubation on ice, the cells were washed twice and then subjected to FACS. For detection of the expression of FcγRII, $10^5$ BJAB cells in 200 µl PBSA were mixed at different ratios (v/v) with FITC-conjugated mouse anti-human CD32 (FcγRII) antibody and incubated for 30 min at room temperature. The cells were washed twice with 200 µl PBSA and then used for FACS analysis. Antibodies binding to BJAB and U937 cells in the absence or presence of IGF-II were detected by FITC-conjugated goat F(ab')2 anti-human IgG (Fc-specific) antibody at a 1:200 dilution (v/v).

Phosphorylation Assays:

Antibody inhibition of IGF-II-stimulated receptor phosphorylation was measured as described previously (Feng et al., Mol Cancer Ther 5:114-20, 2006).

Cell Growth Assays:

The cell growth assay was performed as described previously (Feng, 2006, supra). Briefly, cells were seeded in 96-well plates at 10,000 per well in DMEM containing 10% fetal bovine serum (FBS). After overnight incubation, they were rinsed gently with serum-free medium twice. The cells were starved by adding 100 µl serum-free medium to each well and incubated at 37° C. for 6 h. The cells were then incubated with 10 nM hIGF-II with or without antibodies at various concentrations at 37° C. for 2 days. Live cells were determined by using the CELLTITER-GLO® Luminescent Cell Viability Assay System (Promega) and a LUMICOUNT® microplate luminometer (Turner Designs) according to the manufacturer's instructions.

Example 2

Selection and Affinity Maturation of IGF-II-Specific mAbs

A human mAb to IGF-II, designated m610, was identified which potently inhibited the IGF-IR and IR signaling pathways and cancer cell growth (Feng et al., 2006, supra). To increase its affinity, a Fab library with shuffled light chains was generated and panned against hIGF-II. The mutant selected, m610.27, had a light chain derived from the same germline (IGKV1-39*01) but with eight mutations compared to the original one; its heavy chain remained the same as m610 that was closest to the family IGHV1-46*01 (FIG. 1A). m610.27 in Fab format bound to hIGF-II with an $EC_{50}$ of 5 nM, four-fold lower than that (20 nM) of m610. An eAd, m630, was also identified by panning and screening a new large phage-displayed eAd library m81 with hIGF-II.

It was determined that m630 did not compete with m610 in binding to hIGF-II and mIGF-II in ELISA-based assays, and therefore could be used to generate bispecific antibodies with m610. m630 was affinity matured by panning and screening of a phage-displayed library generated by random mutagenesis with error-prone PCR. Four m630 mutants, designated m630.1, m630.3, m630.4 and m630.9, were selected (FIG. 1B). The highest affinity binder, m630.3, bound to hIGF-II with an $EC_{50}$ (2 nM), 25-fold lower than that (50 nM) of m630.

Example 3

Design and Characterization of Monospecific and Bispecific IgG1-Like mAbs

Fab m610.27 was converted to an $IgG_1$ (FIG. 2A), and a fusion protein (m630.3Fc) was made with m630.3 attached to the N terminus of a human IgG1 Fc via a hinge (FIG. 2B). An IgG1-like bispecific antibody, m660, was generated by fusing scFv m610.27 and m630.3 to the N termini of the heavy and light chain constant regions of a human IgG1, respectively, via a linker composed of three repeats of $G_4S$ (SEQ ID NO: 33) motif (FIG. 2C). The three proteins were well expressed and purified from 293 cell free style culture supernatants with yields of 2.0, 5.5, and 12 mg $l^{-1}$, respectively. They ran on a SDS-PAGE under reducing and nonreducing conditions with apparent molecular weights (aMWs) comparable with their calculated molecular weights (cMWs) or slightly higher due to glycosylation (FIG. 2D).

Binding activity and specificity of the antibodies were analyzed by ELISA and SPR. In ELISA assays, m630.3Fc bound to hIGF-II directly coated on 96-well plates with an $EC_{50}$ (0.6 nM), about six-fold lower than that (3.5 nM) of IgG1 m610.27 (FIG. 3A). m630.3Fc was cross-reactive against hIGF-I albeit with very low binding strength while no significant binding of IgG1 m610.27 to hIGF-I was observed at a concentration up to several µM. Neither m630.3Fc nor IgG1 m610.27 interacted measurably with human insulin.

Figure 3B:
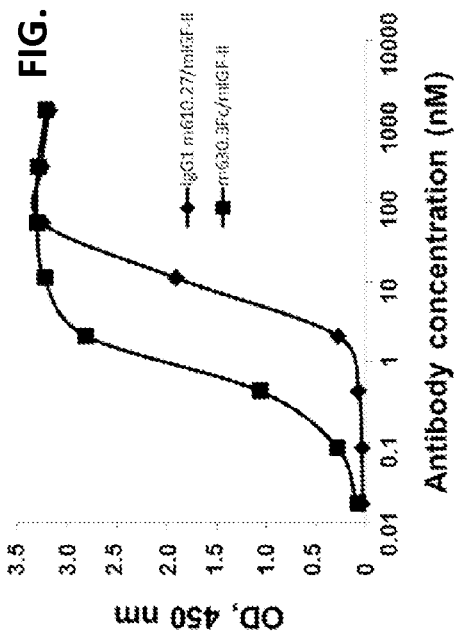
FIGS. 3A-3D: Binding and competition ELISA.
Figure 3A:
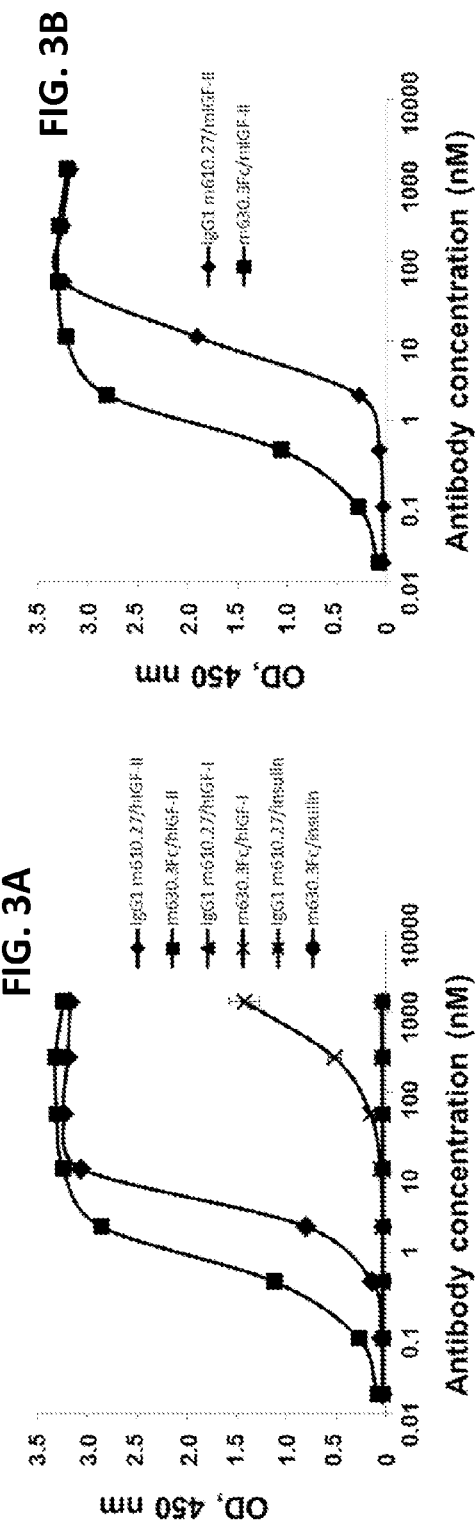
Figure 3D:
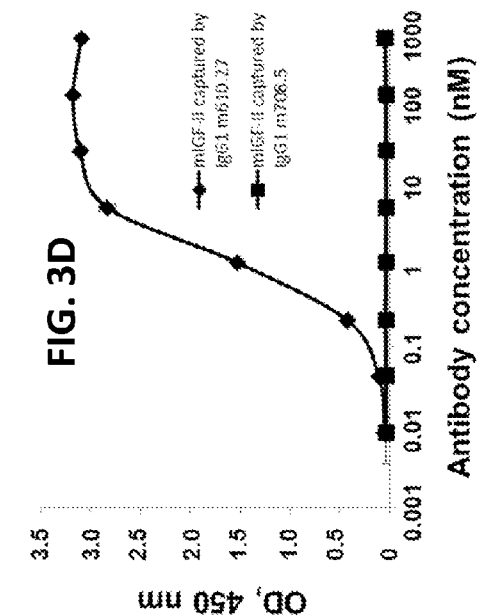
Figure 3C:
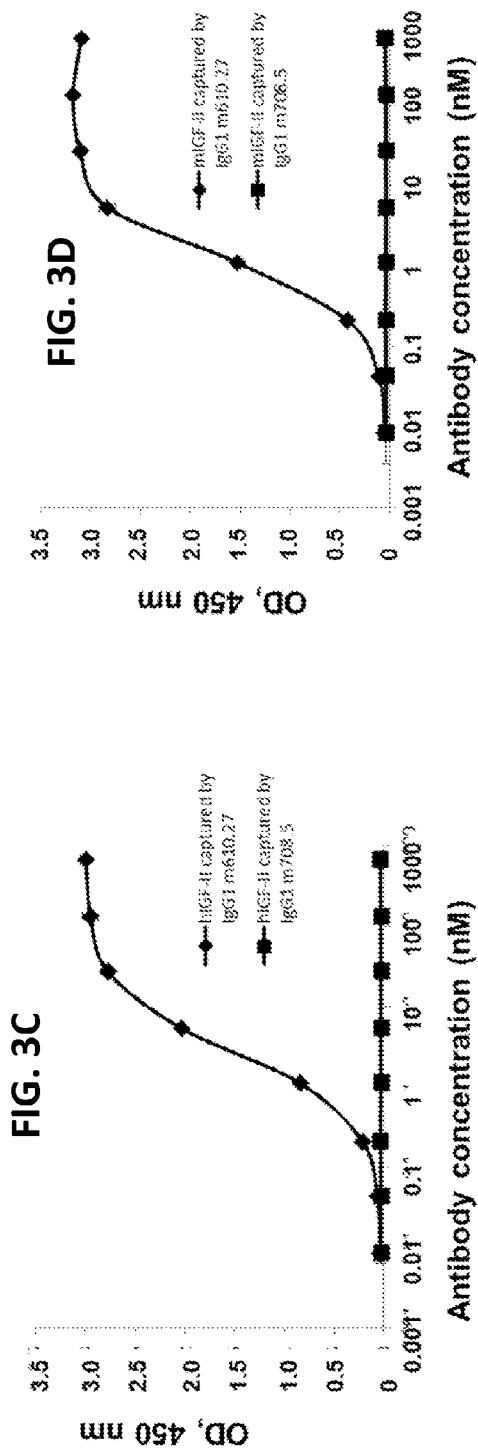

Both antibodies bound strongly to mIGF-II with an $EC_{50}$ of 0.7 nM for m630.3Fc and 8 nM for IgG1 m610.27 (FIG. 3B). As expected for non-competing antibodies, m630.3Fc also bound to hIGF-II (FIG. 3C) and mIGF-II (FIG. 3D) captured by IgG1 m610.27. In contrast, the antibodies didn't bind to IGF-II captured by IgG1 m708.5 (Zhao et al., Mol. Cancer. Ther., 2011), which is a human mAb cross-reactive to hIGF-I and hIGF-II that competes with both m630.3Fc and IgG1 m610.27 for binding to IGF-II, suggesting the competitive binding of m630.3Fc with IgG1 m708.5. m660 bound to hIGF-II with an $EC_{50}$ comparable to that of m630.3Fc and three-fold lower than that of IgG1 m610.7 (FIG. 4A). It exhibited stronger binding to long hIGF-II than the two monospecific antibodies likely due to avidity effects (FIG. 4B). In a SPR analysis, m660 associated rapidly and dissociated slowly with an equilibrium rate constant ($K_D$) of 136 pM (FIG. 4C).

Example 4

Figure 5:
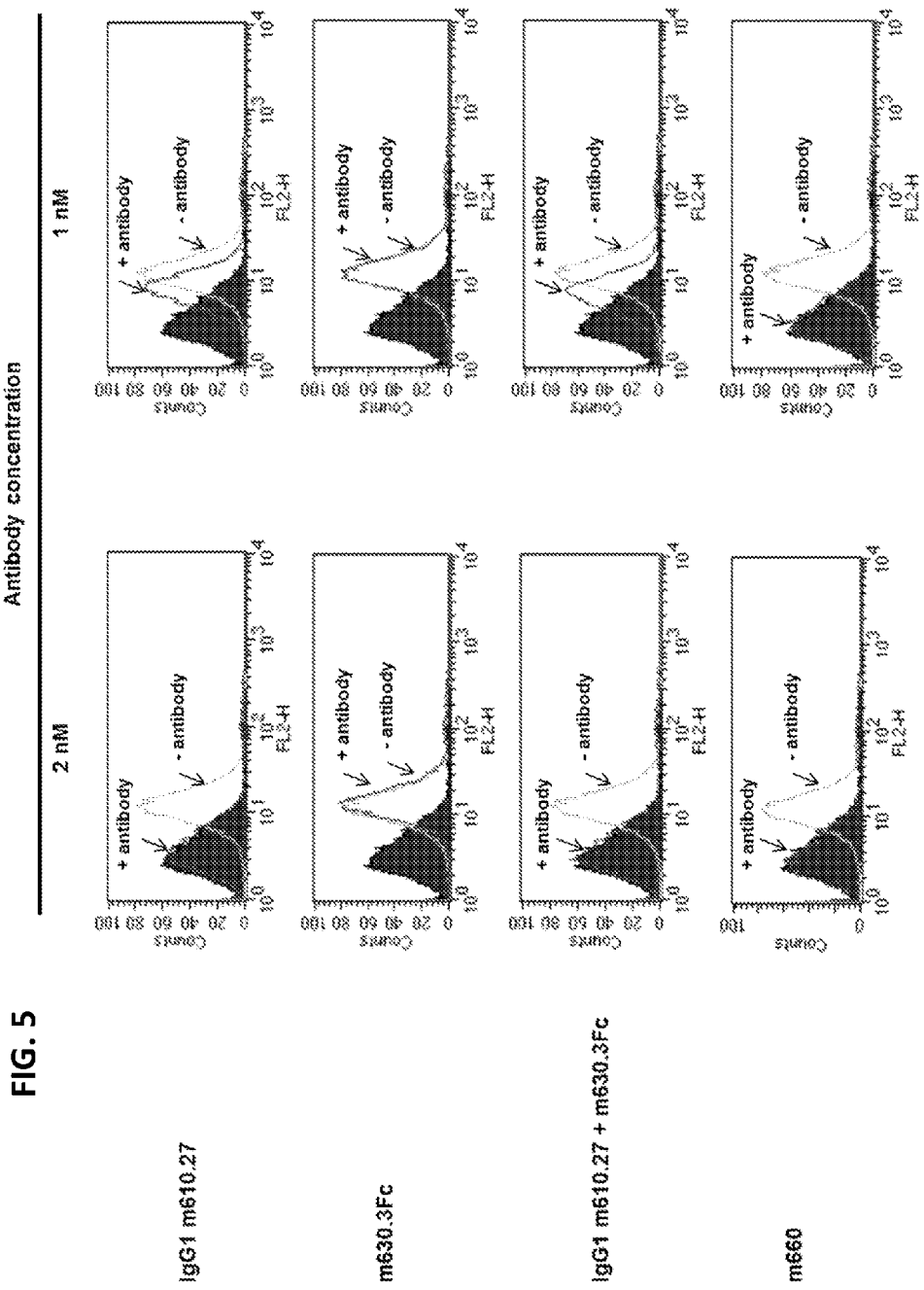
FIG. 5: Inhibition of FACS binding of hIGF-II to MCF-7 cells. MCF-7 cells were incubated with 1 nM biotinylated hIGF-II in the absence or presence of antibodies at various concentrations. Bound hIGF-II was detected by streptavidin-PE conjugate. Diagrams for reference cells, which were incubated with streptavidin-PE conjugate only, are with solid fill. Diagrams for cells incubated with or without antibodies are indicated by arrows.

Inhibition of hIGF-II Binding, hIGF-II-Stimulated IGF-IR and IR Phosphorylation, and Cancer Cell Proliferation IGF-IR and IR signaling is initiated by binding of their ligands. To test whether these antibodies could efficiently block the binding, MCF-7 cells, which are known to express high levels of IGF-IR, were incubated with 1 nM hIGF-II in the absence or presence of the antibodies at different concentrations. At 2 nM antibody concentration, m630.3Fc did not show any significant inhibition in a flow cytometry-based assay (FIG. 5). IgG1 m610.27, m660, and IgG1 m610.27 mixed with the same molar concentration of m630.3Fc completely inhibited the binding. At 1 nM antibody concentration, m660 still gave 100% inhibition whereas reduced inhibitory activity was observed with IgG1 m610.27 alone or a combination of IgG1 m610.27 and m630.3Fc.

Figure 6A:
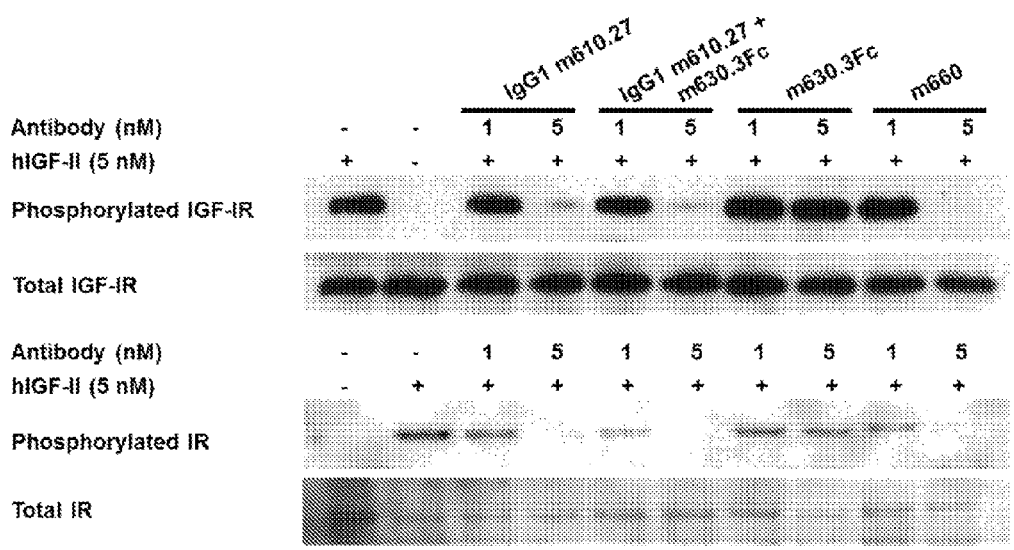
FIGS. 6A-6B: Inhibition of hIGF-II-stimulated IGF-IR and IR phosphorylation (FIG. 6A) and MCF-7 cell growth (FIG. 6B). The experiment was performed as described in the Examples section. In the cell growth assay, mean relative light units (RLU) for duplicate wells were determined. Relative growth activity of the cells was calculated by the following formula: (average RLU of hIGF-II-containing wells/average RLU of hIGF-II-free wells).

Upon ligand binding, IGF-IR undergoes autophosphorylation on tyrosine residues of the two β-subunits. To find out whether the antibodies could inhibit the transmembrane signaling mediated by the IGF-IR, the receptor phosphorylation was measured in MCF-7 cells. MCF-7 cells kept in serum-free DMEM displayed nondetectable phosphorylation of IGF-IR (FIG. 6A). After incubation with 5 nM hIGF-II for 20 minutes, the phosphorylation of IGF-IR was readily detected. In the presence of 5 nM m660, however, the phosphorylation was completely inhibited. IgG1 m610.27 and a mixture of IgG1 m610.27 with m630.3Fc at 5 nM also gave strong but incomplete inhibition. m630.3Fc showed no obvious inhibitory activity. When a 1 nM concentration was tested, no significant inhibition was seen in all cases. In addition to IGF-IR, IGF-II also binds to and activates IR. As shown in FIG. 6A, m660, IgG1 m610.7, or IgG1 m610.27 plus m630.3Fc at 5 nM completely blocked the effects of 5 nM hIGF-II on IR phosphorylation. Marked inhibition was also observed when 1 nM antibody was added. m630.3Fc appeared to slightly inhibit IR phosphorylation but its effect was not concentration-dependent.

Figure 6B:
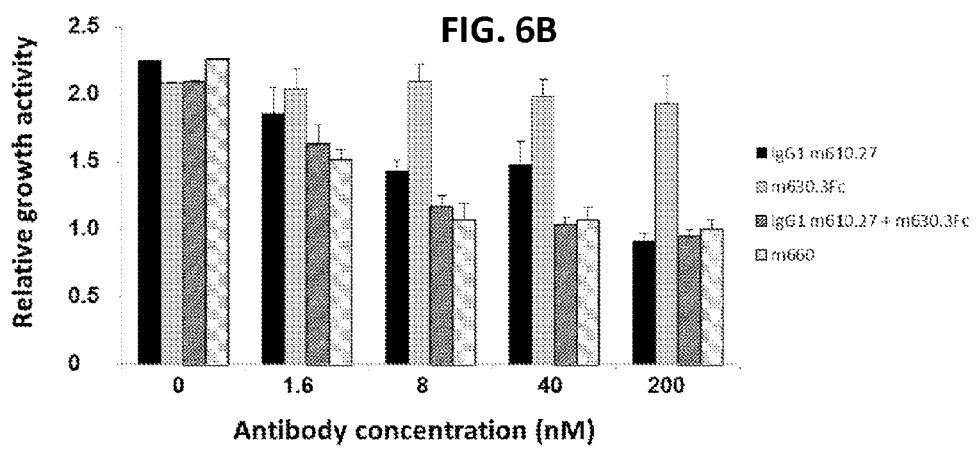

To determine that the antibodies could inhibit cell proliferation, MCF-7 cells were used in a cell growth assay. m630.3Fc at a concentration of 200 nM did not measurably affect the growth of the cells incubated with 10 nM hIGF-II (FIG. 6B). By comparison, m660 (P<0.001), IgG1 m610.27 alone (P=0.017) or mixed with of m630.3Fc at the same concentration (P=0.002) exhibited potent inhibitory activity with $IC_{50}$s of 1.6-8 nM; however, none of the three groups was significantly better than the others (P>0.05).

Example 5

Formation of Large Soluble Complexes and Enhanced Interactions of m660 with FcγRII-Expressing Cells Multivalent antibody-antigen interactions can induce formation of large immune complexes that either precipitate or remain soluble, depending on the degrees to which antigens are cross-linked by antibodies. To find whether large m660-IGF-II complexes could be formed, m660 was mixed with hIGF-II at different molar ratios and analyzed with size-exclusion chromatography. M660 alone was monomeric with a molecular weight (MW) of approximately 180 kDa (FIG. 7). With hIGF-II at the same molar concentration, about one half of m660 eluted as a dimer with a MW of approximately 380 kDa; a small percentage of the antibody was trimerized and eluted at a position corresponding to a MW of 580 kDa. When the m660:hIGF-II ratio was changed to 1:2, the antibody monomer became very minor and more trimer was observed. With a further increase of hIGF-II (ratio 1:4 or 1:8), almost all the antibody was in a trimeric or higher-order oligomeric state. In all cases, no precipitation was observed. Similar complexation was observed when m660 was replaced with $IgG_1$ m610.27 plus m630.3Fc at an equal molar concentration. However, when hIGF-II was mixed with either IgG1 m610.27 or m630.3Fc, they eluted at positions similar to those for the antibodies alone, suggesting no cross-linking between the monospecific antibodies and hIGF-II.

Large antibody-antigen complexes are able to trigger immune clearance mechanisms with the efficient recognition of multiple antibody Fc domains by effector cells expressing FcγRs due to avidity effects. To determine the effects of m660 oligomerization through cross-linking of IGF-II, BJAB cells, a human B cell line, were used as a model. According to a previous study (Fridman et al., 1991, FASEB J 5:2684-90), B cells express only FcγRII, which weakly ($K_D$ of approximately 1 µM) binds to naturally occurring antibodies with monovalent Fc. Therefore, differences in binding between m660-hIGF-II and monospecific antibody-hIGF-II complexes could be better observed by using this cell line. The results from flow cytometry analysis confirmed the expression of FcγRII using FITC-conjugated mouse anti-human CD32 (FcγRII) and CD16 (FcγRIII) antibodies (FIG. 8A). It was also found that BJAB cells did not significantly interact with hIGF-II alone at a concentration up to 1 µM (FIG. 8B).

Monospecific antibody IgG$_1$ m610.27 or m630.3Fc alone showed weak interactions with BJAB cells and their binding was not or only slightly altered when hIGF-II was added at a 1:2 molar ratio (antibody:hIGF-II) (FIG. 8C). As expected, the presence of hIGF-II at a 1:4 ratio dramatically enhanced the interactions of m660 or IgG$_1$ m610.27 plus m630.3Fc at an equal molar concentration with the cells (FIG. 8C). hIGF-II did not significantly affect the control antibodies IgG1 m102.4, a human mAb specific for henipa viruses (Zhu et al., 2006, J Virol 80:891-9) plus m36h1Fc, an antibody-Fc fusion protein against HW-1 (Berg et al., Eur. J. Immunol. 27: 1022-8, 1997), in binding to BJAB cells.

Example 6

Enhanced Phagocytosis of m660-hIGF-II Complexes by Macrophage-Like U937 Cells

Macrophage-mediated phagocytosis is one of the mechanisms for clearance of pathogens, cellular debris, and large immune complexes in vivo. To see whether m660-hIGF-II complexes could activate this mechanism, PMA-stimulated macrophage-like U937 cells, which express considerable levels of FcγRI, were used (FIG. 9A). The cells strongly interacted with hIGF-II alone at various concentrations suggesting the expression of IGF-IR and/or IR on the cell surface (FIG. 9B). To detect the interactions of the antibodies with or without hIGF-II, a FITC-conjugated goat F(ab')$_2$ anti-human IgG (Fc-specific) antibody was used. In a flow cytometry-based assay, in which the antibodies were incubated with the cells on ice for 1 hour, the presence of 20 nM hIGF-II slightly decreased or did not alter the binding of 10 nM IgG1 m610.27 and m630.3Fc to the cells (FIG. 9C). In contrast to the enhanced interactions with BJAB cells, however, increased binding of m660 at 10 nM to U937 cells was not observed in the presence of 40 nM hIGF-II. In the other assay, the antibodies were incubated with the cells at 37° C. for 2 hours, a condition under which phagocytosis is supposed to be more efficient than in the previous condition. While hIGF-II did not affect the interactions of the monospecific antibodies, m660 binding strength was decreased by approximately 80%. To further assess the possibility of phagocytosis, 50 μM Cytochalasin D, a phagocytosis inhibitor, was applied to both thermal conditions. As expected, binding of m660 was increased at 4° C. and partially restored at 37° C. while Cytochalasin D impaired the monospecific antibody binding in all cases.

Soluble ligands are important targets for therapy of many diseases. Antibodies directed against ligands are potent inhibitors of ligand-receptor interactions. Unfortunately, however, current therapeutic antibodies do not remove the ligands from the circulation in vivo while increasing their half-lives due to the long half-lives and high stability of the antibodies. IGF-I and IGF-II are small polypeptide ligands with MWs of approximately 7 kDa and have been implicated as essential mediators of the pathogenesis of some cancers. The way, in which they escape from the general clearance mechanisms (e.g., renal filtration) for small molecules and maintain high levels of serum concentration (mean values of 248 and 929 ng ml$^{-1}$, respectively), is to associate with members of a family of six IGF-binding proteins (IGFBPs). In this study, IGF-II was used as a model to test the hypothesis that mAbs targeting nonoverlapping epitopes on a single ligand molecule are capable of driving the formation of large soluble immune complexes, which, due to avidity effects of multivalent Fc, and can activate the immune clearance mechanisms in vivo leading to efficient and irreversible removal of ligands from the circulation and confer more effective protection from diseases.

The results from the size-exclusion chromatography showed that at an antibody-hIGF-II ratio of 1:4 or higher, almost all m660 was in trimeric or higher-order oligomeric states (FIG. 7). Previous efforts to select m610-noncompeting antibodies from several large Fab libraries had failed until the eAd libraries were utilized, from which m630 was successfully selected. This result suggests a higher likelihood of selection of such binders from libraries composed of smaller antibodies. Second, the angles at which the second antibody can approach IGF-II would be limited and most likely are opposite to that of the first antibody. m660 was generated with both m610.27 and m630.3 at the N termini. It is possible that complexation can be strengthened by fusing an antibody to the C terminus of Fc.

The efficient recognition and uptake of large m660-hIGF-II complexes were demonstrated by using BJAB cells, a human B lymphoma cell line, and PMA-stimulated U937 cells, a macrophage-like human leukemic monocyte lymphoma cell line, respectively (FIGS. 9 and 10). Although mammalian B cells lack phagocytic capabilities, previous studies showed that they could preferentially uptake antigen-antibody complexes through FcγRII-mediated endocytosis (Berg et al., supra, 1997). Moreover, there is supporting evidence that B cells evolve from an ancestral phagocytic cell type (Li et al., Nat Immunol 7:1116-24, 2006). These results indicate a previously unknown function of B cells in the innate immunity of mammals. Other cell types expressing FcγRII or FcγRIII may also have similar activities especially when large immune complexes with multivalent Fc are presented.

Without being bound by theory, bispecific antibodies targeting nonoverlapping epitopes on a ligand can not only cross-link the ligand but also bind to it better than monospecific antibodies due to avidity effects. Specifically, m660 bound to long hIGF-II with an EC$_{50}$ lower than those of IgG1 m610.27 and m630.3Fc (FIG. 4B); and m660 inhibited the interaction of hIGF-II to MCF-7 cells (FIG. 5) and IGF-IR phosphorylation (FIG. 6A) relatively more strongly than the monospecific antibodies alone or in combination. m660 did not show enhanced binding to the matured hIGF-II in the ELISA assay (FIG. 4A), most likely because one of the two antibody-binding sites on a single hIGF-II molecule was not accessible when hIGF-II was coated on the 96-well plates.

The presently disclosed antibodies do not bind IR (FIG. 3A) and therefore, should not be able to block insulin-IR interactions. These antibodies also should not affect IGF-I signaling. Although m630.3Fc was cross-reactive with hIGF-I, the affinity (EC$_{50}$>1 μM) was much lower than that (K$_D$ of approximately 1 nM) between hIGF-I and IGF-IR. Moreover, m630.3Fc did not show significant inhibitory activity against the interaction of hIGF-II with MCF-7 cells and hIGF-II-mediated phosphorylation of IGF-IR and IR (FIG. 5). Because hIGF-I and hIGF-II are of high similarity in both sequences and structures, it is unlikely that m630.3Fc would target the receptor-binding site of IGF-I. The antibodies disclosed herein can be used alone or in combinations with IGF-IR-directed agents and other anti-tumor therapeutics.

In view of the many possible embodiments to which the principles of our invention may be applied, it should be recognized that illustrated embodiments are only examples of the invention and should not be considered a limitation on the scope of the invention. Rather, the scope of the invention is defined by the following claims. We therefore claim as our invention all that comes within the scope and spirit of these claims.

We claim:

1. An isolated monoclonal antibody, or an antigen binding fragment thereof, wherein the monoclonal antibody or the antigen binding fragment comprises:
    a heavy chain variable domain comprising heavy chain complementarity determining regions (H-CDR)1, H-CDR2 and H-CDR3; and
    a light chain variable domain comprising light chain complementarity determining regions (L-CDR)1, L-CDR2 and L-CDR3,
    wherein the H-CDR1 comprises amino acids 26 to 33 of the amino acid sequence set forth as SEQ ID NO: 1, the H-CDR2 comprises amino acids 51 to 58 of the amino acid sequence set forth as SEQ ID NO: 1, and the H-CDR3 comprises amino acids 97 to 109 of the amino acid sequence set forth as SEQ ID NO: 1,
    wherein the L-CDR1 comprises amino acids 27 to 32 of the amino acid sequence set forth as SEQ ID NO: 2, the L-CDR2 comprises amino acids 50 to 52 of the amino acid sequence set forth as SEQ ID NO: 2, and the L-CDR3 comprises amino acids 89 to 98 of the amino acid sequence set forth as SEQ ID NO: 2, and
    wherein the monoclonal antibody specifically binds a first epitope of insulin like growth factor (IGF)-II.

2. The isolated monoclonal antibody or the antigen binding fragment of claim 1, wherein:
    a) the heavy chain variable domain comprises the amino acid sequence set forth as SEQ ID NO: 1;
    b) the light chain variable domain comprises the amino acid sequence set forth as SEQ ID NO: 2; or
    c) the heavy chain variable domain comprises the amino acid sequence set forth as SEQ ID NO: 1 and the light chain variable domain comprises the amino acid sequence set forth as SEQ ID NO: 2.

3. The isolated monoclonal antibody or the antigen binding fragment of claim 1, comprising a human framework region.

4. The antigen binding fragment of claim 1, wherein the antigen binding fragment is an scFv.

5. A composition comprising
the monoclonal antibody or antigen binding fragment of claim 1, and
a pharmaceutically acceptable carrier.

6. A method of decreasing the proliferation of breast cancer cells in response to IGF-II, comprising
contacting the breast cancer cells in vitro with an effective amount of the composition of claim 5,
thereby decreasing the proliferation of the breast cancer cells in response to IGF-II.

7. The monoclonal antibody of claim 1, further comprising a label.

8. A method of reducing the proliferation of breast cancer cells in a subject, comprising administering to the subject a therapeutically effective amount of the monoclonal antibody or antigen binding fragment of claim 1, thereby reducing the proliferation of the breast cancer cells in the subject.

9. A method of detecting insulin like growth factor (IGF)-II in a biological sample from a subject, comprising
contacting the biological sample with the monoclonal antibody or antigen binding fragment of claim 1 under conditions sufficient to form an immune complex; and
detecting the presence of the immune complex,
wherein the presence of the immune complex indicates that-IGF-II is present in the biological sample.

10. The method of claim 9, wherein the monoclonal antibody or the antigen binding fragment is directly labeled.

11. The method of claim 9, wherein the biological sample is a blood, urine, biopsy, serum, sputum, plasma, or cerebral spinal fluid sample.

12. The method of claim 9, wherein the monoclonal antibody or antigen binding fragment is labeled.

13. A method of inhibiting phosphorylation of the insulin-like growth factor-I receptor, comprising
contacting a breast cancer cell
expressing the insulin-like growth factor-I receptor in vitro with an effective amount of monoclonal antibody or antigen binding fragment of claim 1,
thereby inhibiting the phosphorylation of the insulin-like growth factor-I receptor.

14. An isolated bispecific antibody comprising a first monoclonal antibody or antigen binding fragment thereof that specifically binds a first epitope of IGF-II, and a second monoclonal antibody, antigen binding fragment thereof or single domain antibody, wherein the second monoclonal antibody, antigen binding fragment thereof or single domain antibody specifically binds a second epitope of IGF-II,
wherein the first monoclonal antibody or antigen binding fragment comprises a heavy chain variable domain comprising heavy chain complementarity determining regions (H-CDR)1, H-CDR2 and H-CDR3 and a light chain variable domain comprising light chain complementarity determining regions (L-CDR)1, L-CDR2 and L-CDR3, wherein the H-CDR1 comprises amino acids 26 to 33 of the amino acid sequence set forth as SEQ ID NO: 1, the H-CDR2 comprises amino acids 51 to 58 of the amino acid sequence set forth as SEQ ID NO: 1, and the H-CDR3 comprises amino acids 97 to 109 of the amino acid sequence set forth as SEQ ID NO: 1, and wherein the L-CDR1 comprises amino acids 27 to 32 of the amino acid sequence set forth as SEQ ID NO: 2, the L-CDR2 comprises amino acids 50 to 52 of the amino acid sequence set forth as SEQ ID NO: 2, and the L-CDR3 comprises amino acids 89 to 98 of the amino acid sequence set forth as SEQ ID NO: 2; and
wherein the bispecific antibody specifically binds insulin like growth factor (IGF)-II.

15. The isolated bispecific monoclonal antibody of claim 14, wherein the second antibody is the single domain antibody, and wherein the first epitope and the second epitope are different.

16. The isolated bispecific antibody of claim 15, wherein the single domain antibody comprises heavy chain complementarity determining regions (H-CDR)1, H-CDR2 and H-CDR3, wherein the H-CDR1 comprises the amino acid sequence set forth as amino acids 26 to 33 of the amino acid sequence set forth as SEQ ID NO: 5, the H-CDR2 comprises amino acids 51 to 58 of the amino acid sequence set forth as SEQ ID NO: 5, and the H-CDR3 comprises amino acids 97 to 117 of the amino acid sequence set forth as SEQ ID NO: 5, and wherein:
(a) residue 30 of SEQ ID NO: 5 is D, residue 104 of SEQ ID NO: 5 is S, residue 107 of SEQ ID NO: 5 is S, and residue 113 of SEQ ID NO: 5 is Y;
(b) residue 30 of SEQ ID NO: 5 is D, residue 104 of SEQ ID NO: 5 is R, residue 107 of SEQ ID NO: 5 is S, and residue 113 of SEQ ID NO: 5 is H;
(c) residue 30 of SEQ ID NO: 5 is D, residue 104 of SEQ ID NO: 5 is R, residue 107 of SEQ ID NO: 5 is R, and residue 113 of SEQ ID NO: 5 is Y;
(d) residue 30 of SEQ ID NO: 5 is G, residue 104 of SEQ ID NO: 5 is S, residue 107 of SEQ ID NO: 5 is R, and residue 113 of SEQ ID NO: 5 is Y; or
(e) residue 30 of SEQ ID NO: 5 is D, residue 104 of SEQ ID NO: 5 is S, residue 107 of SEQ ID NO: 5 is R, and residue 113 of SEQ ID NO: 5 is Y.

17. The isolated bispecific antibody of claim 16, wherein residue 30 of SEQ ID NO: 5 is D, residue 104 of SEQ ID NO: 5 is R, residue 107 of SEQ ID NO: 5 is R, and residue 113 of SEQ ID NO: 5 is Y.

18. The isolated bispecific antibody of claim 16, wherein the single domain antibody comprises the amino acid sequence set forth as SEQ ID NO: 5, and wherein
(a) residue 30 of SEQ ID NO: 5 is D, residue 76 of SEQ ID NO: 5 is K, residue 104 of SEQ ID NO: 5 is 5, residue 107 of SEQ ID NO: 5 is 5, and residue 113 of SEQ ID NO: 5 is
(b) residue 30 of SEQ ID NO: 5 is D, residue 76 of SEQ ID NO: 5 is K, residue 104 of SEQ ID NO: 5 is R, residue 107 of SEQ ID NO: 5 is S, and residue 113 of SEQ ID NO: 5 is H;
(c) residue 30 of SEQ ID NO: 5 is D, residue 76 of SEQ ID NO: 5 is K, residue 104 of SEQ ID NO: 5 is R, residue 107 of SEQ ID NO: 5 is R, and residue 113 of SEQ ID NO: 5 is Y;
(d) residue 30 of SEQ ID NO: 5 is G, residue 76 of SEQ ID NO: 5 is K, residue 104 of SE ID NO: 5 is S residue 107 of SEQ ID NO: 5 is R, and residue 113 of SE ID NO: 5 is Y; or
(e) residue 30 of SEQ ID NO: 5 is D, residue 76 of SEQ ID NO: 5 is K, residue 104 of SEQ ID NO: 5 is S, residue 107 of SEQ ID NO: 5 is R, and residue 113 of SEQ ID NO: 5 is Y.

19. A method of decreasing the proliferation of breast cancer cells in response to IGF-II, comprising contacting the breast cancer cells in vitro with an effective amount of the bispecific antibody of claim 18 thereby decreasing the proliferation of the breast cancer cells in response to IGF-II.

20. A method of reducing the proliferation of breast cancer cells in a subject, comprising administering to the subject a therapeutically effective amount of the bispecific antibody of claim 16, thereby reducing the proliferation of the breast cancer cells in the subject.

21. A composition comprising the bispecific antibody of claim 16 and a pharmaceutically acceptable carrier.

22. A method of decreasing the proliferation of breast cancer cells in response to IGF-II, comprising
contacting the breast cancer cells in vitro with an effective amount of the bispecific antibody of claim 16,
thereby decreasing the proliferation of the breast cancer cells in response to IGF-II.

23. A method of detecting insulin like growth factor (IGF)-II in a biological sample, comprising
contacting the biological sample with the bispecific antibody of claim 16 under conditions sufficient to form an immune complex; and
detecting the presence of the immune complex
wherein the presence of the immune complex indicates that-IGF-II is present in the biological sample.

24. The method of claim 23, wherein the biological sample is a blood, urine, biopsy, serum, sputum, plasma, or cerebral spinal fluid sample.

25. A composition comprising the bispecific antibody of claim 14 and a pharmaceutically acceptable carrier.

26. A single domain antibody, comprising heavy chain complementarity determining regions (H-CDR)1, H-CDR2 and H-CDR3, wherein the H-CDR1 comprises amino acids 26 to 33 of the amino acid sequence set forth as SEQ ID NO: 5, the H-CDR2 comprises amino acids 51 to 58 of the amino acid sequence set forth as SEQ ID NO: 5, and the H-CDR3 comprises amino acids 97 to 117 of the amino acid sequence set forth as SEQ ID NO: 5, wherein
 (a) residue 30 of SEQ ID NO: 5 is D, residue 104 of SEQ ID NO: 5 is S, residue 107 of SEQ ID NO: 5 is S, and residue 113 of SEQ ID NO: 5 is Y;
 (b) residue 30 of SEQ ID NO: 5 is D, residue 104 of SEQ ID NO: 5 is R, residue 107 of SEQ ID NO: 5 is S, and residue 113 of SEQ ID NO: 5 is H;
 (c) residue 30 of SEQ ID NO: 5 is D, residue 104 of SEQ ID NO: 5 is R, residue 107 of SEQ ID NO: 5 is R, and residue 113 of SEQ ID NO: 5 is Y;
 (d) residue 30 of SEQ ID NO: 5 is G, residue 104 of SEQ ID NO: 5 is S, residue 107 of SEQ ID NO: 5 is R, and residue 113 of SEQ ID NO: 5 is Y; or
 (e) residue 30 of SEQ ID NO: 5 is D, residue 104 of SEQ ID NO: 5 is S, residue 107 of SEQ ID NO: 5 is R, and residue 113 of SEQ ID NO: 5 is Y, wherein the single domain antibody binds a first epitope of insulin like growth factor (IGF)-II, and
wherein the single domain antibody specifically binds an epitope of insulin like growth factor-II.

27. The single domain antibody of claim 26, comprising the amino acid sequence set forth as SEQ ID NO: 5 wherein
 (a) residue 30 of SEQ ID NO: 5 is D, residue 76 of SEQ ID NO: 5 is K, residue 104 of SEQ ID NO: 5 is S, residue 107 of SEQ ID NO: 5 is S, and residue 113 of SEQ ID NO: 5 is Y;
 (b) residue 30 of SEQ ID NO: 5 is D, residue 76 of SEQ ID NO: 5 is R, residue 104 of SEQ ID NO: 5 is R, residue 107 of SEQ ID NO: 5 is S, and residue 113 of SEQ ID NO: 5 is H;
 (c) residue 30 of SEQ ID NO: 5 is D, residue 76 of SEQ ID NO: 5 is K, residue 104 of SEQ ID NO: 5 is R, residue 107 of SEQ ID NO: 5 is R, and residue 113 of SE ID NO: 5 is Y;
 (d) residue 30 of SEQ ID NO: 5 is G, residue 76 of SEQ ID NO: 5 is K, residue 104 of SEQ ID NO: 5 is S, residue 107 of SEQ ID NO: 5 is R, and residue 113 of SEQ ID NO: 5 is Y; or
 (e) residue 30 of SEQ ID NO: 5 is D, residue 76 of SEQ ID NO: 5 is K, residue 104 of SEQ ID NO: 5 is S, residue 107 of SEQ ID NO: 5 is R, and residue 113 of SEQ ID NO: 5 is Y.

28. The single domain antibody of claim 26, wherein residue 30 of SEQ ID NO: 5 is D, residue 104 of SEQ ID NO: 5 is R, residue 107 of SEQ ID NO: 5 is R, and residue 113 of SEQ ID NO: 5 is Y.

29. A composition, comprising:
the single domain antibody of claim 26, and
a pharmaceutically acceptable carrier.

30. A method of detecting insulin like growth factor (IGF)-II in a biological sample, comprising contacting the biological sample with the single domain antibody of claim 26 under conditions sufficient to form an immune complex; and detecting the presence of the immune complex wherein the presence of the immune complex -indicates that-IGF-II is present in the biological sample.

31. The method of claim 30, wherein the single domain antibody is labeled.

32. The method of claim 30, wherein the biological sample is a blood, urine, biopsy, serum, sputum, plasma, or cerebral spinal fluid sample.

33. An isolated bispecific antibody comprising a single domain antibody that specifically binds a first epitope of IGF-II and a second monoclonal antibody or antigen binding fragment thereof that specifically binds a second epitope of IGF-II,
wherein the single domain antibody comprises heavy chain complementarity determining regions (H-CDR)1, H-CDR2 and H-CDR3, wherein the H-CDR1 comprises amino acids 26 to 33 of the amino acid sequence set forth as SEQ ID NO: 5, the H-CDR2 comprises amino acids 51 to 58 of the amino acid sequence set forth as SEQ ID NO: 5, and the H-CDR3 comprises amino acids 97 to 117 of the amino acid sequence set forth as SEQ ID NO: 5, wherein
 (a) residue 30 of SEQ ID NO: 5 is D, residue 104 of SEQ ID NO: 5 is S, residue 107 of SEQ ID NO: 5 is S, and residue 113 of SEQ ID NO: 5 is Y;
 (b) residue 30 of SEQ ID NO: 5 is D, residue 104 of SEQ ID NO: 5 is R, residue 107 of SEQ ID NO: 5 is S, and residue 113 of SEQ ID NO: 5 is H;
 (c) residue 30 of SEQ ID NO: 5 is D, residue 104 of SEQ ID NO: 5 is R, residue 107 of SEQ ID NO: 5 is R, and residue 113 of SEQ ID NO: 5 is Y;
 (d) residue 30 of SEQ ID NO: 5 is G, residue 104 of SEQ ID NO: 5 is S, residue 107 of SEQ ID NO: 5 is R, and residue 113 of SEQ ID NO: 5 is Y; or
 (e) residue 30 of SEQ ID NO: 5 is D, residue 104 of SEQ ID NO: 5 is S, residue 107 of SEQ ID NO: 5 is R, and residue 113 of SEQ ID NO: 5 is Y;
and wherein the bispecific antibody specifically binds IGF-II, and wherein the first epitope and the second epitope are different.

34. The isolated bispecific antibody of claim 33, wherein the single domain antibody comprises the amino acid sequence set forth as SEQ ID NO: 5, and wherein:
 (a) residue 30 of SEQ ID NO: 5 is D, residue 76 of SEQ ID NO: 5 is K, residue 104 of SEQ ID NO: 5 is S, residue 107 of SEQ ID NO: 5 is S, and residue 113 of SEQ ID NO: 5 is Y;
 (b) residue 30 of SEQ ID NO: 5 is D, residue 76 of SEQ ID NO: 5 is R, residue 104 of SEQ ID NO: 5 is R, residue 107 of SEQ ID NO: 5 is S, and residue 113 of SEQ ID NO: 5 is H;

(c) residue 30 of SEQ ID NO: 5 is D, residue 76 of SEQ ID NO: 5 is K, residue 104 of SEQ ID NO: 5 is R, residue 107 of SEQ ID NO: 5 is R, and residue 113 of SEQ ID NO: 5 is Y;

(d) residue 30 of SEQ ID NO: 5 is G, residue 76 of SEQ ID NO: 5 is K, residue 104 of SEQ ID NO: 5 is S, residue 107 of SEQ ID NO: 5 is R, and residue 113 of SEQ ID NO: 5 is Y; or (e) residue 30 of SEQ ID NO: 5 is D, residue 76 of SEQ ID NO: 5 is K, residue 104 of SEQ ID NO: 5 is S, residue 107 of SEQ ID NO: 5 is R, and residue 113 of SEQ ID NO: 5 is Y.

35. The isolated bispecific antibody of claim 33, comprising the antigen binding fragment of the monoclonal antibody that specifically binds IGF-II.

36. A composition comprising the bispecific antibody of claim 33 and a pharmaceutically acceptable carrier.

37. An antibody comprising a single domain antibody m630.3 fused to the N terminus of human IgG1 Fc through a hinge linker, wherein single domain antibody m630.3 comprises SEQ ID NO: 5 wherein residue 30 is D, residue 76 is K, residue 104 is R, residue 107 is R, and residue 113 is Y.

38. The antibody of claim 37 comprising SEQ ID NO: 6.

39. A bispecific antibody generated by fusing an scFv m610.27 and a single domain antibody m630.3 to the N termini of the heavy and light chain constant regions of a human IgG1, respectively, via a linker composed of three repeats of $G_4S$;

wherein the variable heavy chain domain of m610.27 is SEQ ID NO: 1 and the variable light chain domain of m610.27 is SEQ ID NO: 2; and wherein the single domain antibody m630.3 comprises SEQ ID NO: 5 wherein residue 30 is D, residue 76 is K, residue 104 is R, residue 107 is R, and residue 113 is Y.

40. The bispecific antibody of claim 39 where scFv m610.27 fused to said heavy chain constant region comprises SEQ ID NO: 7 and where single domain antibody m630.3 fused to said light chain constant region comprises SEQ ID NO: 8.

41. An antibody comprising the heavy chain variable domain of SEQ ID NO: 1 fused to the heavy chain constant domain of SEQ ID NO: 3 and the variable light chain domain of SEQ ID NO: 2 fused to the light chain constant domain of SEQ ID NO: 4.

* * * * *

SEQUENCE LISTING

<160> NUMBER OF SEQ ID NOS: 36

<210> SEQ ID NO 1
<211> LENGTH: 120
<212> TYPE: PRT
<213> ORGANISM: Homo sapiens

<400> SEQUENCE: 1

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Ser Tyr
            20                  25                  30
Tyr Met His Trp Val Arg Gln Ala Pro Gly Gln Gly Leu Glu Trp Met
        35                  40                  45
Gly Ile Ile Asn Pro Ser Gly Gly Ser Thr Ser Tyr Ala Gln Lys Phe
    50                  55                  60
Gln Gly Arg Val Thr Met Thr Arg Asp Thr Ser Thr Ser Thr Val Tyr
65                  70                  75                  80
Met Glu Leu Ser Arg Leu Arg Ser Asp Asp Thr Ala Val Tyr Tyr Cys
                85                  90                  95
Ala Arg Asp Val Gln Trp Leu Ala Tyr Gly Met Asp Val Trp Gly Gln
            100                 105                 110
Gly Thr Thr Val Thr Val Ser Ser
        115                 120
```

<210> SEQ ID NO 2
<211> LENGTH: 108
<212> TYPE: PRT
<213> ORGANISM: Homo sapiens

<400> SEQUENCE: 2

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
Leu Asn Trp Tyr Gln Gln Lys Pro Gly Arg Ala Pro Asp Leu Leu Ile
        35                  40                  45
Asn Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Phe Cys Gln Gln Ser Tyr Ser Leu Pro Phe
                85                  90                  95
Thr Phe Gly Gly Gly Thr Lys Val Glu Ile Lys Gly
            100                 105
```

<210> SEQ ID NO 3
<211> LENGTH: 330
<212> TYPE: PRT
<213> ORGANISM: Homo sapiens

<400> SEQUENCE: 3

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 4
<211> LENGTH: 107
<212> TYPE: PRT
<213> ORGANISM: Homo sapiens

<400> SEQUENCE: 4

Gly Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser

```
                    85                  90                  95

Pro Val Thr Lys Ser Phe Asn Arg Gly Glu Cys
            100                 105

<210> SEQ ID NO 5
<211> LENGTH: 128
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (30)..(30)
<223> OTHER INFORMATION: X can be D or G
<220> FEATURE:
<221> NAME/KEY: MISC_FEATURE
<222> LOCATION: (76)..(76)
<223> OTHER INFORMATION: X can be K or R
<220> FEATURE:
<221> NAME/KEY: MISC_FEATURE
<222> LOCATION: (104)..(104)
<223> OTHER INFORMATION: X can be S or R
<220> FEATURE:
<221> NAME/KEY: MISC_FEATURE
<222> LOCATION: (107)..(107)
<223> OTHER INFORMATION: X can be S or R
<220> FEATURE:
<221> NAME/KEY: MISC_FEATURE
<222> LOCATION: (113)..(113)
<223> OTHER INFORMATION: X can be Y or H

<400> SEQUENCE: 5

Gln Val Gln Leu Val Gln Ser Gly Gly Gly Leu Val Gln Pro Gly Gly
1               5                   10                  15

Ser Leu Arg Leu Ser Cys Ala Ala Ser Ser Phe Asp Phe Xaa Tyr Tyr
            20                  25                  30

Glu Met Ser Trp Val Arg Gln Ala Pro Gly Gln Arg Leu Glu Trp Val
        35                  40                  45

Ala Tyr Ile Ser Lys Ser Gly Gly Thr Lys Met Tyr Ala Asp Ser Val
    50                  55                  60

Lys Gly Arg Phe Thr Ile Ser Arg Asp Asn Ser Xaa Asn Thr Leu Tyr
65                  70                  75                  80

Leu Gln Met Asn Thr Leu Arg Ala Glu Asp Thr Ala Met Tyr Tyr Cys
                85                  90                  95

Ala Lys Asp Arg Ala Thr Cys Xaa Gly Gly Xaa Cys Tyr Ser Phe Tyr
            100                 105                 110

Xaa Gly Met Asp Val Trp Gly Gln Gly Thr Leu Val Thr Val Ser Ser
        115                 120                 125

<210> SEQ ID NO 6
<211> LENGTH: 357
<212> TYPE: PRT
<213> ORGANISM: Artificial Sequence
<220> FEATURE:
<223> OTHER INFORMATION: Fusion

<400> SEQUENCE: 6

Gln Val Gln Leu Val Gln Ser Gly Gly Gly Leu Val Gln Pro Gly Gly
1               5                   10                  15

Ser Leu Arg Leu Ser Cys Ala Ala Ser Ser Phe Asp Phe Asp Tyr Tyr
            20                  25                  30

Glu Met Ser Trp Val Arg Gln Ala Pro Gly Gln Arg Leu Glu Trp Val
        35                  40                  45

Ala Tyr Ile Ser Lys Ser Gly Gly Thr Lys Met Tyr Ala Asp Ser Val
```

```
            50                  55                  60
Lys Gly Arg Phe Thr Ile Ser Arg Asp Asn Ser Lys Asn Thr Leu Tyr
 65                  70                  75                  80

Leu Gln Met Asn Thr Leu Arg Ala Glu Asp Thr Ala Met Tyr Tyr Cys
                 85                  90                  95

Ala Lys Asp Arg Ala Thr Cys Arg Gly Gly Arg Cys Tyr Ser Phe Tyr
                100                 105                 110

Tyr Gly Met Asp Val Trp Gly Gln Gly Thr Leu Val Thr Val Ser Ser
                115                 120                 125

Gly Pro Asp Lys Thr His Thr Cys Pro Pro Cys Pro Ala Pro Glu Leu
                130                 135                 140

Leu Gly Gly Pro Ser Val Phe Leu Phe Pro Pro Lys Pro Lys Asp Thr
145                 150                 155                 160

Leu Met Ile Ser Arg Thr Pro Glu Val Thr Cys Val Val Val Asp Val
                165                 170                 175

Ser His Glu Asp Pro Glu Val Lys Phe Asn Trp Tyr Val Asp Gly Val
                180                 185                 190

Glu Val His Asn Ala Lys Thr Lys Pro Arg Glu Glu Gln Tyr Asn Ser
                195                 200                 205

Thr Tyr Arg Val Val Ser Val Leu Thr Val Leu His Gln Asp Trp Leu
                210                 215                 220

Asn Gly Lys Glu Tyr Lys Cys Lys Val Ser Asn Lys Ala Leu Pro Ala
225                 230                 235                 240

Pro Ile Glu Lys Thr Ile Ser Lys Ala Lys Gly Gln Pro Arg Glu Pro
                245                 250                 255

Gln Val Tyr Thr Leu Pro Pro Ser Arg Asp Glu Leu Thr Lys Asn Gln
                260                 265                 270

Val Ser Leu Thr Cys Leu Val Lys Gly Phe Tyr Pro Ser Asp Ile Ala
                275                 280                 285

Val Glu Trp Glu Ser Asn Gly Gln Pro Glu Asn Asn Tyr Lys Thr Thr
                290                 295                 300

Pro Pro Val Leu Asp Ser Asp Gly Ser Phe Phe Leu Tyr Ser Lys Leu
305                 310                 315                 320

Thr Val Asp Lys Ser Arg Trp Gln Gln Gly Asn Val Phe Ser Cys Ser
                325                 330                 335

Val Met His Glu Ala Leu His Asn His Tyr Thr Gln Lys Ser Leu Ser
                340                 345                 350

Leu Ser Pro Gly Lys
                355

<210> SEQ ID NO 7
<211> LENGTH: 590
<212> TYPE: PRT
<213> ORGANISM: Artificial Sequence
<220> FEATURE:
<223> OTHER INFORMATION: Fusion

<400> SEQUENCE: 7

Gln Val Gln Leu Val Gln Ser Gly Ala Glu Val Lys Lys Pro Gly Ala
 1                5                  10                  15

Ser Val Lys Val Ser Cys Lys Ala Ser Gly Tyr Thr Phe Thr Ser Tyr
                 20                  25                  30

Tyr Met His Trp Val Arg Gln Ala Pro Gly Gln Gly Leu Glu Trp Met
             35                  40                  45

Gly Ile Ile Asn Pro Ser Gly Gly Ser Thr Ser Tyr Ala Gln Lys Phe
```

```
            50                  55                  60
Gln Gly Arg Val Thr Met Thr Arg Asp Thr Ser Thr Ser Thr Val Tyr
 65                  70                  75                  80
Met Glu Leu Ser Arg Leu Arg Ser Asp Thr Ala Val Tyr Tyr Cys
                 85                  90                  95
Ala Arg Asp Val Gln Trp Leu Ala Tyr Gly Met Asp Val Trp Gly Gln
                100                 105                 110
Gly Thr Thr Val Thr Val Ser Ser Gly Gly Gly Ser Gly Gly Gly
                115                 120                 125
Gly Ser Gly Gly Gly Ser Asp Ile Gln Met Thr Gln Ser Pro Ser
            130                 135                 140
Ser Leu Ser Ala Ser Val Gly Asp Arg Val Thr Ile Thr Cys Arg Ala
145                 150                 155                 160
Ser Gln Ser Ile Ser Ser Tyr Leu Asn Trp Tyr Gln Gln Lys Pro Gly
                165                 170                 175
Arg Ala Pro Asp Leu Leu Ile Asn Ala Ala Ser Ser Leu Gln Ser Gly
                180                 185                 190
Val Pro Ser Arg Phe Ser Gly Ser Gly Ser Gly Thr Asp Phe Thr Leu
                195                 200                 205
Thr Ile Ser Ser Leu Gln Pro Glu Asp Phe Ala Thr Tyr Phe Cys Gln
210                 215                 220
Gln Ser Tyr Ser Leu Pro Phe Thr Phe Gly Gly Gly Thr Lys Val Glu
225                 230                 235                 240
Ile Lys Arg Gly Gly Gly Gly Ser Gly Gly Gly Gly Ser Gly Gly Gly
                245                 250                 255
Gly Ser Ser Ala Ser Thr Lys Gly Pro Ser Val Phe Pro Leu Ala
            260                 265                 270
Pro Ser Ser Lys Ser Thr Ser Gly Gly Thr Ala Ala Leu Gly Cys Leu
                275                 280                 285
Val Lys Asp Tyr Phe Pro Glu Pro Val Thr Val Ser Trp Asn Ser Gly
            290                 295                 300
Ala Leu Thr Ser Gly Val His Thr Phe Pro Ala Val Leu Gln Ser Ser
305                 310                 315                 320
Gly Leu Tyr Ser Leu Ser Ser Val Val Thr Val Pro Ser Ser Ser Leu
                325                 330                 335
Gly Thr Gln Thr Tyr Ile Cys Asn Val Asn His Lys Pro Ser Asn Thr
                340                 345                 350
Lys Val Asp Lys Lys Val Glu Pro Lys Ser Cys Asp Lys Thr His Thr
            355                 360                 365
Cys Pro Pro Cys Pro Ala Pro Glu Leu Leu Gly Gly Pro Ser Val Phe
            370                 375                 380
Leu Phe Pro Pro Lys Pro Lys Asp Thr Leu Met Ile Ser Arg Thr Pro
385                 390                 395                 400
Glu Val Thr Cys Val Val Val Asp Val Ser His Glu Asp Pro Glu Val
                405                 410                 415
Lys Phe Asn Trp Tyr Val Asp Gly Val Glu Val His Asn Ala Lys Thr
                420                 425                 430
Lys Pro Arg Glu Glu Gln Tyr Asn Ser Thr Tyr Arg Val Val Ser Val
            435                 440                 445
Leu Thr Val Leu His Gln Asp Trp Leu Asn Gly Lys Glu Tyr Lys Cys
            450                 455                 460
Lys Val Ser Asn Lys Ala Leu Pro Ala Pro Ile Glu Lys Thr Ile Ser
465                 470                 475                 480
```

Lys Ala Lys Gly Gln Pro Arg Glu Pro Gln Val Tyr Thr Leu Pro Pro
                485                 490                 495

Ser Arg Asp Glu Leu Thr Lys Asn Gln Val Ser Leu Thr Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
    530                 535                 540

Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys
            580                 585                 590

<210> SEQ ID NO 8
<211> LENGTH: 250
<212> TYPE: PRT
<213> ORGANISM: Artificial Sequence
<220> FEATURE:
<223> OTHER INFORMATION: Fusion

<400> SEQUENCE: 8

Gln Val Gln Leu Val Gln Ser Gly Gly Gly Leu Val Gln Pro Gly Gly
1               5                   10                  15

Ser Leu Arg Leu Ser Cys Ala Ala Ser Ser Phe Asp Phe Asp Tyr Tyr
            20                  25                  30

Glu Met Ser Trp Val Arg Gln Ala Pro Gly Gln Arg Leu Glu Trp Val
        35                  40                  45

Ala Tyr Ile Ser Lys Ser Gly Thr Lys Met Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Thr Leu Arg Ala Glu Asp Thr Ala Met Tyr Tyr Cys
                85                  90                  95

Ala Lys Asp Arg Ala Thr Cys Arg Gly Gly Arg Cys Tyr Ser Phe Tyr
            100                 105                 110

Tyr Gly Met Asp Val Trp Gly Gln Gly Thr Leu Val Thr Val Ser Ser
        115                 120                 125

Gly Gly Gly Gly Ser Gly Gly Gly Gly Ser Gly Gly Gly Gly Ser Arg
    130                 135                 140

Thr Val Ala Ala Pro Ser Val Phe Ile Phe Pro Pro Ser Asp Glu Gln
145                 150                 155                 160

Leu Lys Ser Gly Thr Ala Ser Val Val Cys Leu Leu Asn Asn Phe Tyr
                165                 170                 175

Pro Arg Glu Ala Lys Val Gln Trp Lys Val Asp Asn Ala Leu Gln Ser
            180                 185                 190

Gly Asn Ser Gln Glu Ser Val Thr Glu Gln Asp Ser Lys Asp Ser Thr
        195                 200                 205

Tyr Ser Leu Ser Ser Thr Leu Thr Leu Ser Lys Ala Asp Tyr Glu Lys
    210                 215                 220

His Lys Val Tyr Ala Cys Glu Val Thr His Gln Gly Leu Ser Ser Pro
225                 230                 235                 240

Val Thr Lys Ser Phe Asn Arg Gly Glu Cys
                245                 250

<210> SEQ ID NO 9
<211> LENGTH: 1350
<212> TYPE: DNA
<213> ORGANISM: Homo sapiens

<400> SEQUENCE: 9

| | | | | | |
|---|---|---|---|---|---|
| caagtgcagc | tggtgcagtc | tggggctgag | gtgaagaagc | ctggggcctc | agtgaaggtt | 60 |
| tcctgcaagg | catctggata | caccttcacc | agctactata | tgcactgggt | gcgacaggcc | 120 |
| cctggacaag | gcttgagtg | gatgggaata | atcaaccta | gtggtggtag | cacaagctac | 180 |
| gcacagaagt | tccagggcag | agtcaccatg | accagggaca | cgtccacgag | cacagtctac | 240 |
| atggagctga | gcaggctgag | atctgacgac | acggccgtgt | attactgtgc | gagagatgtg | 300 |
| cagtggctgg | catacggtat | ggacgtctgg | ggccaaggga | ccacggtcac | cgtgagctca | 360 |
| gcctccacca | agggcccatc | ggtcttcccc | ctggcaccct | cctccaagag | cacctctggg | 420 |
| ggcacagcgg | ccctgggctg | cctggtcaag | gactacttcc | ccgaaccggt | gacggtgtcg | 480 |
| tggaactcag | gcgccctgac | cagcggcgtg | cacaccttcc | cggctgtcct | acagtcctca | 540 |
| ggactctact | ccctcagcag | cgtggtgacc | gtgccctcca | gcagcttggg | cacccagacc | 600 |
| tacatctgca | acgtgaatca | caagcccagc | aacaccaagg | tggacaagaa | agttgagccc | 660 |
| aaatcttgtg | acaaaactca | cacatgccca | ccgtgcccag | cacctgaact | cctggggga | 720 |
| ccgtcagtct | tcctcttccc | cccaaaaccc | aaggacaccc | tcatgatctc | ccggacccct | 780 |
| gaggtcacat | gcgtggtggt | ggacgtgagc | cacgaagacc | ctgaggtcaa | gttcaactgg | 840 |
| tacgtggacg | gcgtggaggt | gcataatgcc | aagacaaagc | cgcgggagga | gcagtacaac | 900 |
| agcacgtacc | gtgtggtcag | cgtcctcacc | gtcctgcacc | aggactggct | gaatggcaag | 960 |
| gagtacaagt | gcaaggtctc | caacaaagcc | ctcccagccc | ccatcgagaa | aaccatctcc | 1020 |
| aaagccaaag | gcagccccg | agaaccacag | gtgtacaccc | tgcccccatc | ccgggatgag | 1080 |
| ctgaccaaga | accaggtcag | cctgacctgc | ctggtcaaag | gcttctatcc | cagcgacatc | 1140 |
| gccgtggagt | gggagagcaa | tgggcagccg | gagaacaact | acaagaccac | gcctcccgtg | 1200 |
| ctggactccg | acggctcctt | cttcctctac | agcaagctca | ccgtggacaa | gagcaggtgg | 1260 |
| cagcagggga | acgtcttctc | atgctccgtg | atgcatgagg | ctctgcacaa | ccactacacg | 1320 |
| cagaagagcc | tctccctgtc | tccgggtaaa | | | | 1350 |

<210> SEQ ID NO 10
<211> LENGTH: 642
<212> TYPE: DNA
<213> ORGANISM: Homo sapiens

<400> SEQUENCE: 10

| | | | | | |
|---|---|---|---|---|---|
| gacatccaga | tgacccagtc | tccatcctcc | ctgtctgcat | ctgtaggaga | cagagtcacc | 60 |
| atcacttgcc | gggcaagtca | gagcattagt | agctatttaa | attggtatca | gcagaagcca | 120 |
| gggagagccc | ctgacctcct | gatcaatgct | gcatccagtt | tgcaaagtgg | ggtcccatca | 180 |
| aggttcagtg | gcagtggatc | tgggaccgac | ttcactctca | ccatcagcag | tctccaacct | 240 |
| gaagattttg | caacttactt | ctgtcaacag | agttacagtt | tccgttcac | tttcggcgga | 300 |
| gggaccaagg | tggagatcaa | aggaactgtg | gctgcaccat | ctgtcttcat | cttcccgcca | 360 |
| tctgatgagc | agttgaaatc | tggaactgcc | tctgttgtgt | gcctgctgaa | taacttctat | 420 |
| cccagagagg | ccaaagtaca | gtggaaggtg | gataacgccc | tccaatcggg | taactcccag | 480 |

```
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gt                       642
```

<210> SEQ ID NO 11
<211> LENGTH: 384
<212> TYPE: DNA
<213> ORGANISM: Homo sapiens

<400> SEQUENCE: 11

```
caggtgcagc tggtgcagtc tgggggaggc ttggtacagc ctggagggtc cctgagactc     60
tcctgtgcag cctcttcttt cgatttcgat tattatgaaa tgagctgggt ccgccaggct    120
ccaggacaac ggcttgagtg ggttgcatac attagtaaga gtggcggtac caaaatgtat    180
gcagactcgg tgaagggccg attcaccatc tccagagaca attccaagaa cacgctgtat    240
ctgcaaatga acaccctgag agccgaggac acagccatgt attactgtgc gaaagatcgg    300
gcaacttgta gtgtggtag ctgctactcc ttttactacg gtatggacgt ctggggccaa    360
ggcaccctgg tcaccgtctc ctca                                           384
```

<210> SEQ ID NO 12
<211> LENGTH: 384
<212> TYPE: DNA
<213> ORGANISM: Homo sapiens

<400> SEQUENCE: 12

```
caggtgcagc tggtgcagtc tgggggaggc ttggtacagc ctggagggtc cctgagactc     60
tcctgtgcag cctcttcttt cgatttcgat tattatgaaa tgagctgggt ccgccaggct    120
ccaggacaac ggcttgagtg ggttgcatac attagtaaga gtggcggtac caaaatgtat    180
gcagactcgg tgaagggccg attcaccatc tccagagaca attccaggaa cacgctgtat    240
ctgcaaatga acaccctgag agccgaggac acagccatgt attactgtgc gaaagatcgg    300
gcaacttgta gaggtggtag ctgctactcc ttttaccacg gtatggacgt ctggggccaa    360
ggcaccctgg tcaccgtctc ctca                                           384
```

<210> SEQ ID NO 13
<211> LENGTH: 384
<212> TYPE: DNA
<213> ORGANISM: Homo sapiens

<400> SEQUENCE: 13

```
caggtgcagc tggtgcagtc tgggggaggc ttggtacagc ctggagggtc cctgagactc     60
tcctgtgcag cctcttcttt cgatttcgat tattatgaaa tgagctgggt ccgccaggct    120
ccaggacaac ggcttgagtg ggttgcatac attagtaaga gtggcggtac caaaatgtat    180
gcagactcgg tgaagggccg attcaccatc tccagagaca attccaagaa cacgctgtat    240
ctgcaaatga acaccctgag agccgaggac acagccatgt attactgtgc gaaagatcgg    300
gcaacttgta gaggtggtcg ctgctactcc ttttactacg gtatggacgt ctggggccaa    360
ggcaccctgg tcaccgtctc ctca                                           384
```

<210> SEQ ID NO 14
<211> LENGTH: 384
<212> TYPE: DNA
<213> ORGANISM: Homo sapiens

<400> SEQUENCE: 14

```
caggtgcagc tggtgcagtc tgggggaggc ttggtacagc ctggagggtc cctgagactc    60
tcctgtgcag cctcttcttt cgatttcggt tattatgaaa tgagctgggt ccgccaggct   120
ccaggacaac ggcttgagtg ggttgcatac attagtaaga gtggcggtac caaaatgtat   180
gcagactcgg tgaagggccg attcaccatc tccagagaca attccaagaa cacgctgtat   240
ctgcaaatga acaccctgag agccgaggac acagccatgt attactgtgc gaaagatcgg   300
gcaacttgta gtggtggtag atgctactcc ttttactacg gtatggacgt ctggggccaa   360
ggcaccctgg tcaccgtctc ctca                                          384
```

<210> SEQ ID NO 15
<211> LENGTH: 384
<212> TYPE: DNA
<213> ORGANISM: Homo sapiens

<400> SEQUENCE: 15

```
caggtgcagc tggtgcagtc tgggggaggc ttggtacagc ctggagggtc cctgagactc    60
tcctgtgcag cctcttcttt cgatttcgat tattatgaaa tgagctgggt ccgccaggcc   120
ccaggacaac ggcttgagtg ggttgcatac attagtaaga gtggcggtac caaaatgtat   180
gcagactcgg tgaagggccg attcaccatc tccagagaca attccaagaa cacgctgtat   240
ctgcaaatga acaccctgag agccgaggac acagccatgt attactgtgc gaaagatcgg   300
gcaacttgta gtggtggtag gtgctactcc ttttactacg gtatggacgt ctggggccaa   360
ggcaccctgg tcaccgtctc ctca                                          384
```

<210> SEQ ID NO 16
<211> LENGTH: 1071
<212> TYPE: DNA
<213> ORGANISM: Homo sapiens

<400> SEQUENCE: 16

```
caggtgcagc tggtgcagtc tgggggaggc ttggtacagc ctggagggtc cctgagactc    60
tcctgtgcag cctcttcttt cgatttcgat tattatgaaa tgagctgggt ccgccaggct   120
ccaggacaac ggcttgagtg ggttgcatac attagtaaga gtggcggtac caaaatgtat   180
gcagactcgg tgaagggccg attcaccatc tccagagaca attccaagaa cacgctgtat   240
ctgcaaatga acaccctgag agccgaggac acagccatgt attactgtgc gaaagatcgg   300
gcaacttgta gaggtggtcg ctgctactcc ttttactacg gtatggacgt ctggggccaa   360
ggcaccctgg tcaccgtctc ctcagggccc gacaaaactc acacatgccc accgtgccca   420
gcacctgaac tcctgggggg accgtcagtc ttcctcttcc ccccaaaacc caaggacacc   480
ctcatgatct cccggacccc tgaggtcaca tgcgtggtgg tggacgtgag ccacgaagac   540
cctgaggtca agttcaactg gtacgtggac ggcgtggagg tgcataatgc caagacaaag   600
ccgcgggagg agcagtacaa cagcacgtac cgtgtggtca gcgtcctcac cgtcctgcac   660
caggactggc tgaatggcaa ggagtacaag tgcaaggtct ccaacaaagc cctcccagcc   720
cccatcgaga aaaccatctc caaagccaaa gggcagcccc gagaaccaca ggtgtacacc   780
ctgcccccat cccgggatga gctgaccaag aaccaggtca gcctgacctg cctggtcaaa   840
ggcttctatc ccagcgacat cgccgtggag tgggagagca atgggcagcc ggagaacaac   900
tacaagacca cgcctcccgt gctggactcc gacggctcct tcttcctcta cagcaagctc   960
accgtggaca agagcaggtg gcagcagggg aacgtcttct catgctccgt gatgcatgag  1020
```

```
gctctgcaca accactacac gcagaagagc ctctccctgt ctccgggtaa a          1071
```

<210> SEQ ID NO 17
<211> LENGTH: 1770
<212> TYPE: DNA
<213> ORGANISM: Homo sapiens

<400> SEQUENCE: 17

```
caagtgcagc tggtgcagtc tggggctgag gtgaagaagc ctggggcctc agtgaaggtt    60
tcctgcaagg catctggata caccttcacc agctactata tgcactgggt gcgacaggcc   120
cctggacaag gcttgagtg gatgggaata atcaacccta gtggtggtag cacaagctac    180
gcacagaagt tccagggcag agtcaccatg accagggaca cgtccacgag cacagtctac   240
atggagctga gcaggctgag atctgacgac acggccgtgt attactgtgc gagagatgtg   300
cagtggctgg catacggtat ggacgtctgg ggccaaggga ccacggtcac cgtctcctca   360
ggtggaggcg gttcaggcgg aggtggctct ggcggtggcg gatcagacat ccagatgacc   420
cagtctccat cctccctgtc tgcatctgta ggagacagag tcaccatcac ttgccgggca   480
agtcagagca ttagtagcta tttaaattgg tatcagcaga gccagggag agcccctgac    540
ctcctgatca atgctgcatc cagtttgcaa agtggggtcc catcaaggtt cagtggcagt   600
ggatctggga ccgacttcac tctcaccatc agcagtctcc aacctgaaga ttttgcaact   660
tacttctgtc aacagagtta cagtcttccg ttcacttttcg cggagggac caaggtggag   720
atcaaacgag gtgaggcgg ttcaggcgga ggtggctctg gcggtggcgg atcgagctca    780
gcctccacca agggcccatc ggtcttcccc ctggcaccct cctccaagag cacctctggg    840
ggcacagcgg ccctgggctg cctggtcaag gactacttcc ccgaaccggt gacggtgtcg    900
tggaactcag gcgccctgac cagcggcgtg cacaccttcc cggctgtcct acagtcctca    960
ggactctact ccctcagcag cgtggtgacc gtgccctcca gcagcttggg cacccagacc   1020
tacatctgca acgtgaatca caagcccagc aacaccaagg tggacaagaa agttgagccc   1080
aaatcttgtg acaaaactca cacatgccca ccgtgcccag cacctgaact cctggggggga   1140
ccgtcagtct tcctcttccc cccaaaaccc aaggacaccc tcatgatctc ccggaccccct   1200
gaggtcacat gcgtggtggt ggacgtgagc cacgaagacc ctgaggtcaa gttcaactgg   1260
tacgtggacg gcgtggaggt gcataatgcc aagacaaagc cgcgggagga gcagtacaac   1320
agcacgtacc gtgtggtcag cgtcctcacc gtcctgcacc aggactggct gaatggcaag   1380
gagtacaagt gcaaggtctc caacaaagcc ctcccagccc ccatcgagaa aaccatctcc   1440
aaagccaaag gcagccccg agaaccacag gtgtacaccc tgcccccatc ccgggatgag   1500
ctgaccaaga accaggtcag cctgacctgc ctggtcaaag gcttctatcc cagcgacatc   1560
gccgtggagt gggagagcaa tgggcagccg gagaacaact acaagaccac gcctcccgtg   1620
ctggactccg acggctcctt cttcctctac agcaagctca ccgtggacaa gagcaggtgg   1680
cagcagggga acgtcttctc atgctccgtg atgcatgagg ctctgcacaa ccactacacg   1740
cagaagagcc tctccctgtc tccgggtaaa                                   1770
```

<210> SEQ ID NO 18
<211> LENGTH: 750
<212> TYPE: DNA
<213> ORGANISM: Homo sapiens

<400> SEQUENCE: 18

```
caggtgcagc tggtgcagtc tggggggaggc ttggtacagc ctggagggtc cctgagactc    60
```

```
tcctgtgcag cctcttcttt cgatttcgat tattatgaaa tgagctgggt ccgccaggct    120
ccaggacaac ggcttgagtg ggttgcatac attagtaaga gtggcggtac caaaatgtat    180
gcagactcgg tgaagggccg attcaccatc tccagagaca attccaagaa cacgctgtat    240
ctgcaaatga cacccctgag agccgaggac acagccatgt attactgtgc gaaagatcgg    300
gcaacttgta gaggtggtcg ctgctactcc ttttactacg gtatggacgt ctggggccaa    360
ggcaccctgg tcaccgtctc ctcaggtgga ggcggttcag gcggaggtgg ctctggcggt    420
ggcggatcac gaactgtggc tgcaccatct gtcttcatct tcccgccatc tgatgagcag    480
ttgaaatctg gaactgcctc tgttgtgtgc ctgctgaata acttctatcc cagagaggcc    540
aaagtacagt ggaaggtgga taacgccctc caatcgggta actcccagga gagtgtcaca    600
gagcaggaca gcaaggacag cacctacagc ctcagcagca ccctgacgct gagcaaagca    660
gactacgaga aacacaaagt ctacgcctgc gaagtcaccc atcagggcct gagctcgccc    720
gtcacaaaga gcttcaacag gggagagtgt                                      750
```

```
<210> SEQ ID NO 19
<211> LENGTH: 43
<212> TYPE: DNA
<213> ORGANISM: Artificial Sequence
<220> FEATURE:
<223> OTHER INFORMATION: Primer, sense

<400> SEQUENCE: 19
tggtttcgct accgtggccc aggcggccca ggtgcagctg gtg                       43

<210> SEQ ID NO 20
<211> LENGTH: 41
<212> TYPE: DNA
<213> ORGANISM: Artificial Sequence
<220> FEATURE:
<223> OTHER INFORMATION: Primer, antisense

<400> SEQUENCE: 20
gtcgccgtgg tggtggtggt ggtggccggc ctggccactt g                         41

<210> SEQ ID NO 21
<211> LENGTH: 43
<212> TYPE: DNA
<213> ORGANISM: Artificial Sequence
<220> FEATURE:
<223> OTHER INFORMATION: Primer, sense

<400> SEQUENCE: 21
tggtttcgct accgtggccc agccggccca ggtgcagctg gtg                       43

<210> SEQ ID NO 22
<211> LENGTH: 33
<212> TYPE: DNA
<213> ORGANISM: Artificial Sequence
<220> FEATURE:
<223> OTHER INFORMATION: Primer, antisense

<400> SEQUENCE: 22
gtgagttttg tcgggccctg aggagacggt gac                                  33

<210> SEQ ID NO 23
<211> LENGTH: 46
<212> TYPE: DNA
<213> ORGANISM: Artificial Sequence
<220> FEATURE:
```

<223> OTHER INFORMATION: Primer, sense

<400> SEQUENCE: 23
gtgttctaga gccgccacca tggaatggag ctgggtcttt ctcttc        46

<210> SEQ ID NO 24
<211> LENGTH: 42
<212> TYPE: DNA
<213> ORGANISM: Artificial Sequence
<220> FEATURE:
<223> OTHER INFORMATION: Primer, antisense

<400> SEQUENCE: 24
ggagtggaca cctgtagtta ctgacaggaa gaagagaaag ac        42

<210> SEQ ID NO 25
<211> LENGTH: 36
<212> TYPE: DNA
<213> ORGANISM: Artificial Sequence
<220> FEATURE:
<223> OTHER INFORMATION: Primer, sense

<400> SEQUENCE: 25
actacaggtg tccactccca agtgcagctg gtgcag        36

<210> SEQ ID NO 26
<211> LENGTH: 71
<212> TYPE: DNA
<213> ORGANISM: Artificial Sequence
<220> FEATURE:
<223> OTHER INFORMATION: Primer, antisense

<400> SEQUENCE: 26
ccttggagct cgatccgcca ccgccagagc cacctccgcc tgaaccgcct ccacctcgtt        60
tgatctccac c        71

<210> SEQ ID NO 27
<211> LENGTH: 36
<212> TYPE: DNA
<213> ORGANISM: Artificial Sequence
<220> FEATURE:
<223> OTHER INFORMATION: Primer, sense

<400> SEQUENCE: 27
cttacagatg ccagatgtca ggtgcagctg gtgcag        36

<210> SEQ ID NO 28
<211> LENGTH: 48
<212> TYPE: DNA
<213> ORGANISM: Artificial Sequence
<220> FEATURE:
<223> OTHER INFORMATION: Primer, antisense

<400> SEQUENCE: 28
agagccacct ccgcctgaac cgcctccacc tgaggagacg gtgaccag        48

<210> SEQ ID NO 29
<211> LENGTH: 46
<212> TYPE: DNA
<213> ORGANISM: Artificial Sequence
<220> FEATURE:
<223> OTHER INFORMATION: Primer, sense

<400> SEQUENCE: 29
gtgtaagctt accatgggtg tgcccactca ggtcctgggg ttgctg        46

-continued

<210> SEQ ID NO 30
<211> LENGTH: 42
<212> TYPE: DNA
<213> ORGANISM: Artificial Sequence
<220> FEATURE:
<223> OTHER INFORMATION: Primer, antisense

<400> SEQUENCE: 30
acatctggca tctgtaagcc acagcagcag caaccccagg ac         42

<210> SEQ ID NO 31
<211> LENGTH: 51
<212> TYPE: DNA
<213> ORGANISM: Artificial Sequence
<220> FEATURE:
<223> OTHER INFORMATION: Primer, sense

<400> SEQUENCE: 31
tcaggcggag gtggctctgg cggtggcgga tcacgaactg tggctgcacc a    51

<210> SEQ ID NO 32
<211> LENGTH: 32
<212> TYPE: DNA
<213> ORGANISM: Artificial Sequence
<220> FEATURE:
<223> OTHER INFORMATION: Primer, antisense

<400> SEQUENCE: 32
gtgtgaattc attaacactc tcccctgttg aa                  32

<210> SEQ ID NO 33
<211> LENGTH: 15
<212> TYPE: PRT
<213> ORGANISM: Artificial Sequence
<220> FEATURE:
<223> OTHER INFORMATION: Linker

<400> SEQUENCE: 33

Gly Gly Gly Gly Ser Gly Gly Gly Ser Gly Gly Gly Gly Ser
1               5                   10                  15

<210> SEQ ID NO 34
<211> LENGTH: 98
<212> TYPE: PRT
<213> ORGANISM: Homo sapiens

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Met His Trp Val Arg Gln Ala Pro Gly Gln Gly Leu Glu Trp Met
            35                  40                  45

Gly Ile Ile Asn Pro Ser Gly Gly Ser Thr Ser Tyr Ala Gln Lys Phe
        50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

```
<210> SEQ ID NO 35
<211> LENGTH: 95
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro
                85                  90                  95

<210> SEQ ID NO 36
<211> LENGTH: 108
<212> TYPE: PRT
<213> ORGANISM: Homo sapiens

<400> SEQUENCE: 36

Asp Ile Gln Met Thr Gln Ser Pro Ser Pro Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys Arg
            100                 105
```